(12) United States Patent
Castro et al.

(10) Patent No.: US 7,994,191 B2
(45) Date of Patent: *Aug. 9, 2011

(54) HETEROCYCLIC CYCLOPAMINE ANALOGS AND METHODS OF USE THEREOF

(75) Inventors: Alfredo C. Castro, Winchester, MA (US); Michael J. Grogan, Winchester, MA (US); Martin Tremblay, Melrose, MA (US)

(73) Assignee: Infinity Discovery, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/629,382

(22) Filed: Dec. 2, 2009

(65) Prior Publication Data

US 2010/0144775 A1 Jun. 10, 2010

Related U.S. Application Data

(63) Continuation of application No. 12/044,817, filed on Mar. 7, 2008, now Pat. No. 7,648,994.

(60) Provisional application No. 60/893,595, filed on Mar. 7, 2007.

(51) Int. Cl.
*A61K 31/4355* (2006.01)
*A61K 31/438* (2006.01)

(52) U.S. Cl. ........................... 514/302; 514/278
(58) Field of Classification Search ............... 514/278, 514/302

See application file for complete search history.

(56) References Cited

U.S. PATENT DOCUMENTS

| | | | |
|---|---|---|---|
| 6,238,876 B1 | 5/2001 | Altaba | |
| 6,291,516 B1 | 9/2001 | Dudek et al. | |
| 6,432,970 B2 | 8/2002 | Beachy et al. | |
| 6,867,216 B1 | 3/2005 | Beachy et al. | |
| 7,098,196 B1 | 8/2006 | Beachy et al. | |
| 7,230,004 B2 | 6/2007 | Adams et al. | |
| 7,291,626 B1 | 11/2007 | Beachy et al. | |
| 7,407,967 B2 | 8/2008 | Adams et al. | |
| 7,648,994 B2 * | 1/2010 | Castro et al. | 514/278 |
| 7,812,164 B2 | 10/2010 | Austad et al. | |
| 7,875,628 B2 | 1/2011 | Adams et al. | |
| 2003/0114393 A1 | 6/2003 | Liscovitch et al. | |
| 2004/0072913 A1 | 4/2004 | Tas et al. | |
| 2004/0072914 A1 | 4/2004 | Tas et al. | |
| 2004/0110663 A1 | 6/2004 | Dudek et al. | |
| 2004/0126359 A1 | 7/2004 | Lamb et al. | |
| 2004/0127474 A1 | 7/2004 | Dudek et al. | |
| 2006/0094660 A1 | 5/2006 | Thomson | |
| 2006/0128639 A1 | 6/2006 | Beachy | |
| 2006/0142245 A1 | 6/2006 | Beachy et al. | |
| 2007/0009530 A1 | 1/2007 | Altaba | |
| 2007/0231828 A1 | 10/2007 | Beachy et al. | |
| 2007/0281040 A1 | 12/2007 | Weichselbaum et al. | |
| 2008/0019961 A1 | 1/2008 | Wicha et al. | |
| 2008/0057071 A1 | 3/2008 | Watkins et al. | |
| 2008/0058298 A1 | 3/2008 | Beachy et al. | |
| 2008/0095761 A1 | 4/2008 | Beachy et al. | |
| 2008/0118493 A1 | 5/2008 | Beachy et al. | |
| 2008/0269272 A1 | 10/2008 | Adams et al. | |
| 2008/0287420 A1 | 11/2008 | Castro et al. | |
| 2008/0293754 A1 | 11/2008 | Austad et al. | |
| 2009/0012109 A1 | 1/2009 | Austad et al. | |
| 2009/0216022 A1 | 8/2009 | Austad et al. | |
| 2010/0286180 A1 | 11/2010 | Castro et al. | |

FOREIGN PATENT DOCUMENTS

| | | |
|---|---|---|
| WO | WO-95/18856 | 7/1995 |
| WO | WO-96/17924 | 6/1996 |
| WO | WO-00/41545 | 7/2000 |
| WO | WO-01/27135 | 4/2001 |
| WO | WO-01/49279 | 7/2001 |
| WO | WO-02/30462 | 4/2002 |
| WO | WO-02/078703 | 10/2002 |
| WO | WO-03/088964 | 10/2003 |
| WO | WO-2005/013800 | 2/2005 |
| WO | WO-2005/032343 | 4/2005 |
| WO | WO-2005/042700 | 5/2005 |
| WO | WO-2006/026430 | 3/2006 |
| WO | WO-2007/123511 | 11/2007 |
| WO | WO-2008/083248 | 7/2008 |
| WO | WO-2008/083252 | 7/2008 |
| WO | WO-2008/089123 | 7/2008 |

OTHER PUBLICATIONS

Alexandre et al., "Transcriptional Activation of Hedgehog Target Genes in *Drosophilia* is Mediated Directly by the Cubitus Interruptus Protein, a Member of the GLI Family of Zinc Finger DNA-Binding Proteins" Genes and Development (1996) 10:2003-2013.
Bale and Yu, "The Hedgehog Pathway and Basal Cell Carcinomas" Human Molecular Genetics (2001) 10:757-762.
Belloni et al., "Identification of Sonic Hedgehog as a Candidate Gene Responsible for Holoprosencephaly" Nature Genetics (1996) 14:353-356.
Berge et al.,"Pharmaceutical Salts" Journal of Pharmaceutical Sciences (1977) 66:1-19.
Berman et al., "Widespread Requirement for Hedgehog Ligand Stimulation in Growth of Digestive Tract Tumours" Nature (2003) 425:846-851.
Berman et al., "Medullablastoma Growth Inhibition by Hedgehog Pathway Blockade" Science (2002) 297:1559-1561.
Bhat et al., "Synthesis and Biological Evaluation of Novel Steroidal Pyrazoles as Substrates for Bile Acid Transportes" Bioorganic and Medicinal Chemistry Letters (2005) 15:85-87.
Chen et al., "Inhibition of Hedgehog Signaling by Direct Binding of Cyclopamine to Smoothened" Genes and Development (2002) 16:2743-2748.
Clinton et al., "Steroidal Heterocycles. VI. Formylation of A/B-cis-3-Ketosteroids. Preparation of 5-beta-Steroidal[3,2-c]pyrazoles" Journal of Organic Chemistry (1960) 27:2800-2807.
Cooper et al., "Teratogen-Mediated Inhibition of Target Tissue Response to Shh Signaling" Science (1998) 280:1603-1607.
Christiansen et al., "Antiandrogenic Steroidal Sulfonylpyrazoles" J. Med. Chem. (1990) 33:2094-2100.

(Continued)

*Primary Examiner* — Charanjit Aulakh
(74) *Attorney, Agent, or Firm* — Fish & Richardson P.C.

(57) ABSTRACT

The present invention relates to steroidal alkaloids that can be used in the treatment of hedgehog pathway related disorders, particularly cancer.

56 Claims, No Drawings

OTHER PUBLICATIONS

Fahrenholtz et al., "Cycloprop[16-alpha-17-alpha]androstanes" J. Med. Chem. (1972) 15:1056-1060.

Fan et al., "Hedgehog Singaling Promotes Prostate Zenograft Tumor Growth" Endocrinology (2004) 145:3961-3970.

Holton and Necoechea, "Steroids. CLXXV. Further Steroidal Anabolic Agents" J. Med. Chem. (1962) 1352-1357.

Karhadker et al., "Hedgehog Signalling in Prostate Regeneration, Neoplasia and Metastasis" Nature (2004) 431:707-712.

Kitajima et al., "Steroid Alkaloids of Fresh Bulbs of *Fritillaria thunbergii* Miq. and of Crude Drug "BAI-MO" Prepared Therefrom" Heterocycles (1981) 15:791-796.

Kubo et al., "Hedgehog Signaling Pathway is a New Therapeutic Target for Patients with Breast Cancer" Cancer Research (2004) 64:6071-6074.

Lee et al., "Development of an Enzyme-linked Immunosorbent Assay for the *Veratrum* Plant Teratogens: Cyclopamine and Jervine" Journal of Agricultural and Food Chemistry (2003) 51:582-586.

Lewis and Veltmaat, "Next Stop, the Twilight Zone: Hedgehog Network Regulation of Mammary Gland Development" Journal of Mammary Gland Biology and Neoplasia (2004) 2:165-181.

Ma et al., "Frequent activation of the hedgehog pathway in advanced gastric adenocarcinomas" Carcinogenesis (2005) 10:1698-1705.

Mrozik et al., "Heterocyclic Steroids in the Antiinflammatory Series" J. Med. Chem. (1964) 7:584-589.

Nakamura at al., "Induction of Osteogenic Differentiation by Hedgehog Proteins" Biochemical and Biophysical Research Communications (1997) 237:465-469.

Ohta et al., "Investigations on Steroids. XI. Synthesis of Steroidal Oxazole, Imidazole, and Triazole" Chem. Pharm. Bull. (1968) 16:1487-1497.

Patil et al., "Hedgehog Signaling in Human Hepatocellular Carcinoma" Cancer Biology & Therapy (2006) 5:111-117.

Peacock et al., "Hedgehog Signaling Maintains a Tumor Stem Cell Compartment in Multiple Myeloma" PNAS USA (2007) 104:4048-4053.

Pietsch et al., "Medulloblastomas of the Desmoplastic Variant Carry Mutations of the Human Homologue of *Drosophila* Patched" Cancer Research (1997) 57:2085-2088.

Quirk et al.,"The Smoothened Gene and Hedgehog Signal Transduction in *Drosophila* and Vertebrate Development" Cold Spring Harbor Symposium Quant. Biol. (1997) 62:217-226.

Rahman et al., "Alkaloids from *Veratrum album*" Phytochemistry (1991) 1:368-370.

Reifenberger et al., "Missense Mutations in SMOH in Sporadic Basal Cell Carcinomas of the Skin and Primitive Neuroectodermal Tumors of the Central Nervous System" Cancer Research (1998) 58:1798-1803.

Sheng et al., "Activation of the Hedgehog Pathway in Advanced Prostate Cancer" Molecular Cancer (2004) 3:29-42.

Sicklick et al., "Dysregulation of the Hedgehog Pathway in Human Hepatocarcinogenesis" Carcinogenesis (2006) 27:748-757.

TAS and AVCI, "Rapid Clearance of Psoriatic Skin Lesions Induced by Topical Cyclopamine" Dermatology (2004) 209:126-131.

Thayer et al., "Hedgehog is an Early and Late Mediator of Pancreatic Cancer Tumorigenesis" Nature (2003) 425:851-856.

Van Der Horst et al., "Hedgehog Stimulates Only Osteoblastic Differentiation of Undifferentiated KS483 cells" Bone (2003) 33:899-910.

Watkins et al.,"Hedgehog Signaling Within Airway Epithelial Progenitors and in Small-Cell Lung Cancer" Nature (2003) 422:313-317.

Williams et al., "Identification of a Small Molecule Inhibitor of the Hedgehog Signaling Pathway: Effects on Basal Cell Carcinoma-Like Lesions" PNAS USA (2003) 100:4616-4621.

Xie et al., "Activating Smoothened Mutations in Sporadic Basal-Cell Carcinoma" Nature (1998) 391:90-92.

International Search Report for PCT/US05/30406, published as WO/2006/026430, mailed on Apr. 4, 2006, 2 pages.

Supplementary Partial European Search Report for EP 05791140.6, mailed Nov. 26, 2007, 4 pages.

International Search Report and Written Opinion for PCT/US2008/003200, mailed Aug. 11, 2008, 10 pages.

Aboulkassim, Tahar O. et al., "Alteration of the Patched locus in Superficial Bladder Cancer", Oncogene, vol. 22, (2003), pp. 2967-2971.

Bar, Elis E. et al., "Cyclopamine-Mediated Hedgehog Pathway Inhibition Depletes Stem-Like Cancer Cells in Gliobastoma", Stem Cells, vol. 25, (2007), pp. 2524-2533.

Bhattacharya, Resham et al., "Role of Hedgehog Signaling in Ovarian Cancer", Clin. Cancer Research, vol. 14, No. 23, (2008), pp. 7659-7666.

Clement, Virginie et al., "Hedgehod-GLI1 Signaling Regulates Human Glioma Growth, Cancer Stem Cell Self-Renewal and Tumorigenicity", Current Biology, vol. 17, (2007), pp. 1-8.

Cutcliffe, Colleen et al., Clear Cell Sarcoma of the Kidney: Up-regulation of Neural Markers with Activation of the Sonic Hedgehog and Akt Pathways, Human Cancer Biology, vol. 11, No. 22, (2005), pp. 7986-7994.

Dierks, Christine et al., "Essential Role of Stromally induced hedgehog signaling in B-cell malignancies", Nature Medicine, (2007), pp. 1-8.

Dierks, Christine et al., "Expansion of Bcr-Abl-Positive Leukemic Stem Cells is Dependent on Hedgehog Pathway Activation", Cancer Cell, vol. 14, (2008), pp. 238-249.

Dormeyer, Wilma et al., "Plasma Membrane Proteomics of Human Embryonic Stem Cells and Human Embryonal Carcinoma Cells", Journal of Proteome Research, vol. 7, (2008), pp. 2936-2951.

Ehtesham, M. et al., "Ligand dependent activation of the hedgehog pathway in glioma progenitor cells", Ongogene (2007), pp. 1-10.

Feldmann, Georg et al., "Blockade of Hedgehog Signaling Inhibits Pancreatic Cancer Invasion and Metastases: A New Paradigm for Combination Therapy in Solid Cancers", Cancer Research, vol. 67, No. 5, (2007), pp. 2187-2196.

Geng, Ling et al., "Hedgehod signaling in the murine melanoma microenvironment", Angiogenesis, vol. 10, (2007) pp. 259-267.

Hegde, Ganapati V. et al., "Hedgehog-Induced Survival of B-Cell Chronic Lymphocytic Leukemia Cells in a Stromal Cell Microenvironment: A Potential New Therapeutic Target, Mol. Cancer Res., vol. 6, (2008), pp. 1928-1936.

Ji, Zhenyu et al., "PKA, Not EPAC, Suppresses Hedgehog Activity and Regulates Glucocorticoid Sensitivity in Acute Lymphoblastic Leukemia Cells", Journal of Biological Chemistry, (2007), pp. 1-19.

Lindemann, Ralph K., "Stroma-Initiated Hedgehog Signaling Takes Center Stage in B-Cell Lymphoma", Cancer Research, vol. 68, No. 4, (2008), pp. 961-964.

Ma, Xiao-Li et al., "Study of Sonic Hedgehod signaling pathway related molecules in gastric carcinoma", World Journal of Gastroenterology, vol. 12, No. 25, (2006), pp. 3965-3969.

Manna, Joseph D. et al, "Metabolite Identification of IPI-609, a Novel and Potent Inhibitor of the Hedgehog Pathway, in Different Species", (2008), 1 page.

Masamune, T. et al., "Syntheses and NMR Spectra of 22,27-IMINO-17,23-Oxidojervane Derivatives", Tetrahedron, vol. 23, (1967), pp. 1591-1612).

Ohta, Miki et al., p53-Independent Negative Regulation of p21/Cyclin-Dependent Kinase-Interacting Protein 1 by the Sonic Hedgehog-Glioma-Associated Oncogene 1 Pathway in Gastric Carcinoma Cells, Cancer Research, vol. 65, No. 23, (2005), pp. 10822-10829.

Pasca Di Magliano, Marina et al., "Hedgehog Signalling in Cancer Formation and Maintenance", Nature Reviews/Cancer, vol. 3, (2003), pp. 903-911.

Rubin, Lee L. et al., "Targeting the Hedgehog Pathway in Cancer", Nature Reviews/Drug Discovery, vol. 5, (2006), pp. 1026-1033.

Saldanha, Gerald, "The Hedgehog signalling pathway and cancer", Journal of Pathology, vol. 193, (2001), pp. 427-432.

Shiotani, A. et al., "Sonic hedgehog and CDX2 expression in the stomach", J. Gastroenterol. Hepatol., (2008), S161-S166, (publication abstract only enclosed-1 page).

Sims-Mourtada, Jennifer et al., "Hedgehog: an Attribute to Tumor Regrowth after Chemoradiotherapy and a Target to Improve Radiation Response", Clinical Cancer Research, vol. 12, No. 21, (2006), pp. 6565-6572.

Stecca, Barbara et al., "Melanomas require HEDGEHOG-GLI signaling regulated by interactions between GLI1 and the RAS-MEK/AKT pathways", Proceedings of the National Academy of Sciences of the United States of America (PNAS), vol. 104, No. 14, (2007), pp. 5895-5900.

Steg, Adam et al., "Multiple Gene Expression Analyses in Paraffin-Embedded Tissues by TaqMan Low-Density Array", J. Molecular Diagnostics, vol. 8, (2006), pp. 76-83.

Taipale, Jussi et al., "Effects of oncogenic mutations in Smoothened and Patched can be reversed by cyclopamine", Nature, vol. 406, (2000), pp. 1005-1009.

Thievessen, I. et al., J. Cell Physiol., "Hedgehog signaling in normal urothelial cells and urothelial carcinoma cell lines", vol. 203, No. 2, (2005), pp. 372-377, (publication abstract only enclosed-1 page).

Travaglione, Veronica et al., "A novel Hh pathway inhibitor, IPI-926, delays recurrence post-chemotherapy in a primary human SCLC xenograft model #4611", Apr. 2008,1 page.

Tremblay, Martin R., "Semisynthetic Cyclopamine Analogues as Potent and Orally Bioavailable Hedgehog Pathway Antagonists", Journal of Medicinal Chemistry, vol. 51, (2008), pp. 6646-6649.

Wunder, Jay S. et al., "Opportunities for improving the therapeutic ratio for patients with sarcoma", Lancet Oncology, vol. 8, (2007), pp. 513-524.

Yang, Hai-Su and Hinds, Philip W., "pRb-mediated control of epithelial cell proliferation and Indian Hedgehog expression in mouse intestinal development", BMC Developmental Biology, vol. 7, No. 6, (2007), pp. 1-12.

Yoshizaki, Ayumi et al., "Expressionsl of sonic hedgehog, patched, smoothened and Gli-1 in human intestinal stromal tumors and their correlation with prognosis", World Journal of Gastroenterology, vol. 12, No. 35, (2006), pp. 5687-5691.

Zhao, Chen et al., Hedgehog signalling is essential for maintenance of cancer stem cells in myeloid leukaemia, Nature Letters, (Jan. 2009), pp. 1-5.

* cited by examiner

HETEROCYCLIC CYCLOPAMINE ANALOGS AND METHODS OF USE THEREOF

RELATED APPLICATIONS

This application is a continuation of U.S. application Ser. No. 12/044,817, filed Mar. 7, 2008, now U.S. Pat. No. 7,648, 994 which claims the benefit of U.S. Provisional Application No. 60/893,595, filed Mar. 7, 2007, the entire contents of both of these prior applications are incorporated herein by reference.

TECHNICAL FIELD

The present invention generally relates to cyclopamine analogs, pharmaceutical compositions thereof, and methods for using such analogs and compositions. These compounds and compositions can be useful for the treatment of hedgehog mediated disorders, such as cancer and psoriasis.

BACKGROUND

The Hedgehog polypeptide is a secreted protein that functions as a signaling ligand in the hedgehog pathway. Three different forms of the hedgehog protein are found in humans; Sonic hedgehog (Shh), Desert hedgehog (Dhh) and Indian hedgehog (Ihh). Sonic hedgehog is the most prevalent hedgehog member in mammals and also is the best characterized ligand of the hedgehog family. Prior to secretion, Shh undergoes an intramolecular cleavage and lipid modification reaction. The lipid modified peptide is responsible for signaling activities.

Inhibition of the hedgehog pathway in certain cancers has been shown to result in inhibition of tumor growth. For example, anti-hedgehog antibodies have been shown to antagonize the function of the hedgehog pathway and inhibit the growth of tumors. Small molecule inhibition of hedgehog pathway activity has also been shown to result in cell death in a number of cancer types.

Research in this area has focused primarily on the elucidation of hedgehog pathway biology and the discovery of new hedgehog pathway inhibitors. Although inhibitors of the hedgehog pathway have been identified, there still exists the need to identify more potent inhibitors of the hedgehog pathway.

SUMMARY

The present invention relates to analogs of cyclopamine, pharmaceutical compositions, and methods of using them. The invention includes compounds of the formulas (1a) and (1b):

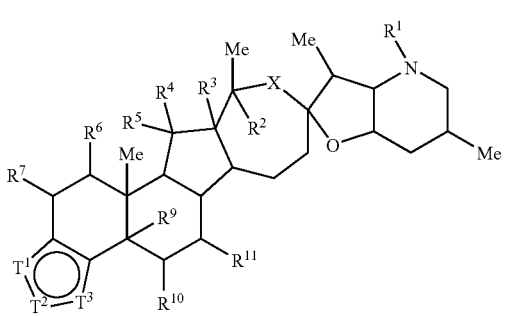

1a

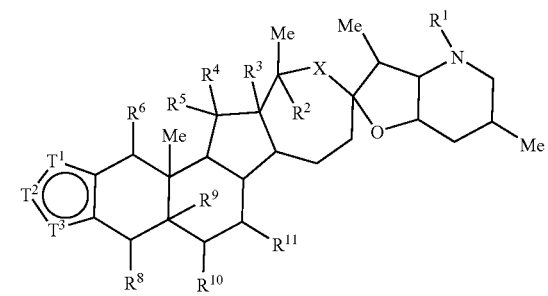

1b and tautomers, saturated derivatives, and pharmaceutically acceptable salts thereof;

wherein;

$R^1$ is H, alkyl, alkenyl, alkynyl, aryl, cycloalkyl, hydroxyl, aralkyl, heteroaryl, heteroaralkyl, haloalkyl, —$SR^{20}$, —$OR^{20}$, —$C(O)R^{20}$, —$CO_2R^{20}$, —$OC(O)R^{20}$, —$C(O)N(R^{20})(R^{20})$, —$S(O)R^{20}$, —$S(O)_2R^{20}$, —$S(O)_2N(R^{20})(R^{20})$, —[(W)—C(O)]$_p$$R^{20}$, —[(W)—C(O)O]$_p$$R^{20}$, —[(W)—OC(O)]$_p$$R^{20}$, —[(W)—SO$_2$]$_p$$R^{20}$, —[(W)—N($R^{20}$)SO$_2$]$_p$$R^{20}$, —[(W)—C(O)N($R^{20}$)]$_p$$R^{20}$, —[(W)—O]$_p$$R^{20}$, —[(W)—N($R^{20}$)]$_p$$R^{20}$, or —[(W)—S]$_p$$R^{20}$;

each of $R^2$, $R^6$ and $R^9$ is independently H, alkyl, alkenyl, alkynyl, cycloalkyl, heterocycloalkyl, aryl, aralkyl, heteroaryl, heteroaralkyl, nitrile, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, or arylthio;

$R^3$ is H; or $R^2$ and $R^3$ taken together form a bond;

each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or $R^4$ and $R^5$ taken together form =O, =S, =N($R^{20}$), =N—O$R^{20}$, or =N(N($R^{20}$)$_2$);

each of $R^7$ and $R^8$ independently is H, alkyl, alkenyl, alkynyl, aryl, cycloalkyl, heterocycloalkyl, or aralkyl; or $R^6$ and $R^7$ taken together form a bond; or $R^8$ and $R^9$ taken together form a bond;

each of $R^{10}$ and $R^{11}$ independently is H, alkyl, alkenyl, alkynyl, aryl, cycloalkyl, heterocycloalkyl, or aralkyl; or $R^9$ and $R^{10}$ taken together form a bond; or $R^{10}$ and $R^{11}$ taken together form a bond;

$R^{20}$ independently for each occurrence is H, alkyl, alkenyl, alkynyl, aryl, cycloalkyl, heterocycloalkyl, aralkyl, heteroaryl, heteroaralkyl, or —[C(R)$_2$]$_q$—$R^{21}$; or any two occurrences of $R^{20}$ can be taken together to form a 4-8 membered optionally substituted ring which contains 0-3 heteroatoms selected from N, O, S, and P;

$R^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or carbonyl-containing group;

$R^{22}$ independently for each occurrence is H, halide, ester, amide, or nitrite;

$R^{23}$ independently for each occurrence is H, alkyl, alkenyl, alkynyl, cycloalkyl, aryl, aralkyl, heteroaryl, heteroaralkyl, perhaloalkyl, halide, nitro, nitrile, —O, —$SR^{20}$, —$OR^{20}$, —$N(R^{20})(R^{20})$, —$C(O)R^{20}$, —$CO_2R^{20}$, —$OC(O)R^{20}$, —$C(O)N(R^{20})(R^{20})$, —N($R^{20}$)C(O)$R^{20}$, —N($R^{20}$)C(O)N($R^{20}$)($R^{20}$), —S(O)$R^{20}$, —S(O)$_2$$R^{20}$, —S(O)$_2$N($R^{20}$)($R^{20}$), —N($R^{20}$)S(O)$_2$$R^{20}$, or —[C(R)$_2$]$_q$—$R^{21}$;

$R^{24}$ independently for each occurrence is H, alkyl, alkenyl, alkynyl, cycloalkyl, aryl, aralkyl, heteroaryl, heteroaralkyl, perhaloalkyl, halide, nitro, nitrile, —S$R^{20}$, —O$R^{20}$, —N($R^{20}$)($R^{20}$), —C(O)$R^{20}$, —CO$_2$$R^{20}$, —OC(O)$R^{20}$, —C(O)N($R^{20}$)($R^{20}$), —N($R^{20}$)C(O)$R^{20}$, —N($R^{20}$)C(O)N($R^{20}$)($R^{20}$), —S(O)$R^{20}$, —S(O)$_2$$R^{20}$, —S(O)$_2$N($R^{20}$)($R^{20}$), —N($R^{20}$)S(O)$_2$$R^{20}$, or —[C(R)$_2$]$_q$—$R^{21}$;

p is 0, 1, 2, 3, 4, 5, or 6;

q is 0, 1, 2, 3, 4, 5, or 6;

R independently for each occurrence is H, alkyl, alkenyl, alkynyl, cycloalkyl, aryl, aralkyl, heteroaryl, or heteroarylalkyl;

-$T^1$-$T^2$-$T^3$- is Y—B-A, B—Y-A, or A-B—Y;

each of A and B independently is N, S or C($R^{23}$);

W is a diradical;

X is a bond or —C($R^{22}$)$_2$—;

Y is —O—, —S—, or —N($R^{24}$)—; and each alkyl, alkenyl, alkynyl, aryl, cycloalkyl, aralkyl, heteroaryl, heteroaralkyl is optionally substituted.

The invention further includes pharmaceutical compositions comprising a compound as set forth above, and methods of using these compounds and compositions for treatment of certain disorders and for inhibition of the hedgehog pathway in vitro or ex vivo, use of such compounds in therapy, and use of such compounds for the manufacture of a medicament.

DETAILED DESCRIPTION

Definitions

The definitions of terms used herein are meant to incorporate the present state-of-the-art definitions recognized for each term in the chemical and pharmaceutical fields. The definitions apply to the terms as they are used throughout this specification, unless otherwise limited in specific instances, either individually or as part of a larger group.

As used herein, the definition of each expression, e.g., alkyl, m, n, etc., when it occurs more than once in any structure, is intended to be independent of its definition elsewhere in the same structure.

The term "acyl" as used herein refers to a group of the general formula R—C(=O)—, where R can be H, alkyl, aryl, or aralkyl. In typical acyl groups, R is H or C1-C6 alkyl, which is optionally substituted, or R can be aralkyl, wherein the aryl portion of the aralkyl is a 5-7 membered aromatic or heteroaromatic ring, and the alkyl portion is a C1-C4 alkylene group; and both the alkyl and aryl portions are optionally substituted as described herein for such groups. Benzyl, p-methoxybenzyl, and phenylethyl are examples of a typical aralkyl.

The term "acylamino" refers to a moiety that may be represented by the general formula:

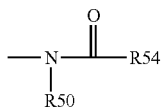

wherein R50 is as defined below, and R54 represents a hydrogen, an alkyl, an alkenyl or —(CH$_2$)$_m$—R61, where m and R61 are as defined below.

The terms "alkenyl" and "alkynyl" refer to unsaturated aliphatic groups analogous in length and possible substitution to the alkyls described below, but that contain at least one double or triple bond respectively. Alkenyl and alkynyl groups may be substituted with the same groups that are suitable as substituents on alkyl groups, to the extent permitted by the available valences. Typical alkenyl and alkynyl groups contain 2-10 carbons in the backbone structure.

The terms "alkoxyl" or "alkoxy" refers to an alkyl group, as defined below, having an oxygen radical attached thereto. Representative alkoxyl groups include methoxy, ethoxy, propyloxy, tert-butoxy and the like. The alkyl portion of an alkoxy group is sized like the alkyl groups, and can be substituted by the same groups that are suitable as substituents on alkyl groups, to the extent permitted by the available valences.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{30}$ for straight chain, $C_3$-$C_{30}$ for branched chain), 20 or fewer. Typically, an alkyl group contains 1-10 carbon atoms as its backbone, and may be substituted or unsubstituted. Likewise, certain cycloalkyls have from 3-10 carbon atoms in their ring structure, and may have 5, 6 or 7 carbons in the ring structure. Unless otherwise indicated, alkyl and cycloalkyl groups, whether alone or as part of another group such as an aralkyl group, can be substituted by suitable substituents such as, but not limited to, halogen, azide, oxo, acyl, cycloalkyl, hydroxyl, alkoxyl, amino, nitro, sulfhydryl, imino, oximino, amido, acylamino, phosphonate, phosphinate, carbonyl, carboxylic acids or their esters or amides, silyl, alkoxy, alkylthio, alkylsulfonyl, alkylsulfonamido, ketone, aldehyde, ester, heterocyclyl, aromatic or heteroaromatic moieties, —CF$_3$, —CN, and the like.

Where alkyl, alkenyl, or alkynyl is part of another group, such as in alkoxy, alkylthio, etc., or it is a substituent on another group, it is frequently an optionally substituted lower alkyl group or lower alkenyl group, having up to six carbon atoms. For such purposes, the typical substituents include halo, —OR', —SR', —SO$_2$R', —SO$_2$NR'$_2$, COOR', CONR'$_2$, oxo, —NR'$_2$, NR'C(O)R', NR'C(O)OR', NR'SO$_2$R', OC(O)R', where each R' is independently H or unsubstituted C1-C6 alkyl, C2-C6 alkenyl, or C2-C6 alkynyl.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined below. Representative alkylthio groups include methylthio, ethyl thio, and the like.

The terms "amido" and "amide" are art recognized as an amino-substituted carbonyl and include a moiety that may be represented by the general formula:

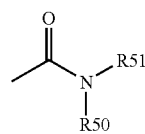

wherein R50 and R51 are as defined below. Certain embodiments of the amide in the present invention will not include imides which may be unstable.

The terms "amine" and "amino" are art-recognized and refer to both unsubstituted and substituted amines, e.g., a moiety that may be represented by the general formulas:

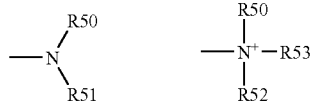

wherein R50, R51, R52 and R53 each independently represent a hydrogen, an alkyl, an alkenyl, —$(CH_2)_m$—R61, where R50 and R51 (or R50 and R52 of the quaternary/charged form), taken together with the N atom to which they are attached, complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "aralkyl", as used herein, whether alone or as part of a group name such as, for example, aralkyloxy, refers to an alkyl group as described herein substituted with an aryl group as described herein (e.g., an aromatic or heteroaromatic group). Both the alkyl and the aryl portion of each aralkyl group are typically optionally substituted. Typical aralkyl groups include, for example, groups of general formula Ar—$(CH_2)_t$—, where Ar represents an aryl ring and t is an integer from 1-6.

The term "aryl" as used herein, whether alone or as part of another name such as 'aryloxy', includes 5-, 6- and 7-membered single-ring aromatic groups that may include from zero to four heteroatoms selected from N, O and S as ring members, as well as fused bicyclic an tricyclic systems consisting of such rings, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carbonyl-containing group, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings, often two rings or three rings, in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls. In some embodiments, each aryl is selected from phenyl, thiophene, furan, pyrrole, pyridine, pyrimidine, pyrazole, imidazole, oxazole, thiazole, isoxazole and isothiazole. Phenyl is sometimes preferred.

The term "Brønsted acid" refers to any substance that can act as a hydrogen ion (proton) donor.

The term "carbonyl-containing group" includes such moieties as may be represented by the general formulas:

wherein X50 is a bond or represents an oxygen or a sulfur, and each of R55 and R56 represents independently a hydrogen, an alkyl, an alkenyl, —$(CH_2)_m$—R61 or a cation representing a pharmaceutically acceptable salt, where m and R61 are defined above. In some embodiments where a carbonyl-containing group is present, it is a carboxylic acid or ester, or an acyloxy group; X50 is O in such embodiments, and R55 or R56, whichever is present, can be H or an optionally substituted alkyl group.

The term "diradical" refers to any of a series of divalent groups from alkyl, alkenyl, alkynyl, aryl, cycloalkyl, heterocycloalkyl, aralkyl, heteroaryl, and heteroaralkyl groups, each of which can be optionally substituted. For example,

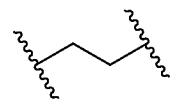

is an alkyl diradical;

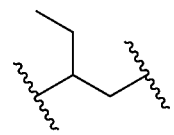

is also an alkyl diradical;

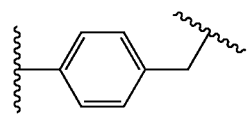

is an aralkyl diradical; and

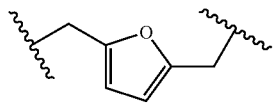

is an (alkyl)heteroaralkyl diradical. Typical examples include alkylenes of general structure $(CH_2)_x$ where x is 1-6, and corresponding alkenylene and alkynylene linkers having 2-6 carbon atoms and one or more double or triple bonds; cycloalkylene groups having 3-8 ring members; groups such as $(CH_2)_a C(=O)(CH_2)_b$, where a and b are each integers from 0-4; and aralkyl groups wherein one open valence is on the aryl ring and one is on the alkyl portion such as

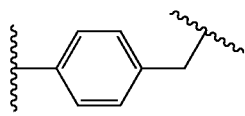

and its isomers. The alkyl, alkenyl, alkynyl, aryl, cycloalkyl, heterocycloalkyl, aralkyl, heteroaryl, and heteroaralkyl portions of a diradical are optionally substituted as described above.

The term "haloalkyl", as used herein, refers to an alkyl group where anywhere from 1 to all hydrogens have been replaced with a halide. A "perhaloalkyl" is where all of the hydrogens have been replaced with a halide.

The term 'heteroalkyl' and 'heterocycloalkyl' refer to alkyl and cycloalkyl groups as described herein, wherein at least one carbon atom of the alkyl or cycloalkyl portion is replaced by a heteroatom selected from N, O and S. Typical examples include methoxymethyl, allylthioethyl, dimethylaminoethyl, and tetrahydrofuranyl.

The term "heteroatom" as used herein means an atom of any element other than carbon or hydrogen. Examples of heteroatoms include boron, nitrogen, oxygen, phosphorus, sulfur and selenium. In certain embodiments, each heteroatom is selected from N, O and S.

The terms "heterocyclyl" or "heterocyclic group" refer to 3- to 10-membered ring structures, in some instances from 3- to 7-membered rings, whose ring structures include at least one carbon atom and one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, triazole, thiazole, oxadiazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carbonyl-containing group, silyl, ether, alkylthio, sulfonyl, ketone, aldehyde, ester, a heterocyclyl, an aromatic or heteroaromatic moiety, —CF$_3$, —CN, or the like.

The term "Lewis acid" refers to any substance that can act as an electron pair acceptor.

Unless the number of carbons is otherwise specified, "lower alkyl" as used herein means an alkyl group, as defined above, but having from one to ten carbons, in some embodiments from one to six carbon atoms in its backbone structure. Likewise, "lower alkenyl" and "lower alkynyl" have similar chain lengths. Certain alkyl groups are lower alkyls. In some embodiments, a substituent designated herein as alkyl is a lower alkyl.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The term "optionally substituted" as used herein indicates that a specified group may be unsubstituted or it may be substituted with one or more substituents to the extent consistent with the number of available valences on the specified group. In some embodiments, each optionally substituted group is substituted with up to four substituents or with 0-3 substituents.

The term "oxo" refers to a carbonyl oxygen (=O).

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carbonyl-containing group, silyl, ether, alkylthio, sulfonyl, ketone, aldehyde, ester, a heterocyclyl, an aromatic or heteroaromatic moiety, —CF$_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M., *Protective Groups in Organic Synthesis*, 2$^{nd}$ ed.; Wiley: New York, 1991).

The term "sugar" as used herein refers to a natural or an unnatural monosaccharide, disaccharide or oligosaccharide comprising one or more pyranose and/or furanose rings. The sugar may be covalently bonded to the steroidal alkaloid of the present invention through an ether linkage or through an alkyl linkage. In certain embodiments the saccharide moiety may be covalently bonded to a steroidal alkaloid of the present invention at an anomeric center of a saccharide ring. Sugars may include, but are not limited to ribose, arabinose, xylose, lyxose, allose, altrose, glucose, mannose, gulose, idose, galactose, talose, glucose, and trehalose.

The terms "triflyl", "tosyl", "mesyl", and "nonaflyl" refer to trifluoromethanesulfonyl, p-toluenesulfonyl, methanesulfonyl, and nonafluorobutanesulfonyl groups, respectively. The terms "triflate", "tosylate", "mesylate", and "nonaflate" refer to trifluoromethanesulfonate ester, p-toluenesulfonate ester, methanesulfonate ester, and nonafluorobutanesulfonate ester functional groups and molecules that contain said groups, respectively.

The term "thioxo" refers to a carbonyl sulfur (=S).

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Where two groups are "taken together form a bond," if the groups are attached to atoms that are not otherwise directly bonded to each other, they represent a bond between the atoms to which they are attached. If the groups are on atoms that are directly bonded to each other, they represent an additional bond between those two atoms. Thus, for example, when $R^2$ and $R^3$ taken together form a bond, the structure —C(A)$R^2$—C(B)$R^3$— represents —C(A)=C(B)—.

The invention includes compounds of formula (1a) or (1b):

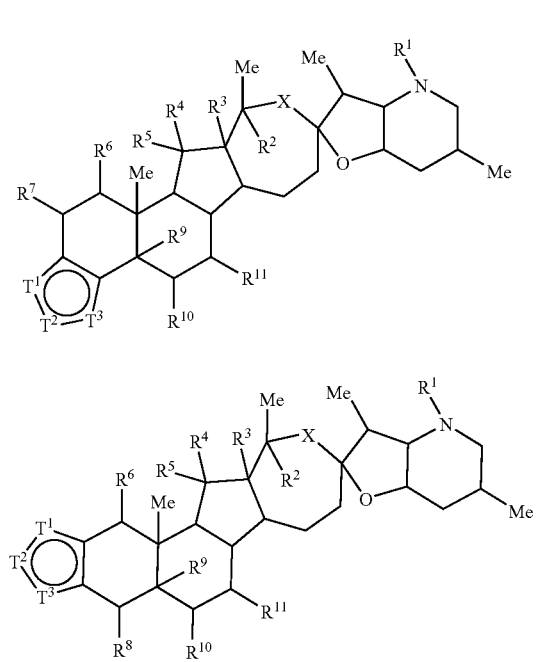

and the tautomers, saturated derivatives, and pharmaceutically acceptable salts thereof;
wherein;
$R^1$ is H, alkyl, alkenyl, alkynyl, aryl, cycloalkyl, hydroxyl, aralkyl, heteroaryl, heteroaralkyl, haloalkyl, —$SR^{20}$, —$OR^{20}$, —C(O)$R^{20}$, —$CO_2R^{20}$, —OC(O)$R^{20}$, —C(O)N($R^{20}$)($R^{20}$), —S(O)$R^{20}$, —S(O)$_2R^{20}$, —S(O)$_2$N($R^{20}$)($R^{20}$), —[(W)—C(O)]$_p R^{20}$, —[(W)—C(O)O]$_p R^{20}$, —[(W)—OC(O)]$_p R^{20}$, [(W)—SO$_2$]$_p R^{20}$, —[(W)—N($R^{20}$)SO$_2$]$_p R^{20}$, —[(W)—C(O)N($R^{20}$)]$_p R^{20}$, —[(W)—O]$_p R^{20}$, —[(W)—N($R^{20}$)]$_p R^{20}$, or —[(W)—S]$_p R^{20}$;
each of $R^2$, $R^6$ and $R^9$ is independently H, alkyl, alkenyl, alkynyl, cycloalkyl, heterocycloalkyl, aryl, aralkyl, heteroaryl, heteroaralkyl, nitrile, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, or arylthio;
$R^3$ is H; or $R^2$ and $R^3$ taken together form a bond;
each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or $R^4$ and $R^5$ taken together form =O, =S, =N($R^{20}$), =N—O$R^{20}$, or =N(N($R^{20}$)$_2$);
each of $R^7$ and $R^8$ independently is H, alkyl, alkenyl, alkynyl, aryl, cycloalkyl, heterocycloalkyl, or aralkyl; or $R^6$ and $R^7$ taken together form a bond; or $R^8$ and $R^9$ taken together form a bond;
each of $R^{10}$ and $R^{11}$ independently is H, alkyl, alkenyl, alkynyl, aryl, cycloalkyl, heterocycloalkyl, or aralkyl; or $R^9$ and $R^{10}$ taken together form a bond; or $R^{10}$ and $R^{11}$ taken together form a bond;
$R^{20}$ independently for each occurrence is H, alkyl, alkenyl, alkynyl, aryl, cycloalkyl, heterocycloalkyl, aralkyl, heteroaryl, heteroaralkyl, or —[C(R)$_2$]$_q$—$R^{21}$; or any two occurrences of $R^{20}$ can be taken together to form a 4-8 membered optionally substituted ring which contains 0-3 heteroatoms selected from N, O, S, and P;
$R^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or a carbonyl-containing group;
$R^{22}$ independently for each occurrence is H, halide, ester, amide, or nitrile;
$R^{23}$ independently for each occurrence is H, alkyl, alkenyl, alkynyl, cycloalkyl, aryl, aralkyl, heteroaryl, heteroaralkyl, perhaloalkyl, halide, nitro, nitrile, =O, —$SR^{20}$, —$OR^{20}$, —N($R^{20}$)($R^{20}$), —C(O)$R^{20}$, —$CO_2R^{20}$, —OC(O)$R^{20}$, —C(O)N($R^{20}$)($R^{20}$), —N($R^{20}$)C(O)$R^{20}$, —N($R^{20}$)C(O)N($R^{20}$)($R^{20}$), —S(O)$R^{20}$, —S(O)$_2R^{20}$, —S(O)$_2$N($R^{20}$)($R^{20}$), —N($R^{20}$)S(O)$_2R^{20}$, or —[C(R)$_2$]$_q$—$R^{21}$;
$R^{24}$ independently for each occurrence is H, alkyl, alkenyl, alkynyl, cycloalkyl, aryl, aralkyl, heteroaryl, heteroaralkyl, perhaloalkyl, halide, nitro, nitrile, —$SR^{20}$, —$OR^{20}$, —N($R^{20}$)($R^{20}$), —C(O)$R^{20}$, —$CO_2R^{20}$, —OC(O)$R^{20}$, —C(O)N($R^{20}$)($R^{20}$), N($R^{20}$)C(O)$R^{20}$, —N($R^{20}$)C(O)N($R^{20}$)($R^{20}$), —S(O)$R^{20}$, —S(O)$_2R^{20}$, —S(O)$_2$N($R^{20}$)($R^{20}$), —N($R^{20}$)S(O)$_2R^{20}$, or [C(R)$_2$]$_q$—$R^{21}$;
p is 0, 1, 2, 3, 4, 5, or 6;
q is 0, 1, 2, 3, 4, 5, or 6;
R independently for each occurrence is H, alkyl, alkenyl, alkynyl, cycloalkyl, aryl, aralkyl, heteroaryl, or heteroarylalkyl;
-$T^1$-$T^2$-$T^3$- is Y—B-A, B—Y-A, or A-B—Y;
each of A and B independently is N, S or C($R^{23}$);
W is a diradical;
X is a bond or —C($R^{22}$)$_2$—;
Y is —O—, —S—, or —N($R^{24}$)—; and
and each alkyl, alkenyl, alkynyl, aryl, cycloalkyl, heterocycloalkyl, aralkyl, heteroaryl, heteroaralkyl, whether alone or part of another group, is optionally substituted.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. Where tautomers are possible in a compound of the invention, the invention includes each tautomeric form. Where stereochemistry of a chiral center is not expressly depicted or described, the structure includes each isomer at that center. Where the absolute stereochemistry of a compound is depicted in a drawing of a structure, the depicted isomer is a preferred embodiment; a racemic mixture of each specifically depicted compound is also an embodiment of the invention.

In certain embodiments, each $R^6$, $R^8$, $R^9$, $R^{10}$, $R^{11}$ that is present in the compounds of formula (1a) or (1b) is either H or alkyl. In some embodiments, the alkyl is preferably a C1-C6 alkyl that is optionally substituted; methyl, meth oxymethyl, trifluoromethyl or ethyl is sometimes preferred. In certain embodiments, each of $R^6$, $R^8$, $R^9$, $R^{10}$, and $R^{11}$ is H, and in some embodiments $R^9$ is taken together with $R^8$ to form a bond, or $R^{10}$ is taken together with $R^{11}$ to form a bond.

In some of the above-described embodiments of the compounds of formula (1a) or (1b), $R^2$ and $R^3$ taken together form a bond, so the carbons on which they appear in the formulas are connected by a double bond.

In some of the foregoing embodiments, $R^4$ and $R^5$ are each H; or $R^4$ and $R^5$ taken together form =O or =S.

In some of the foregoing embodiments, Y is —O— or —N($R^{24}$)—.

In some of the forgoing embodiments, X is a bond, and in others X is $CH_2$.

W in the foregoing embodiments is a diradical, which can be an alkylene, cycloalkylene, arylene, aralkyl diradical, or an (alkyl)arylalkyl diradical, or an (alkyl)heteroarylalkyl diradical. In some embodiments W is an alkylene of the formula $(CH_2)_t$, where t is 1-6 and often t is 1-4. W, or any of its parts, can be substituted with the substituents that are typically suitable for an alkyl or aryl group.

In some embodiments, $R^1$ is defined in terms of W and p, where p is an integer from 0-6; in some preferred embodiments, p is 1.

In some of the foregoing embodiments, $R^1$ is H or alkyl, including optionally substituted C1-C6 alkyl. In other embodiments, $R^1$ is an acyl group, including C(=O)$R^{20}$ or COOR$^{20}$, where $R^{20}$ is as defined above. Specific examples of $R^{20}$ in these embodiments include methyl, ethyl, tert-butyl, phenyl and benzyl. In other embodiments, $R^1$ is OH. In other embodiments, $R^1$ is $SO_2R'$, where R' is C1-C6 alkyl.

In some of the foregoing embodiments, $R^6$ and $R^7$ are both H. In others, $R^6$ and $R^7$ taken together form a bond, so the bond connecting the carbons on which $R^6$ and $R^7$ are depicted is a double bond.

At each occurrence, $R^{20}$ is independently selected as described above. In some of the foregoing embodiments, each $R^{20}$ that is present is independently H or optionally substituted C1-C6 alkyl. Where two $R^{20}$ occur on the same atom or on adjacent atoms, they can cyclize to form an optionally substituted ring having 4-8 ring members as described above, and in some of the foregoing embodiments, two $R^{20}$ on the same atom cyclize to form a 5 or 6 membered ring having up to two heteroatoms selected from N, O, S and P as ring members. In some embodiments, at least one $R^{20}$ is —[C(R)$_2$]$_q$—$R^{21}$, and/or each R is H, and/or q is 0-2.

In formulas (1a) and (1b) and (6a) and (11b), -$T^1$-$T^2$-$T^3$- is fused to a cyclohexane ring to form a fused heteroaromatic group as described above. In the foregoing embodiments, -$T^1$-$T^2$-$T^3$- sometimes represents CR$^{23}$—NR$^{24}$—N or CR$^{23}$—N—NR$^{24}$ or CR$^{23}$—O—N or CR$^{23}$—N—O. In other of these embodiments, -$T^1$-$T^2$-$T^3$- represents N—O—CR$^{23}$ or N—NR$^{24}$—CR$^{23}$ or NR$^{24}$—N—CR$^{23}$. $R^{24}$ in such embodiments can be H or optionally substituted C1-C6 alkyl, or C(O)R$^{20}$, CO$_2$R$^{20}$, CON(R$^{20}$)$_2$, or SO$_2$R$^{20}$; in these embodiments, $R^{20}$ can be H or C1-C6 alkyl or aralkyl, such as benzyl. In other embodiments of formulas (1a) and (1b) and (6a) and (11b), -$T^1$-$T^2$-$T^3$- is —S—CR$^{23}$—N— or —O—CR$^{23}$—N—. $R^{23}$ in all of the foregoing embodiments can be H, halide, or optionally substituted C1-C6 alkyl, including CF$_3$. Frequently in these embodiments, $R^{24}$ is H or C1-C6 alkyl or —SO$_2$—[C1-C6 alkyl].

In some embodiments, the compound of formula (1a) is represented by formula (6a):

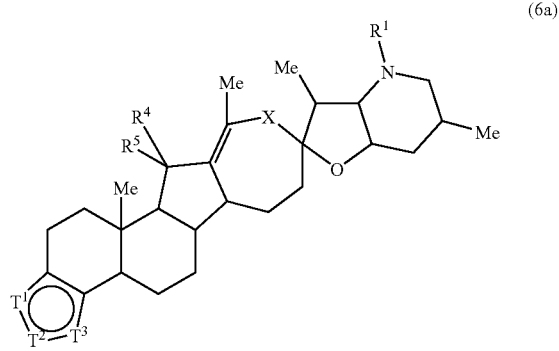

(6a)

or a tautomer, saturated derivative, or pharmaceutically acceptable salt thereof;

wherein;

$R^1$ is H, alkyl, alkenyl, alkynyl, aryl, cycloalkyl, hydroxyl, aralkyl, heteroaryl, heteroaralkyl, haloalkyl, —SR$^{20}$, —OR$^{20}$, —C(O)R$^{20}$, —CO$_2$R$^{20}$, —OC(O)R$^{20}$, —C(O)N(R$^{20}$)(R$^{20}$), —S(O)R$^{20}$, —S(O)$_2$R$^{20}$, —S(O)$_2$N(R$^{20}$)(R$^{20}$), —[(W)—C(O)]$_p$R$^{20}$, —[(W)—C(O)O]$_p$R$^{20}$, —[(W)—OC(O)]$_p$R$^{20}$, —[(W)—SO$_2$]$_p$R$^{20}$, —[(W)—N(R$^{20}$)SO$_2$]$_p$R$^{20}$, —[(W)—C(O)N(R$^{20}$)]$_p$R$^{20}$, —[(W)—O]$_p$R$^{20}$, —[(W)—N(R$^{20}$)]$_p$R$^{20}$, or —[(W)—S]$_p$R$^{20}$;

each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or $R^4$ and $R^5$ taken together form =O or =S;

$R^{20}$ independently for each occurrence is H, alkyl, alkenyl, alkynyl, aryl, cycloalkyl, heterocycloalkyl, aralkyl, heteroaryl, heteroaralkyl, or —[C(R)$_2$]$_q$—$R^{21}$; or any two occurrences of $R^{20}$ can be taken together to form a 4-8 membered optionally substituted ring which contains 0-3 heteroatoms selected from N, O, S, and P;

$R^{21}$ independently for each occurrence is H, cycloalkyl, aryl, heteroaryl, heterocycyl; alkoxyl, aryloxy, acyloxy, halide, sulfhydryl, alkylthio, arylthio, aralkylthio, hydroxyl, amino, acylamino, amido, or a carbonyl-containing group;

$R^{22}$ independently for each occurrence is H, halide, ester, amide, or nitrile;

$R^{23}$ independently for each occurrence is H, alkyl, alkenyl, alkynyl, cycloalkyl, aryl, aralkyl, heteroaryl, heteroaralkyl, perhaloalkyl, halide, nitro, nitrile, =O, —SR$^{20}$, —OR$^{20}$, —N(R$^{20}$)(R$^{20}$), —C(O)R$^{20}$, —CO$_2$R$^{20}$, —OC(O)R$^{20}$, —C(O)N(R$^{20}$)(R$^{20}$), —N(R$^{20}$)C(O)R$^{20}$, —N(R$^{20}$)C(O)N(R$^{20}$)(R$^{20}$), —S(O)R$^{20}$, —S(O)$_2$R$^{20}$, —S(O)$_2$N(R$^{20}$)(R$^{20}$), —N(R$^{20}$)S(O)$_2$R$^{20}$, or —[C(R)$_2$]$_q$—$R^{21}$;

$R^{24}$ independently for each occurrence is H, alkyl, alkenyl, alkynyl, cycloalkyl, aryl, aralkyl, heteroaryl, heteroaralkyl, perhaloalkyl, halide, nitro, nitrile, —SR$^{20}$, —OR$^{20}$, —N(R$^{20}$)(R$^{20}$), —C(O)R$^{20}$, —CO$_2$R$^{20}$, —OC(O)R$^{20}$, —C(O)N(R$^{20}$)(R$^{20}$), —N(R$^{20}$)C(O)R$^{20}$, —N(R$^{20}$)C(O)N(R$^{20}$)(R$^{20}$), —S(O)R$^{20}$, —S(O)$_2$R$^{20}$, —S(O)$_2$N(R$^{20}$)(R$^{20}$), —N(R$^{20}$)S(O)$_2$R$^{20}$, or —[C(R)$_2$]$_q$—$R^{21}$;

p is 0, 1, 2, 3, 4, 5, or 6;

q is 0, 1, 2, 3, 4, 5, or 6;

R independently for each occurrence is H, alkyl, alkenyl, alkynyl, cycloalkyl, aryl, aralkyl, heteroaryl, or heteroarylalkyl;

-$T^1$-$T^2$-$T^3$- is Y—B-A, B—Y-A, or A-B—Y;

each of A and B independently is N, S or $C(R^{23})$;

W is a diradical;

X is a bond or —$C(R^{22})_2$—;

Y is —O—, —S—, or —$N(R^{24})$—; and and each alkyl, alkenyl, alkynyl, aryl, cycloalkyl, heterocycloalkyl, aralkyl, heteroaryl, heteroaralkyl, whether alone or part of another group, is optionally substituted.

In some embodiments of the compounds of formula (6a), X is a bond, and in others X is $CH_2$.

In some of the foregoing embodiments of the compounds of formula (6a), Y is —O—, and in other such embodiments Y is —$N(R^{24})$—. In such embodiments, $R^{24}$ is as defined above, and in some embodiments $R^{24}$ is H, C1-C6 alkyl, or $COOR^{20}$, or $SO_2R^{20}$, where $R^{20}$ is C1-C6 alkyl or aryl-(C1-C6)alkyl, and wherein each alkyl or aryl is optionally substituted.

In such embodiments of the compounds of formula (6a), $R^1$ is as defined above. In some of the foregoing embodiments, $R^1$ is H, C1-C6 alkyl, $COOR^{20}$, or $SO_2R^{20}$, where $R^{20}$ is C1-C6 alkyl or aryl-(C1-C6)alkyl, and wherein each alkyl or aryl is optionally substituted. In some embodiments, p is 1.

In other embodiments, the compound of formula (1b) is a compound of formula (11b):

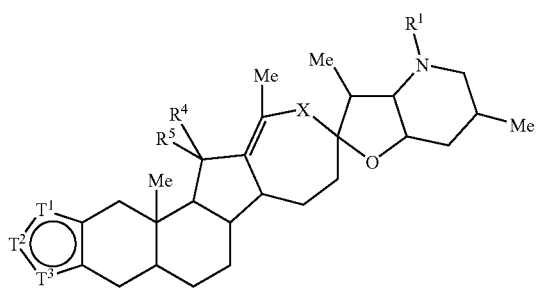

11b or a tautomer, saturated derivative, or pharmaceutically acceptable salt thereof;

wherein;

$R^1$ is H, alkyl, alkenyl, alkynyl, aryl, cycloalkyl, hydroxyl, aralkyl, heteroaryl, heteroaralkyl, haloalkyl, —$SR^{20}$, —$OR^{20}$, —$C(O)R^{20}$, —$CO_2R^{20}$, —$OC(O)R^{20}$, —$C(O)N(R^{20})(R^{20})$, —$S(O)R^{20}$, —$S(O)_2R^{20}$, —$S(O)_2N(R^{20})(R^{20})$, —$[(W)—C(O)]_pR^{20}$, —$[(W)—C(O)O]_pR^{20}$, —$[(W)—OC(O)]_pR^{20}$, —$[(W)—SO_2]_pR^{20}$, —$[(W)—N(R^{20})SO_2]_pR^{20}$, —$[(W)—C(O)N(R^{20})]_pR^{20}$, —$[(W)—O]_pR^{20}$, —$[(W)—N(R^{20})]_pR^{20}$, or —$[(W)—S]_pR^{20}$;

each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or $R^4$ and $R^5$ taken together form =O or =S;

$R^{20}$ independently for each occurrence is H, alkyl, alkenyl, alkynyl, aryl, cycloalkyl, heterocycloalkyl, aralkyl, heteroaryl, heteroaralkyl, or —$[C(R)_2]_q$—$R^{21}$; or any two occurrences of $R^{20}$ can be taken together to form a 4-8 membered optionally substituted ring which contains 0-3 heteroatoms selected from N, O, S, and P;

$R^{21}$ independently for each occurrence is H, cycloalkyl, aryl, heteroaryl, heterocycyl; alkoxyl, aryloxy, acyloxy, halide, sulfhydryl, alkylthio, arylthio, aralkylthio, hydroxyl, amino, acylamino, amido, or a carbonyl-containing group;

$R^{22}$ independently for each occurrence is H, halide, ester, amide, or nitrile;

$R^{23}$ independently for each occurrence is H, alkyl, alkenyl, alkynyl, cycloalkyl, aryl, aralkyl, heteroaryl, heteroaralkyl, perhaloalkyl, halide, nitro, nitrile, =O, —$SR^{20}$, —$OR^{20}$, —$N(R^{20})(R^{20})$, —$C(O)R^{20}$, —$CO_2R^{20}$, —$OC(O)R^{20}$, —$C(O)N(R^{20})(R^{20})$, —$N(R^{20})C(O)R^{20}$, —$N(R^{20})C(O)N(R^{20})(R^{20})$, —$S(O)R^{20}$, —$S(O)_2R^{20}$, —$S(O)_2N(R^{20})(R^{20})$, —$N(R^{20})S(O)_2R^{20}$, or —$[C(R)_2]_q$—$R^{21}$;

$R^{24}$ independently for each occurrence is H, alkyl, alkenyl, alkynyl, cycloalkyl, aryl, aralkyl, heteroaryl, heteroaralkyl, perhaloalkyl, halide, nitro, nitrile, —$SR^{20}$, —$OR^{20}$, —$N(R^{20})(R^{20})$, —$C(O)R^{20}$, —$CO_2R^{20}$, —$OC(O)R^{20}$, —$C(O)N(R^{20})(R^{20})$, —$N(R^{20})C(O)R^{20}$, —$N(R^{20})C(O)N(R^{20})(R^{20})$, —$S(O)R^{20}$, —$S(O)_2R^{20}$, —$S(O)_2N(R^{20})(R^{20})$, —$N(R^{20})S(O)_2R^{20}$, or —$[C(R)_2]_q$—$R^{21}$;

p is 0, 1, 2, 3, 4, 5, or 6;

q is 0, 1, 2, 3, 4, 5, or 6;

R independently for each occurrence is H, alkyl, alkenyl, alkynyl, cycloalkyl, aryl, aralkyl, heteroaryl, or heteroarylalkyl;

-$T^1$-$T^2$-$T^3$- is Y—B-A, B—Y-A, or A-B—Y;

each of A and B independently is N, S or $C(R^{23})$;

W is a diradical;

X is a bond or —$C(R^{22})_2$—;

Y is —O—, —S—, or —$N(R^{24})$—; and and each alkyl, alkenyl, alkynyl, aryl, cycloalkyl, heterocycloalkyl, aralkyl, heteroaryl, heteroaralkyl, whether alone or part of another group, is optionally substituted.

In some embodiments of the compounds of formula (11b), X is a bond, and in others X is $CH_2$.

In some of the foregoing embodiments of the compounds of formula (11b), Y is —O—, and in other such embodiments Y is —$N(R^{24})$—. In such embodiments, $R^{24}$ is as defined above, and in some embodiments $R^{24}$ is H, C1-C6 alkyl, or $COOR^{20}$, or $SO_2R^{20}$, where $R^{20}$ is C1-C6 alkyl or aryl-(C1-C6)alkyl, and wherein each alkyl or aryl is optionally substituted.

In such embodiments of the compounds of formula (11b), $R^1$ is as defined above. In some of the foregoing embodiments, $R^1$ is H, C1-C6 alkyl, $COOR^{20}$, or $SO_2R^{20}$, where $R^{20}$ is C1-C6 alkyl or aryl-(C1-C6)alkyl, and wherein each alkyl or aryl is optionally substituted. In some embodiments, p is 1.

In certain embodiments, the compound of formula (1a) or (1b) is selected from the following compounds and their tautomers and pharmaceutically acceptable salts:

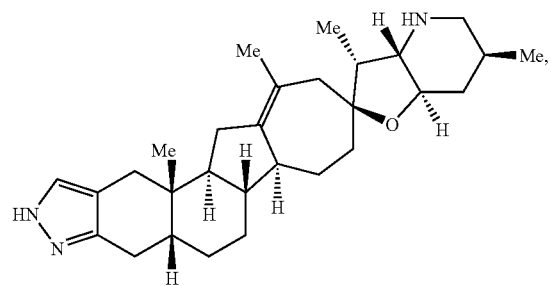
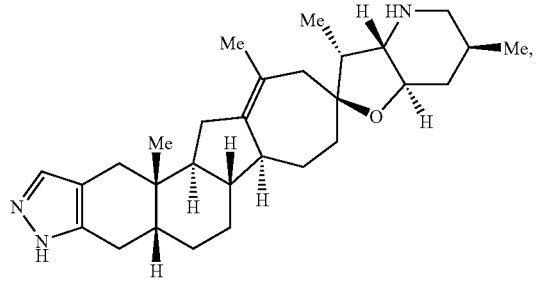
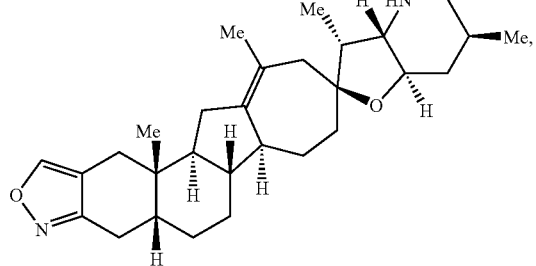
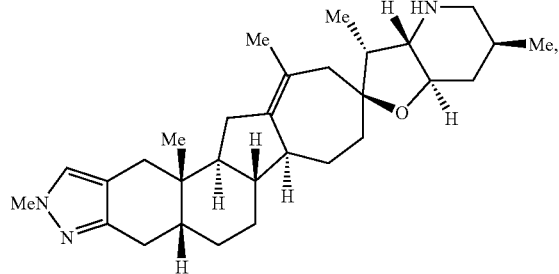
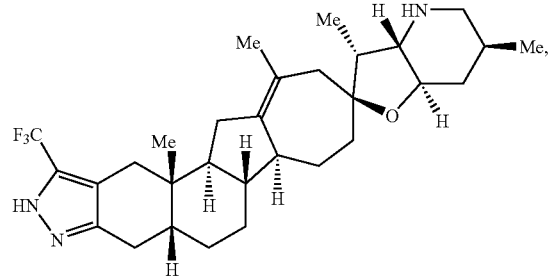
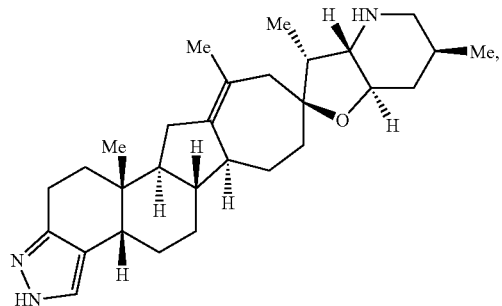
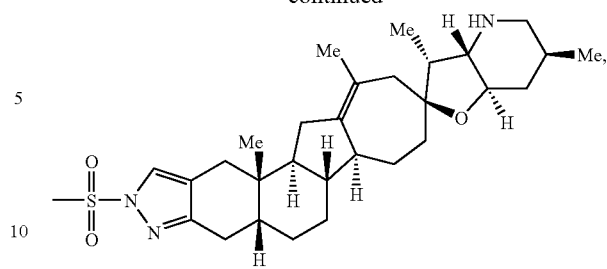
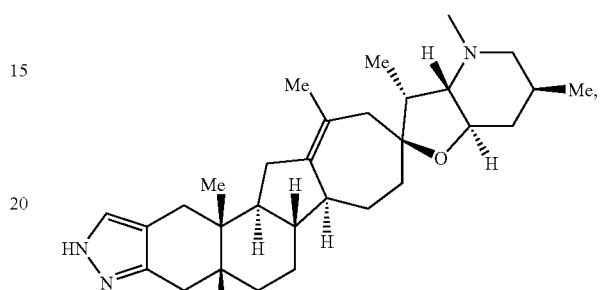
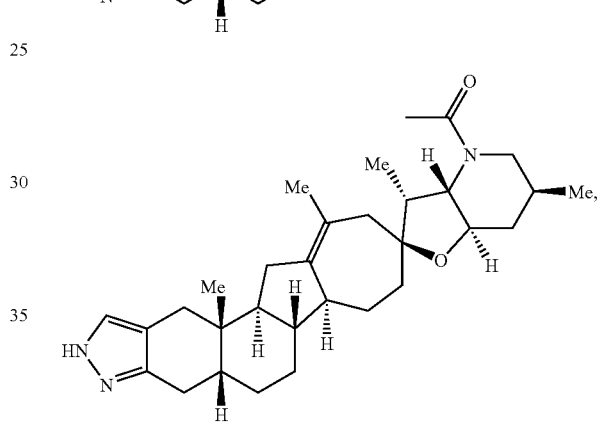
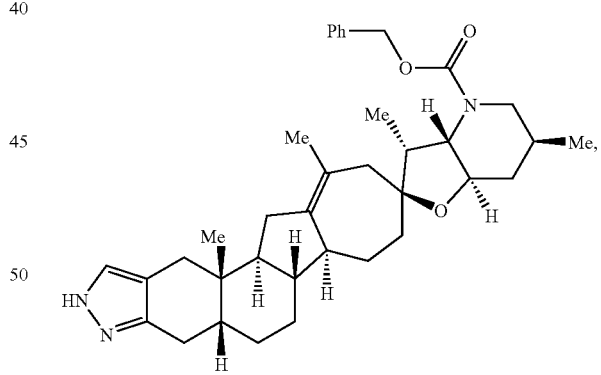
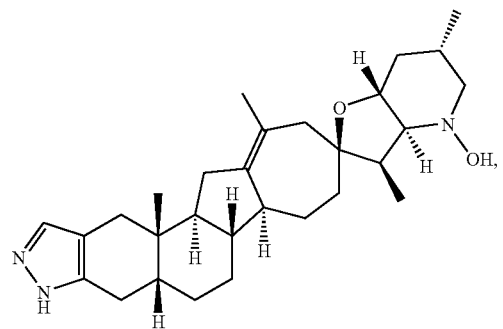

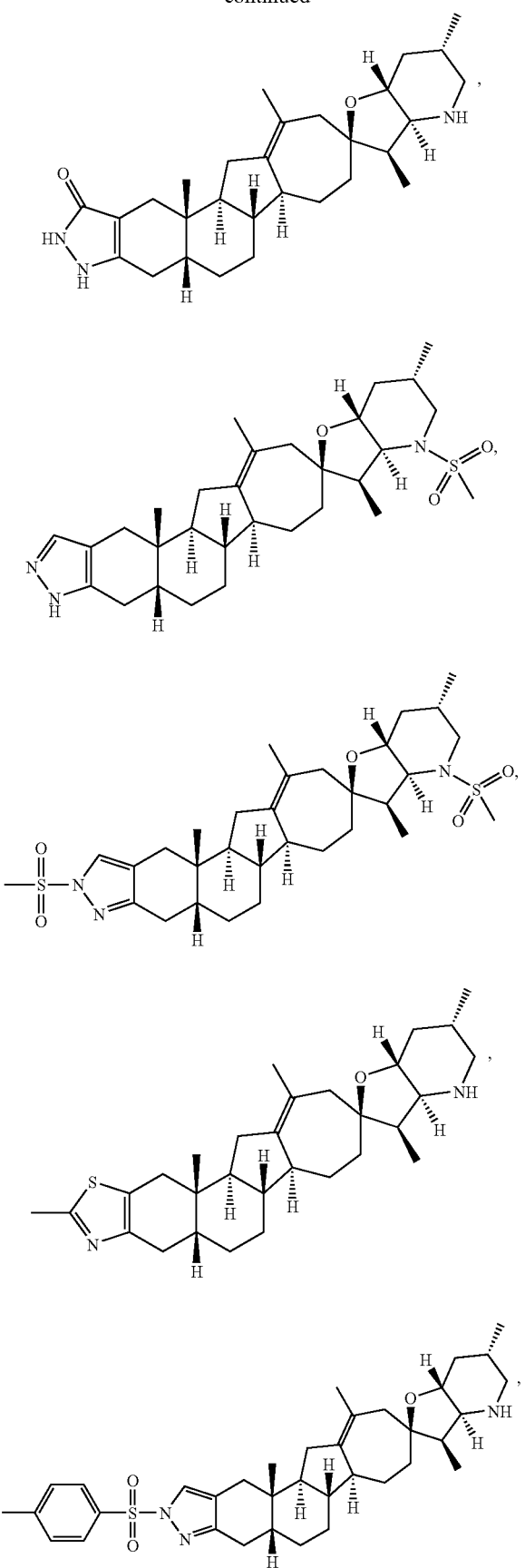

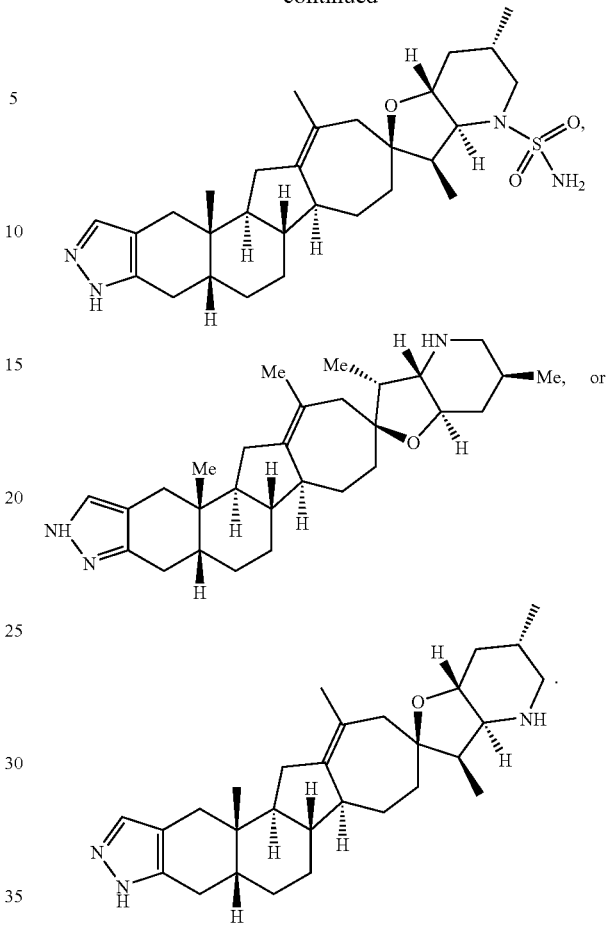

The pharmaceutically acceptable salts of the compounds of the present invention include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge, et al., supra)

In another aspect, the invention provides a pharmaceutical composition comprising at least one compound of formula (1a) or (1b), as described in any of the above embodiments, or a pharmaceutically acceptable salt thereof, admixed with at least one pharmaceutically acceptable excipient. In some embodiments, the compound in the pharmaceutical composition is a compound of formula (6a) or (11b), according to any of the above embodiments.

In another aspect, the invention provides a method of treating a condition mediated by the hedgehog pathway, including administering to a subject an effective amount of a compound described herein. The invention also provides a method of antagonizing the hedgehog pathway in a subject, including administering to the subject an effective amount of a compound described herein. The invention also provides a method of treating cancer in a subject, including administering to a subject a therapeutically effective amount of a compound described herein. Such cancers include cancers of the central nervous system and cancers of the gastrointestinal tract. The invention further provides a method of inhibiting activation of a hedgehog pathway in a patient diagnosed with a hyperproliferative disorder, including administering to the patient a compound described herein in an amount sufficient to reduce the activation of the hedgehog pathway in a cell of the patient.

The invention further provides compounds of formula (1a), (1b), (6a) and/or (11b) and pharmaceutical compositions thereof for use in therapy. It further provides compounds of formula (1a), (1b), (6a) and/or (11b) for use in the manufacture of a medicament. It further provides compounds of formula (1a), (1b), (6a) and/or (11b) for use in manufacture of a medicament to treat disorders mediated by the hedgehog pathway, including cancers as described herein.

In another aspect, the invention provides a method to treat a subject afflicted by excessive activity of a hedgehog pathway, which comprises administering to the subject at least one compound of formula (1a) or (1b), as described in any of the above embodiments, or a pharmaceutically acceptable salt thereof, or a pharmaceutical composition thereof. In some embodiments, the compound in the pharmaceutical composition is a compound of formula (6a) or (11b), according to any of the above embodiments. In some embodiments, the subject is a subject diagnosed with a hyperproliferative disorder, and in some embodiments, the hyperproliferative disorder is cancer.

Synthesis of Steroidal Alkaloid Compounds

The steroidal alkaloid derivatives described above can be prepared directly from naturally occurring steroidal alkaloids or synthetic analogs thereof. In certain instances, the steroidal alkaloid starting materials can be cyclopamine or jervine. These steroidal alkaloids can be purchased commercially or extracted from *Veratrum californicum*. For convenience, the rings of the compounds of the invention that are analogous to those of cyclopamine will sometimes be described by analogy to the rings of cyclopamine, for which the rings are identified as rings A-F:

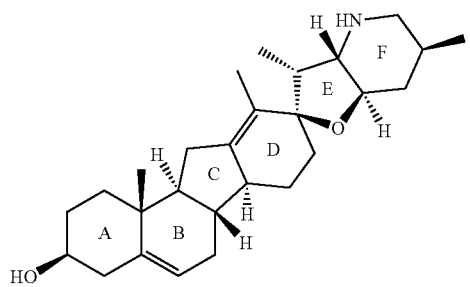

The compounds described above can be synthesized in any number of ways, using combinations of methods that are well known in the art. In certain instances, the compounds are synthesized by condensing 1-keto-3-als derived from steroidal compounds such as cyclopamine with various bi-functional nucleophiles, such as substituted and unsubstituted hydrazines, N-hydroxylamines, or N-mercapto amines. 1-Keto-3-(N-chloro)-imines can be condensed with unsubstituted hydrazines, N-hydro-amines, or N-mercapto amines to access a wide variety of 5 membered heterocycles. [3+2] Cyclo-additions on compounds having a double bond in the A-ring, for example, can be used to access pyrrolidines, isoxazolidines, 1,2,3-triazines, and unsaturated derivatives thereof. Alpha halo ketones can be condensed with primary thio-amides to access thioazoles.

In certain instances, the compounds of the present invention may contain a six or seven membered D-ring. Briefly, as illustrated by the example in Scheme A, the seven membered D-ring analogs may be accessed by cyclopropanating the D-ring of a suitable steroidal alkaloid followed by treating the resulting cyclopropanated product with a Lewis or Brønsted acid to catalyze a ring expansion rearrangement to yield the seven membered D-ring analogs.

Scheme A. Exemplary formation of a 7-membered D-ring.

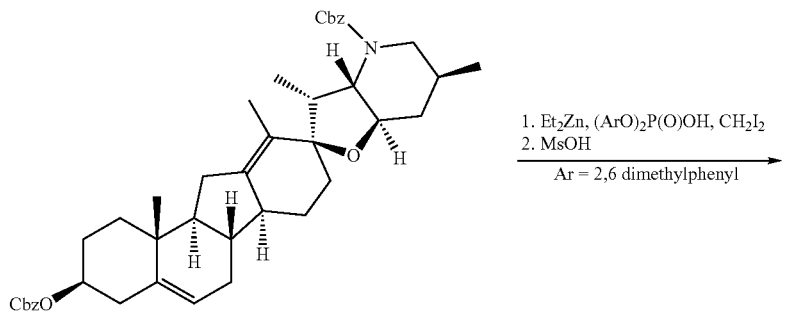

-continued

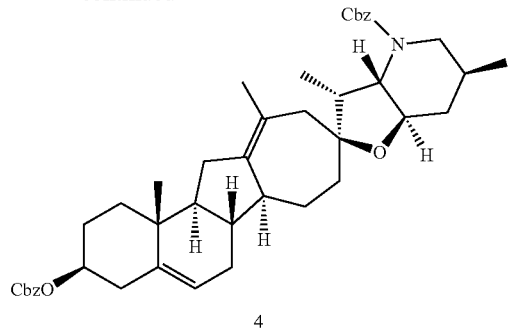

4

This ring expansion of the D-ring can be performed before or after other modifications to the structure, such as modifications of rings A and B, or addition of other fused rings as described herein. These ring expanded analogs may be further functionalized using a variety of functionalization reactions known in the art. Representative examples include palladium coupling reactions to alkenylhalides or aryl halides, oxidations, reductions, reactions with nucleophiles, reactions with electrophiles, pericyclic reactions, installation of protecting groups, removal of protecting groups, and the like.

Pharmaceutical Compositions

The compounds disclosed herein or salts thereof may be formulated into composition suitable for administration, using one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, capsules, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) pulmonarily, or (9) nasally.

Examples of suitable aqueous and nonaqueous carriers which may be employed in the pharmaceutical compositions include water, an aqueous buffer such as PBS, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, dispersing agents, lubricants, and/or antioxidants. Prevention of the action of microorganisms upon the compounds disclosed herein may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Methods of preparing these formulations or compositions include the step of bringing into association a compound with the carrier and, optionally, one or more accessory ingredients. In general, the formulations are prepared by uniformly and intimately bringing into association a compound with liquid carriers, or finely divided solid carriers, or both, and then, if necessary, shaping the product.

When the compounds disclosed herein are administered as pharmaceuticals, to humans and animals, they can be given per se or as a pharmaceutical composition containing, for example, about 0.1 to 99%, or about 10 to 50%, or about 10 to 40%, or about 10 to 30, or about 10 to 20%, or about 10 to 15% of active ingredient in combination with a pharmaceutically acceptable carrier.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound disclosed herein will be that amount of the compound which is the lowest dose effective to produce a therapeutic effect. Such an effective dose will generally depend upon the factors described above. Generally, oral, intravenous and subcutaneous doses of the compounds for a patient, when used for the indicated effects, will range from about 0.0001 to about 200 mg, or about 0.001 to about 100 mg, or about 0.01 to about 100 mg, or about 0.1 to about 100 mg per, or about 1 to about 50 mg per kilogram of body weight per day.

The compounds can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

The subject receiving this treatment is any animal in need, including primates, in particular humans, and other mammals such as equines, cattle, swine and sheep; and poultry and pets in general.

Methods of Treatment

Hedgehog signaling is essential in many stages of development, especially in formation of left-right symmetry. Loss or reduction of hedgehog signaling leads to multiple developmental deficits and malformations, one of the most striking of which is cyclopia.

Many tumors and proliferative conditions have been shown to depend on the hedgehog pathway. The growth of such cells and survival can be affected by treatment with the compounds disclosed herein. Recently, it has been reported that activating hedgehog pathway mutations occur in sporadic basal cell carcinoma (Xie et al. (1998) *Nature* 391: 90-2) and primitive neuroectodermal tumors of the central nervous system (Reifenberger et al. (1998) *Cancer Res* 58: 1798-803). Uncontrolled activation of the hedgehog pathway has also been shown in numerous cancer types such as GI tract cancers including pancreatic, esophageal, gastric cancer (Berman et al. (2003) *Nature* 425: 846-51, Thayer et al. (2003) *Nature* 425: 851-56) lung cancer (Watkins et al. (2003) *Nature* 422: 313-317, prostate cancer (Karhadkar et at (2004) *Nature* 431: 707-12, Sheng et al. (2004) *Molecular Cancer* 3: 29-42, Fan et al. (2004) *Endocrinology* 145: 3961-70), breast cancer (Kubo et al. (2004) *Cancer Research* 64: 6071-74, Lewis et al. (2004) *Journal of Mammary Gland Biology and Neoplasia* 2: 165-181) and hepatocellular cancer (Sicklick et al. (2005) ASCO conference, Mohini et al. (2005) AACR conference).

For example, small molecule inhibition of the hedgehog pathway has been shown to inhibit the growth of basal cell carcinoma (Williams, et al., 2003 PNAS 100: 4616-21), medulloblastoma (Berman et al., 2002 Science 297: 1559-61), pancreatic cancer (Berman et al., 2003 Nature 425: 846-51), gastrointestinal cancers (Berman et al., 2003 Nature 425: 846-51, published PCT application WO 05/013800), esophageal cancer (Berman et al., 2003 Nature 425: 846-51), lung cancer (Watkins et al., 2003. Nature 422: 313-7), and prostate cancer (Karhadkar et al., 2004. Nature 431: 707-12). Accordingly, the compounds and compositions disclosed herein are useful for treatment of medulloblastoma and pancreatic cancers, gastrointestincal cancer, lung cancer and prostate cancer.

In addition, it has been shown that many cancer types have uncontrolled activation of the hedgehog pathway, for example, breast cancer (Kubo et al., 2004. Cancer Research 64: 6071-4), heptacellular cancer (Patil et al., 2005. 96$^{th}$ Annual AACR conference, abstract #2942 Sicklick et al., 2005. ASCO annual meeting, abstract #9610), hematological malignancies (Watkins and Matsui, unpublished results), basal carcinoma (Bale & Yu, 2001. Human Molec. Genet. 10:757-762 Xie et al., 1998 Nature 391: 90-92), medulloblastoma (Pietsch et al., 1997. Cancer Res. 57: 2085-88), and gastric cancer (Ma et al., 2005 Carcinogenesis May 19, 2005 (Epub)). In addition, investigators have found that small molecule inhibition of the hedgehog pathway has been shown to ameliorate the symptoms of psoriasis (Tas, et al., 2004 Dermatology 209: 126-131). As shown in the Examples, the compounds disclosed herein have been shown to modulate the hedgehog pathway, and selected compounds have been shown to inhibit tumor growth. It is therefore believed that these compounds can be useful to treat a variety of hyperproliferative disorders, such as various cancers.

Proliferative disorders that can be treated using the methods disclosed herein include: lung cancer (including small cell lung cancer and non small cell lung cancer), other cancers of the pulmonary system, medulloblastoma and other brain cancers, pancreatic cancer, basal cell carcinoma, breast cancer, prostate cancer and other genitourinary cancers, gastrointestinal stromal tumor (GIST) and other cancers of the gastrointestinal tract, colon cancer, colorectal cancer, ovarian cancer, cancers of the hematopoietic system (including multiple myeloma, acute lymphocytic leukemia, acute myelocytic leukemia, chronic myelocytic leukemia, chronic lymphocytic leukemia, Hodgkin lymphoma, and non-Hodgkin lymphoma, and myelodysplastic syndrome), polycythemia Vera, Waldenstrom's macroglobulinemia, heavy chain disease, soft-tissue sarcomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, melanoma, and other skin cancers, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, bladder carcinoma, and other genitourinary cances, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, endometrial cancer, follicular lymphoma, diffuse large B-cell lymphoma, mantle cell lymphoma, hepatocellular carcinoma, thyroid cancer, gastric cancer, esophageal cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, thyroid cancer, neuroendocrine cancers, and carcinoid tumors. Additional disorders include Gorlin's syndrome and psoriasis The subject receiving this treatment is any animal in need, including primates, in particular humans, and other mammals such as equines, cattle, swine and sheep; and poultry and pets in general.

The hedgehog inhibitors disclosed herein can be combined with other cancer treatments. For example, they can be combined with surgical treatments; radiation; biotherapeutics (such as interferons, cytokines—e.g. Interferon α, Interferon γ, and tumor necrosis factor, hematopoietic growth factors, monoclonal serotherapy, vaccines and immunostimulants); antibodies (e.g. Avastin, Erbitux, Rituxan, and Bexxar); endocrine therapy (including peptide hormones, corticosteroids, estrogens, androgens and aromatase inhibitors); antiestrogens (e.g. Tamoxifen, Raloxifene, and Megestrol); LHRH agonists (e.g. goscrelin and Leuprolide acetate); antiandrogens (e.g. flutamide and Bicalutamide); gene therapy; bone marrow transplantation; photodynamic therapies (e.g. vertoporfin (BPD-MA), Phthalocyanine, photosensitizer Pc4, and Demethoxy-hypocrellin A (2BA-2-DMHA)); and chemotherapeutics.

Examples of chemotherapeutics include gemcitabine, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, and vinorelbine. Additional agents include nitrogen mustards (e.g. cyclophosphamide, Ifosfamide, Trofosfamide, Chlorambucil, Estramustine, and Melphalan), nitrosoureas (e.g. carmustine (BCNU) and Lomustine (CCNU)), alkylsulphonates (e.g. busulfan and Treosulfan), triazenes (e.g. Dacarbazine and Temozolomide), platinum containing compounds (e.g. Cisplatin, Carboplatin, and oxaliplatin), vinca alkaloids (e.g. vincristine, Vinblastine, Vindesine, and Vinorelbine), taxoids (e.g. paclitaxel and Docetaxol), epipodophyllins (e.g. etoposide, Teniposide, Topotecan, 9-Aminocamptothecin, Camptoirinotecan, Crisnatol, Mytomycin C, and Mytomycin C), anti-metabolites, DHFR inhibitors (e.g. methotrexate and Trimetrexate), IMP dehydrogenase Inhibitors (e.g. mycophenolic acid, Tiazofurin, Ribavirin, and EICAR), ribonucleotide reductase Inhibitors (e.g. hydroxyurea and Deferoxamine), uracil analogs (e.g.

Fluorouracil, Floxuridine, Doxifluridine, Ratitrexed, and Capecitabine), cytosine analogs (e.g. cytarabine (ara C), Cytosine arabinoside, and Fludarabine), purine analogs (e.g. mercaptopurine and Thioguanine), Vitamin D3 analogs (e.g. EB 1089, CB 1093, and KB 1060), isoprenylation inhibitors (e.g. Lovastatin), dopaminergic neurotoxins (e.g. 1-methyl-4-phenylpyridinium ion), cell cycle inhibitors (e.g. staurosporine), actinomycins (e.g. Actinomycin D and Dactinomycin), bleomycins (e.g. bleomycin A2, Bleomycin B2, and Peplomycin), anthracyclines (e.g. daunorubicin, Doxorubicin (adriamycin), Idarubicin, Epirubicin, Pirarubicin, Zorubicin, and Mitoxantrone), MDR inhibitors (e.g. verapamil), $Ca^{2+}$ ATPase inhibitors (e.g. thapsigargin), imatinib, thalidomide, lenalidomide, erlotinib, gefitinib, sorafenib, and sunitinib, and proteasome inhibitors, including bortezomib.

When the hedgehog inhibitors disclosed herein are administered in combination with other treatments, such as additional therapeutics or with radiation or surgery, the doses of each agent or therapy will in most instances be lower than the corresponding dose for single-agent therapy. Also, in general, the hedgehog inhibitors described herein and the second therapeutic agent do not have to be administered in the same pharmaceutical composition, and may, because of different physical and chemical characteristics, be administered by different routes. For example, one compound can be administered orally, while the second therapeutic is administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The hedgehog inhibitor and the second therapeutic agent and/or radiation may be administered concurrently (e.g., simultaneously, essentially simultaneously or within the same treatment protocol) or sequentially (i.e., one followed by the other, with an optional time interval in between), depending upon the nature of the proliferative disease, the condition of the patient, and the actual choice of second therapeutic agent and/or radiation to be administered.

If the hedgehog inhibitor, and the second therapeutic agent and/or radiation are not administered simultaneously or essentially simultaneously, then the optimum order of administration may be different for different conditions. Thus, in certain situations the hedgehog inhibitor may be administered first followed by the administration of the second therapeutic agent and/or radiation; and in other situations the second therapeutic agent and/or radiation may be administered first followed by the administration of a hedgehog inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the second therapeutic agent and/or radiation may be administered first, especially if it is a cytotoxic agent, and then the treatment continued with the administration of a hedgehog inhibitor followed, where determined advantageous, by the administration of the second therapeutic agent and/or radiation, and so on until the treatment protocol is complete.

EXEMPLIFICATION

The invention now being generally described, it will be more readily understood by reference to the following examples, which are included merely for purposes of illustration of certain aspects and embodiments of the present invention, and are not intended to limit the invention.

Example 1

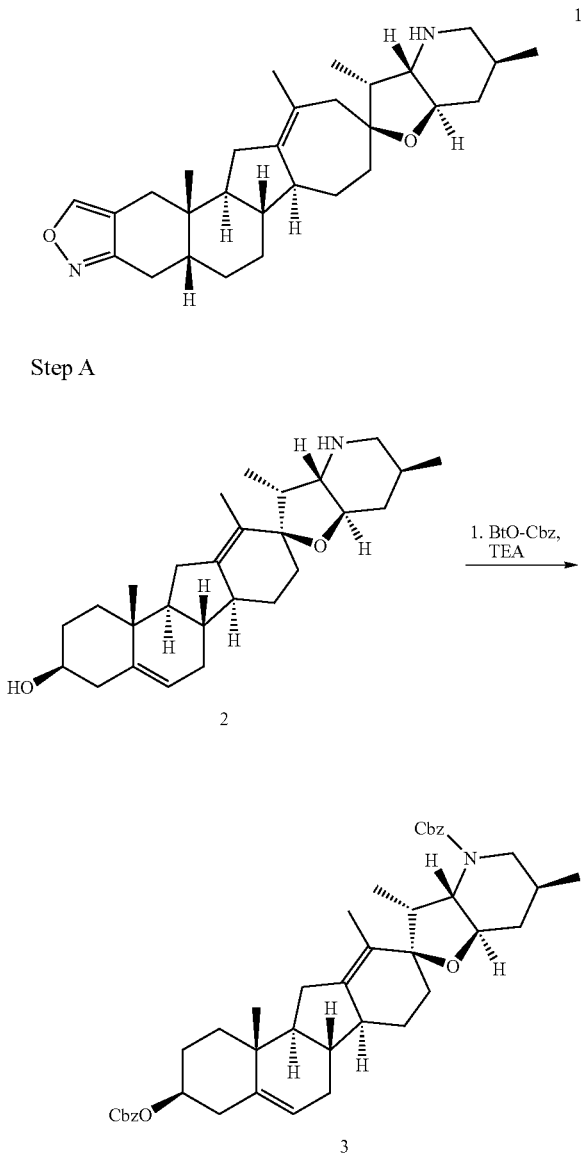

Step A

Cyclopamine 2 (5.02 g, 12.2 mmol, 1.0 eq) was dissolved in anhydrous pyridine (25 mL). DMAP (300 mg, 2.44 mmol, 0.2 eq.) and triethyl amine (5.5 mL, 39.1 mmol, 3.2 eq) were added, followed by BtO-Cbz (10.5 g, 39.1 mmol, 3.2 eq) and the mixture was heated at 40° C. for 2 h. The mixture was cooled to rt, treated with 30 mL water, heated to get a homogeneous solution and allowed to cool to rt. The white precipitate that formed was collected by filtration, the filter cake was washed with portions of water (3×50 mL), and dried in air to afford 9.53 g of crude material which was crystallized from toluene/heptanes (1:9, 70 mL) to give 6.75 g of the desired product.

Step B

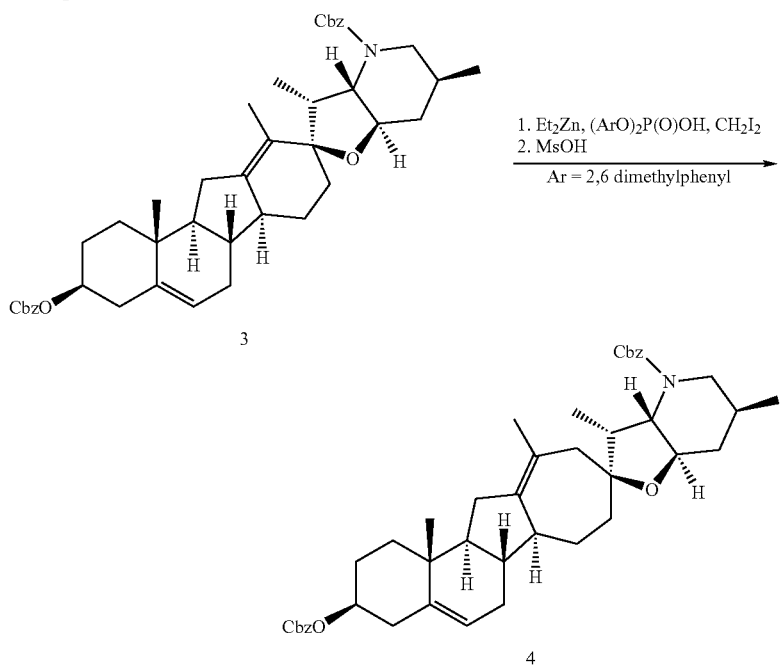

To a solution of diethyl zinc (572 mg, 482 μL, 4.63 mmol, 3 eq) in DCM (5.0 mL) at −20° C. was added a solution of bis-(2,6-Dimethylphenyl)phosphoric acid (1.42 g, 4.63 mmol, 3 eq) in DCM (15 mL) maintaining the reaction temperature below −8° C. The solution was aged for 15 min. at 0° C., neat diiodomethane (1.24 g, 374 μL, 3 eq) was added, the mixture was aged for 15 min. at 0° C. before adding a solution of (Bis-CBz-cyclopamine, 1.05 g, 1.54 mmol, 1.0 eq), in DCM (10 mL). The cooling bath was replaced by a water bath at rt and maintained at rt for 4.5 h. The mixture was cooled to −76° C. with a dry ice-acetone bath and treated drop wise with methanesulfonic acid DCM solution (0.6 mL 50% v/v solution 4.63 mmol, 3.0 eq) maintaining the reaction temperature below −74° C. The mixture was aged for 15-20 min. and quenched drop wise with morpholine (2.69 g, 2.70 mL, 20 eq) maintaining the reaction temperature below −65° C. The cooling bath was removed, the reaction mixture was stirred for 16-18 h., the white precipitate was filtered off, and the filtrate was successively washed with 2.0 M HCl (2×20 mL), satd. sodium bicarbonate (2×20 mL), water (2×20 mL) and brine (20 mL). It was dried over magnesium sulfate, concentrated in vacuo to dryness and the crude was purified by silica gel flash chromatography (hexanes/EtOAc 17:3→4:1) to afford 924 mg (1.33 mmol, 86%) of the desired product.

Step C

-continued

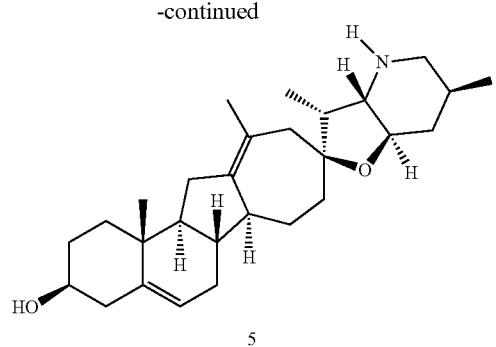

To a solution of compound 4 (4.05 g, 5.83 mmol, 1 eq) in a solution of EtOAc:toluene (2:1, 60 mL) was added 20% palladium hydroxide on carbon (823 mg, 0.583 mmol, 0.1 eq.). The flask was evacuated and filled with hydrogen three times. The mixture was stirred under an atmosphere of hydrogen for 1 h. Neat ethylene diamine (0.38 mL) was added, the mixture was stirred for 1 h, and the catalyst was filtered off. The filter cake was washed twice with EtOAc:toluene (2:1, 12 mL). The combined filtrates were washed with a 2% aqueous solution of ethylene diamine (3×20 mL), dried over sodium sulfate and concentrated in vacuo to give 2.46 g of compound 5 as a white crystalline solid.

Step D

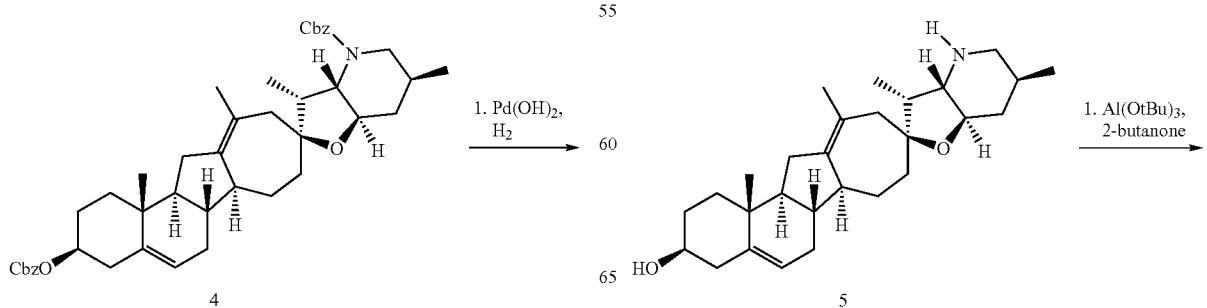

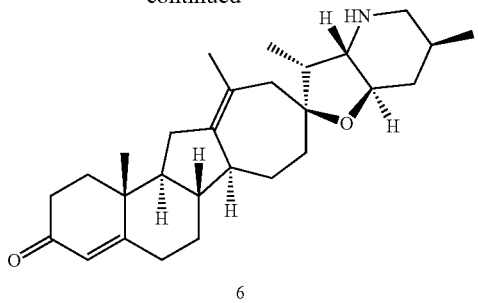

6

A round bottom flask was sequentially charged with the homo-allylic alcohol 14 (7.50 g, 17.6 mmol, 1 eq), aluminum tert-butoxide (6.10 g, 24.8 mmol, 1.4 eq), anhydrous toluene (115 mL), and 2-butanone (90 g, 1.24 mol, 7 eq). The suspension was heated under a nitrogen atmosphere to 75° C. for 16 h. The reaction temperature was then allowed to cool to 49° C. Aqueous 20% (w/w) potassium sodium tartrate solution (226 g) was added to the stirred suspension. The suspension was stirred at rt for 3.5 h. The layers were separated. The organic layer was washed with aqueous 20% Rochelle's salt (2×250 mL) and water (225 mL), then dried over sodium sulfate and filtered. The residue was rinsed with toluene (30 mL) and discarded. The combined organics were concentrated to dryness. Residual reaction solvents were removed from the material by concentrating from 2-propanol (250 mL added portion-wise) to a final solution mass of 44 g. Solvent exchange from 2-propanol to n-heptane (275 mL added portion-wise) to a final solution mass of 41 g fully precipitated the desired product. The suspension was diluted with additional n-heptane (40 mL), stirred at rt for 1 h, and filtered. The product was washed with n-heptane (17 mL) and dried to afford 5.4 g of the desired product.

Step E

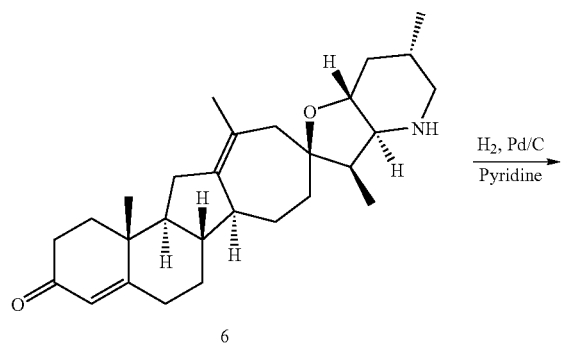

A round-bottom flask was charged with starting material 6 (110 mg, 0.26 mmol, 1 eq) and 10% palladium on carbon (106 mg). The solids were suspended in pyridine (4 mL). The suspension was placed under hydrogen atmosphere (1 atm) and the mixture was stirred overnight at rt. The reaction mixture was filtered through celite and the filtrate concentrated in vacuo. The crude material was purified using silica gel flash chromatography (MeOH/DCM 5:95) to afford 93 mg of the desired compound.

Step F

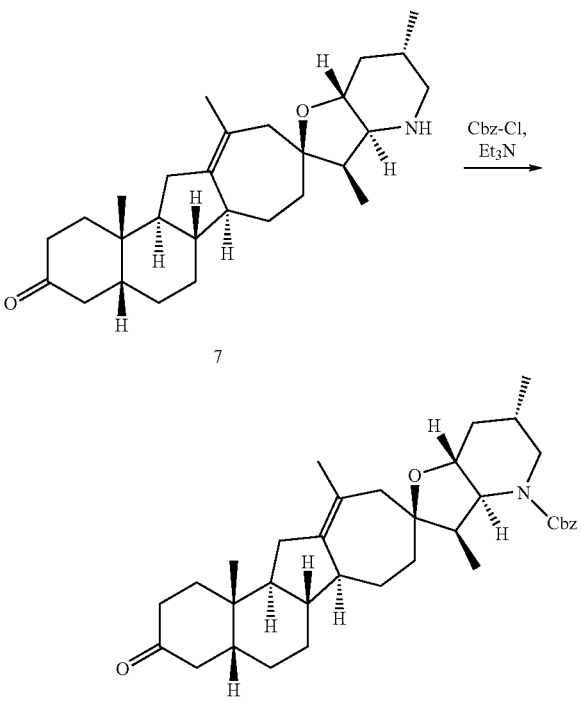

A round-bottom flask was charged with compound 7 (4.23 g, 9.94 mmol, 1 eq) and THF (60 mL). Triethylamine (6.92 mL, 49.7 mmol, 5.0 eq) and benzyl chloroformate (1.54 mL, 10.93 mmol, 1.1 eq) were added and the mixture was stirred for 1 h at rt. The reaction mixture was partitioned between saturated aqueous bicarbonate (100 mL) and EtOAc (100 mL). The phases were separated and the organics were dried (Na$_2$SO$_4$) and concentrated to dryness. The crude material was purified using silica gel flash chromatography (EtOAc/Hexanes 2:98→14:86) to give 3.75 g of material.

Step G

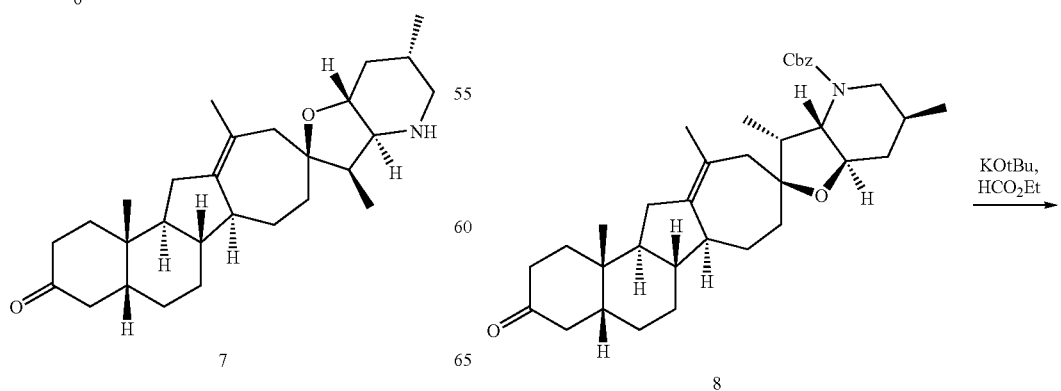

-continued

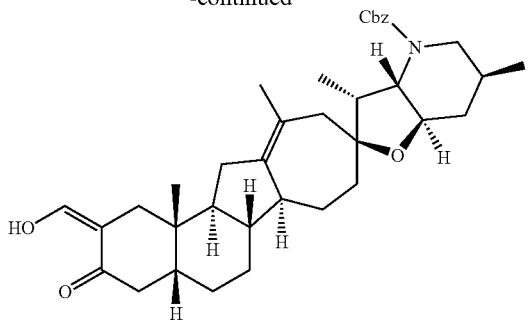

9

A dry round-bottom flask was charged with KOtBu (0.57 g, 5.1 mmol, 7 eq) and tBuOH (6 mL) and the solution was stirred at rt for 10 min. Compound 8 (0.3 g, 0.73 mmol, 1 eq) was added and stirred for 5 min. The white suspension became a yellow clear solution. Ethyl formate (0.35 mL, 4.4 mmol, 6 eq) was added dropwise, and the solution became slightly opaque and produced bubbles. The slurry was stirred at rt for 48 h. The mixture was then portioned between MTBE/1% NaOH (2×20 mL). The aqueous layer was acidified with 2 N HCl until the pH reached 5, then extracted with chloroform (2×). The combined organic layers were washed with water, dried over $Na_2SO_4$, and concentrated to dryness to give 200 mg pale yellow foam. This material was used without further purification in the next step.

Step H

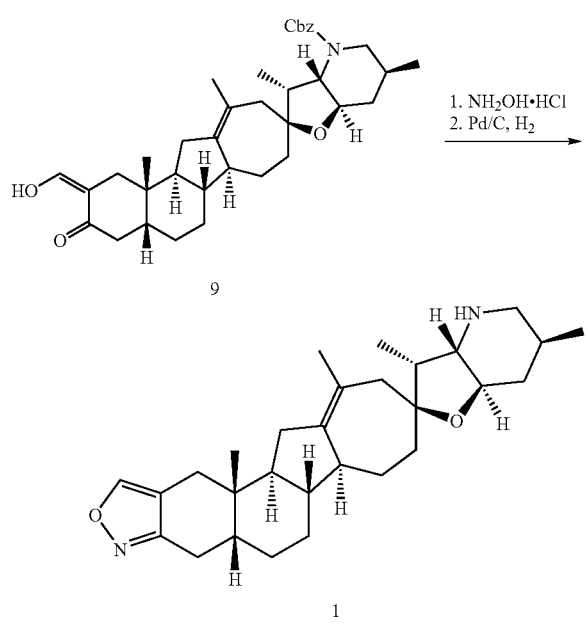

A pyridine solution (4 mL) of compound 9 (200 mg, 0.33 mmol, 1.0 eq) heated at 110° C. was treated with an aqueous solution (1.2 mL) of hydroxylamine HCl (71 mg, 1.0 mmol, 3 eq). After stirring for 4 min, the mixture was partitioned between water and DCM (30 mL each). The organic layer was washed with 1M aqueous HCl (30 mL) and then brine (30 mL), dried over sodium sulfate, and concentrated in vacuo. The crude residue was purified by flash silica gel chromatography (10→40% ether/hexanes) to give the [3,2-c]-isoxazole as a white solid (87.0 mg).

The product carbamate isoxazole was dissolved in EtOAc (7 mL) in a flask with stir bar and rubber septum. The solution was sparged with nitrogen, and 10% Pd/C (wet, Degussa type E101, Aldrich, 25 mg) was added. This mixture was sparged with nitrogen and then hydrogen gas and stirred at it for 2 h. The mixture was then sparged with nitrogen, filtered through a 0.45 µm polyethylene membrane and concentrated to a clear oil. The oil was purified by flash silica gel chromatography (0.5% ammonium hydroxide/2→10% MeOH/DCM), and the pure fractions were concentrated to give an oil that was lyophilized from 7% water/tBuOH, to afford the desired product as a white powder (37 mg: [M+H]=451.7 m/z).

Example 2

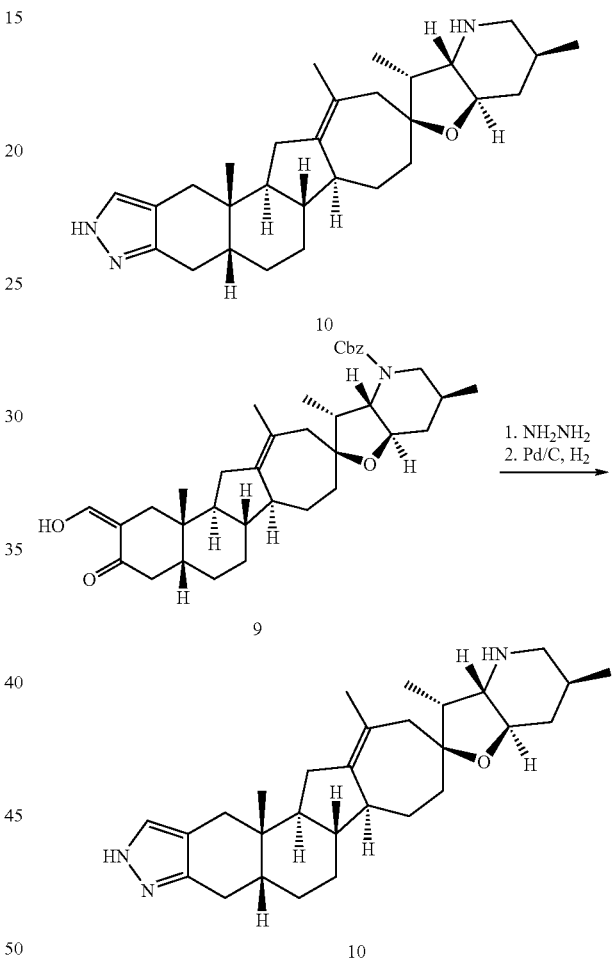

An ethanol solution (4 mL) of compound 9 (100.0 mg, 0.17 mmol, 1.0 eq) was treated with hydrazine (16 mg, 0.34 mmol, 2.0 eq) and heated at 70° C. for 0.5 h. The mixture was concentrated in vacuo and was purified by flash silica gel chromatography (20→60% ether/hexanes) to give the protected pyrazole as a white solid (72.0 mg).

The product carbamate isoxazole was dissolved in EtOAc (7 mL) in a flask with stir bar and rubber septum. The solution was sparged with nitrogen, and 10% Pd/C (wet, Degussa type E101, Aldrich, 25 mg) was added. This mixture was sparged with nitrogen and then hydrogen gas and stirred at it for 2 h. The mixture was then sparged with nitrogen, filtered through a 0.45 µm polyethylene membrane and concentrated to a clear oil. The oil was purified by flash silica gel chromatography (0.5% ammonium hydroxide/2→10% MeOH/DCM), and the pure fractions were concentrated to give an oil that was lyophilized from 7% water/tBuOH, to afford the desired product as a white powder (37 mg: [M+H]=450.6 m/z).

Example 3

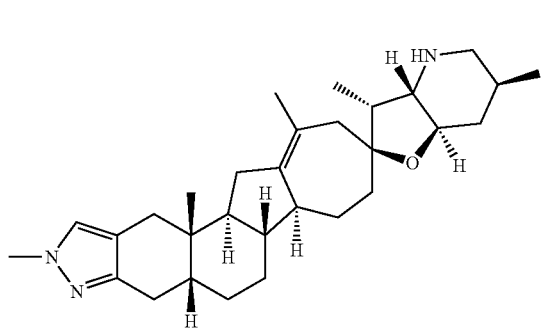

Compound 11 was made according to the procedure described in example 2, using methyl hydrazine in place of hydrazine. ([M+H]=464.7 m/z)

Example 4

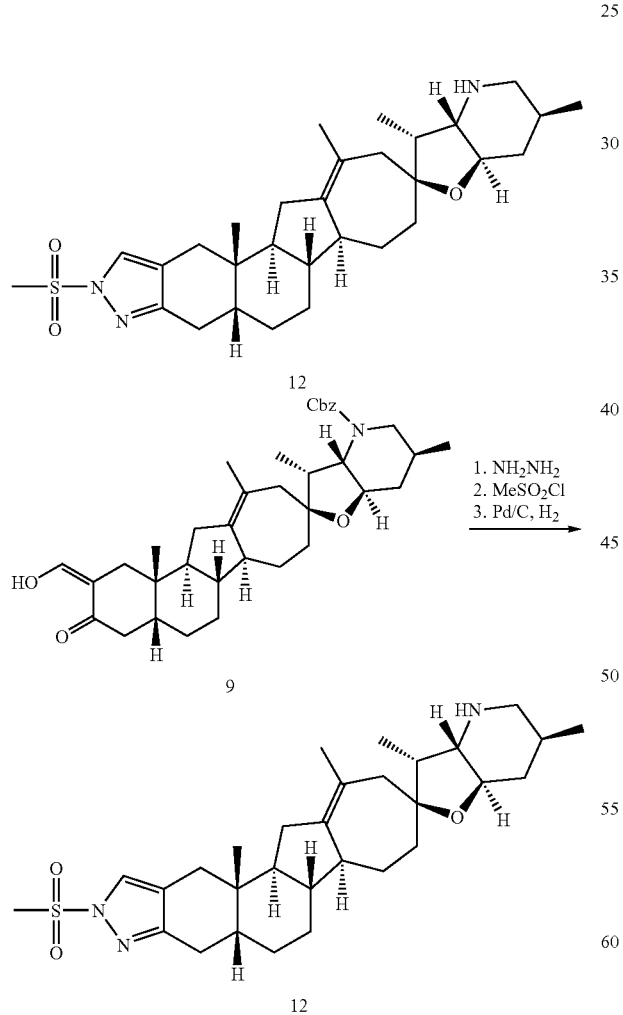

An ethanol solution (4 mL) of compound 9 (100.0 mg, 0.17 mmol, 1.0 eq) was treated with hydrazine (16 mg, 0.34 mmol, 2.0 eq) and heated at 70° C. for 0.5 h. The mixture was concentrated in vacuo and was purified by flash silica gel chromatography (20→60% ether/hexanes) to give the protected pyrazole as a white solid (72.0 mg).

The Cbz-protected pyrazole (200 mg, 0.34 mmol, 1.0 eq) was dissolved in pyridine (4 mL) and treated with methanesulfonyl chloride (117 mg, 1.03 mmol, 3 eq) with stirring at rt. After 30 min the mixture was partitioned between EtOAc (40 mL) and water (20 mL). The organic layer was washed with brine (20 mL), dried over sodium sulfate, and concentrated in vacuo. The resultant oil was purified by silica gel chromatography (10→20% EtOAc/hexanes) to give a clear oil (150 mg).

The methanesulfonyl pyrazole was dissolved in EtOAc (15 mL) in a flask with stir bar and rubber septum. The solution was sparged with nitrogen, and 10% Pd/C (wet, Degussa type E101, Aldrich, 50 mg) was added. This mixture was sparged with nitrogen and then hydrogen gas and stirred at rt for 2 h. The mixture was then sparged with nitrogen, filtered through a 0.45 μm polyethylene membrane and concentrated to a clear oil. The oil was purified by flash silica gel chromatography (0.5% ammonium hydroxide/2→10% MeOH/DCM), and the pure fractions were concentrated to give an oil that was lyophilized from 7% water/t-butanol, affording the desired product as a white powder (78 mg: [M+H]=528.8 m/z).

Example 5

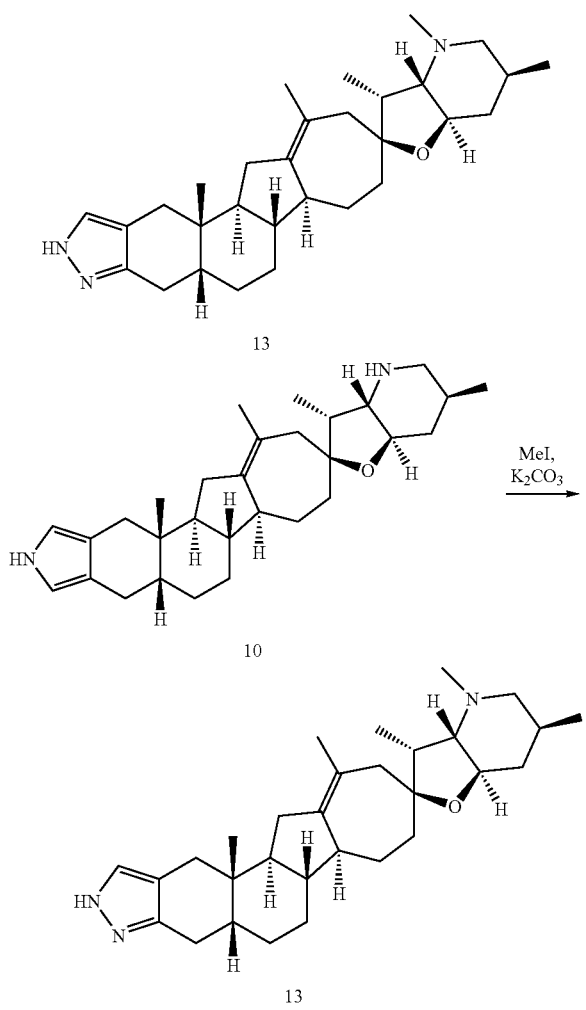

Compound 10 (60 mg, 0.13 mmol, 1.0 eq) was dissolved in DCM (1 mL) with MeI (38 mg, 0.27 mmol, 2 eq) and stirred vigorously with potassium carbonate (74 mg, 0.53 mmol, 4.0 eq) at rt. After stirring for 1 h, the mixture was partitioned between DCM (20 mL) and water, and the aqueous layer was extracted with a second portion of DCM (20 mL). The combined organic layers were washed with brine (20 mL), dried over sodium sulfate, and concentrated in vacuo. The resultant oil was purified by silica gel flash chromatography (0.5% ammonium hydroxide/1→6% MeOH/DCM), and the pure fractions were concentrated to give an oil that was lyophilized from 7% water/t-butanol, affording the desired product as a white powder (18 mg: [M+H]=464.6 m/z).

Example 6

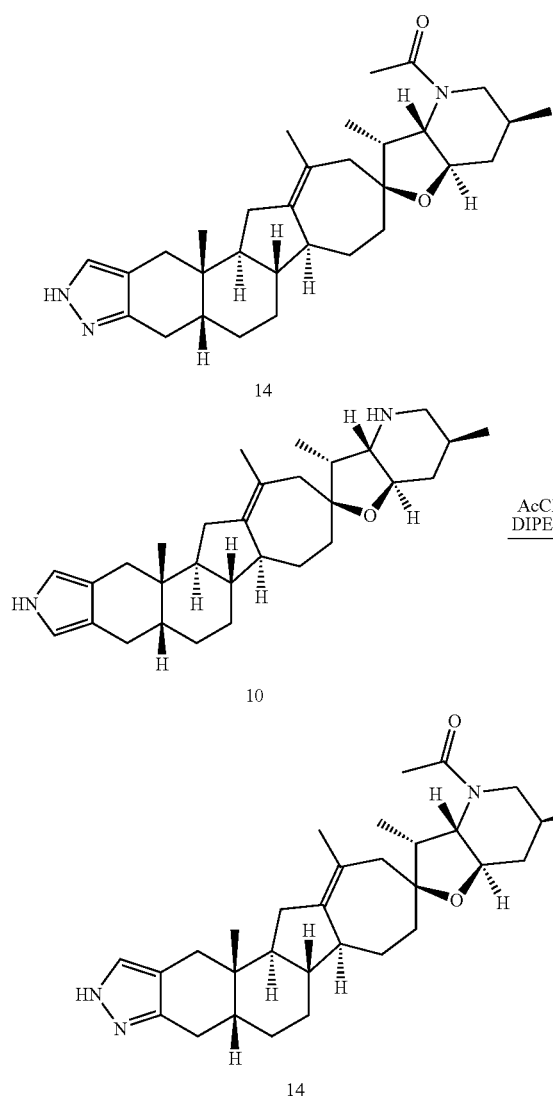

Compound 10 (80.0 mg, 0.19 mmol, 1.0 eq) was dissolved in dry DCM (2 mL) with diisopropylethylamine (115 mg, 0.9 mmol, 5 eq) and treated with acetyl chloride (42 mg, 0.54 mmol, 3 eq). After stirring for 30 min at rt, the mixture was concentrated in vacuo. The resulting residue was restored in 1:1 THF/MeOH (5 mL) and treated with ammonium hydroxide (0.5 mL) with stirring for 1.5 h. This mixture was concentrated in vacuo and purified by silica gel flash chromatography (0.5% ammonium hydroxide/1→8% MeOH/DCM) to give a clear oil that was lyophilized from 7% water/t-butanol to afford the desired product as a white powder (14 mg: [M+H]=492.5 m/z).

Example 7

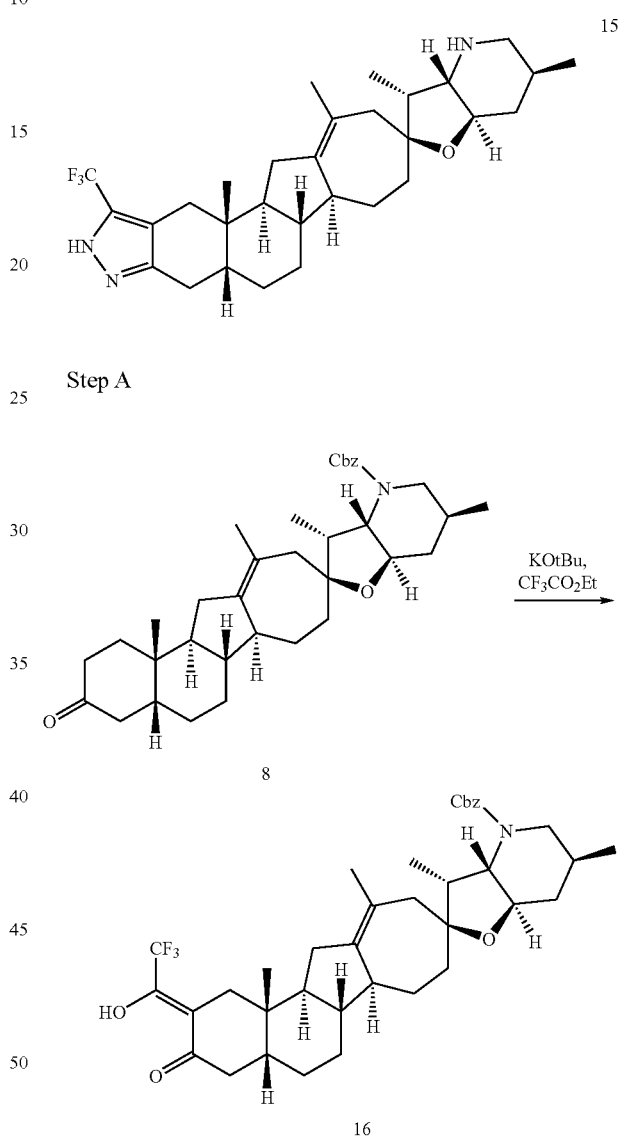

Step A

A dry round-bottom flask was charged with KOtBu (0.70 g, 6.3 mmol, 7 eq) and tBuOH (10 mL) and the solution was stirred at rt for 10 min. Compound 8 (0.5 g, 0.89 mmol, 1 eq) was added and stirred for 5 min. Ethyl trifluoroacetate (0.64 ml, 5.4 mmol, 6 eq) was added dropwise, and the solution became slightly opaque and produced bubbles. The slurry was stirred at rt for 48 h. The mixture was diluted with DCM (40 mL) and washed with water (2×30 mL). The organic layer was washed with brine (20 mL), dried over Na₂SO₄, and concentrated to dryness to give 550 mg of a pale orange foam. This material was used in the next step without further purification.

Step B

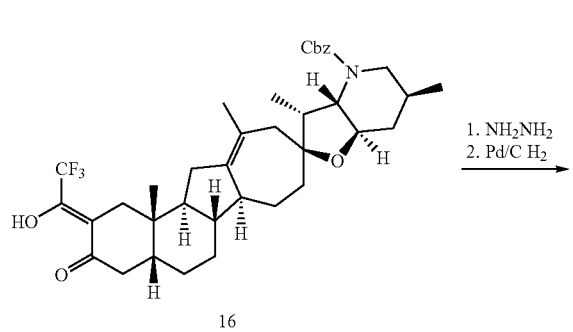

16

1. NH₂NH₂
2. Pd/C H₂
→

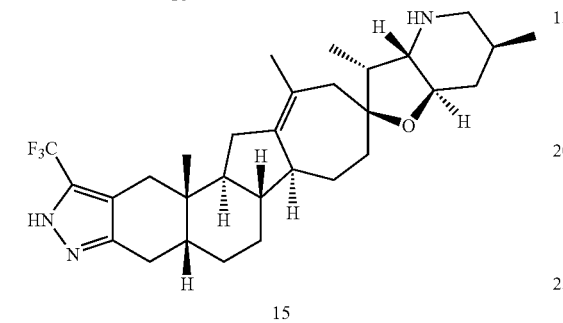

15

An ethanol solution (4 mL) of compound 16 (210 mg, 0.32 mmol, 1.0 eq) was treated with hydrazine (32 mg, 0.64 mmol, 2.0 eq) and heated at 80° C. for 1.5 h. The solution was concentrated in vacuo and purified by silica gel flash chromatography (20→55% EtOAc/hexanes) to give the 3-trifluoromethyl pyrazole as a white solid (95.0 mg).

The product carbamate pyrazole was dissolved in EtOAc (7 mL) in a flask with stir bar and rubber septum. The solution was sparged with nitrogen, and 10% Pd/C (wet, Degussa type E101, Aldrich, 25 mg) was added. This mixture was sparged with nitrogen and then hydrogen gas and stirred at rt for 2 h. The mixture was then sparged with nitrogen, filtered through a 0.45 μm polyethylene membrane and concentrated to a clear oil. The oil was purified by silica gel flash chromatography (0.5% ammonium hydroxide/2→14% MeOH/DCM), and the pure fractions were concentrated to give an oil that was lyophilized from 7% water/t-butanol to afford the desired product as a white powder (42 mg: [M+H]=518.8 m/z).

Example 8

Step A

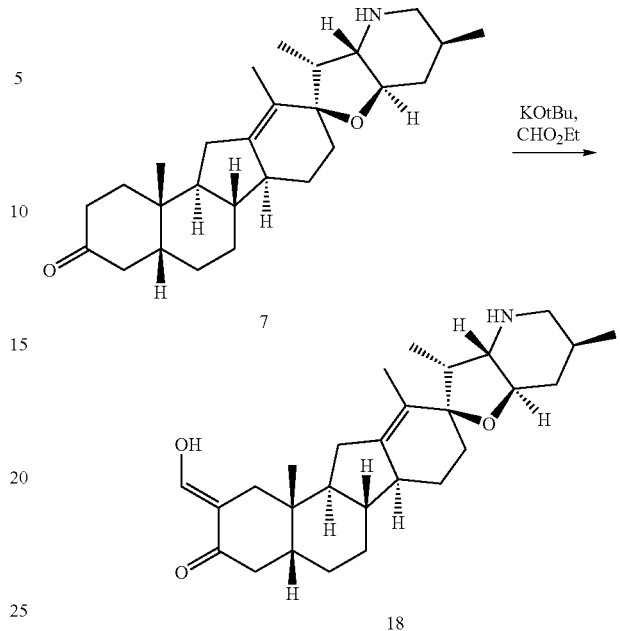

A dry round-bottom flask was charged with KOtBu (0.57 g, 5.1 mmol, 7 eq) and tBuOH (6 mL) and the solution was stirred at rt for 10 min. Compound 7 (0.3 g, 0.73 mmol, 1 eq) was added and stirred for 5 min. Ethyl formate (0.35 mL, 4.4 mmol, 6 eq) was added dropwise, and the solution became slightly opaque and produced bubbles. The slurry was stirred at rt for 48 h. The mixture was portioned between MTBE/1% NaOH (2×20 mL). The aqueous layer was acidified with 2 N HCl until the pH was 5, then extracted with chloroform (2×). The combined organic layers were washed with water, dried over Na₂SO₄, and concentrated to dryness to give 200 mg of a pale yellow foam. This material was used without further purification.

Step B

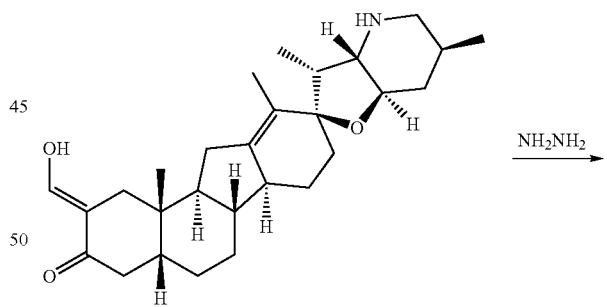

18

NH₂NH₂
→

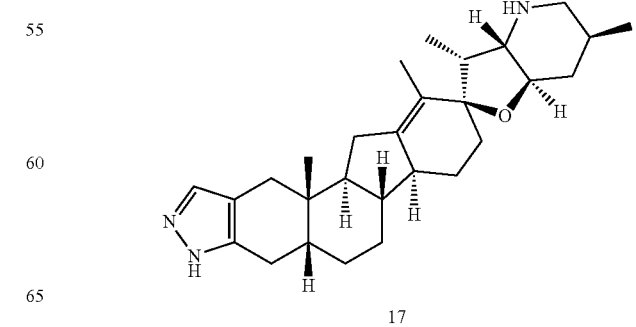

17

A round-bottom flask was charged with compound 18 (195 mg, 0.44 mmol, 1 eq). The material was dissolved in EtOH (3 mL) and hydrazine (43 µL, 0.89 mmol, 2 eq) was added. The resulting mixture was heated to reflux. After 1 h the solution was cooled to rt. Solids crashed from solution, which were filtered, washed with heptane, and dried to afford 19 mg of the desired material ([M+H]=436.4 m/z).

Example 9

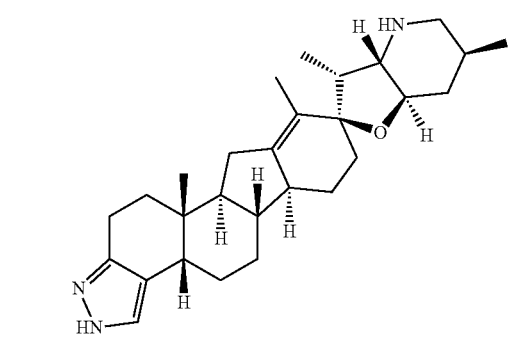

Step A

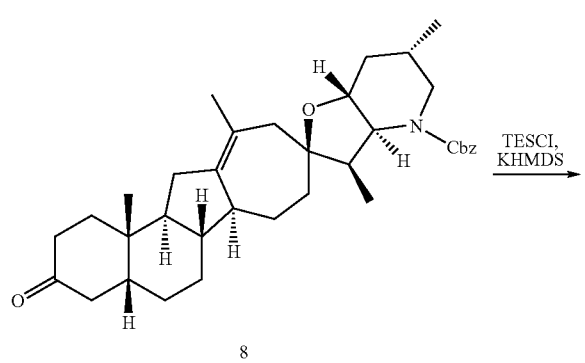

8

TESCl,
KHMDS
→

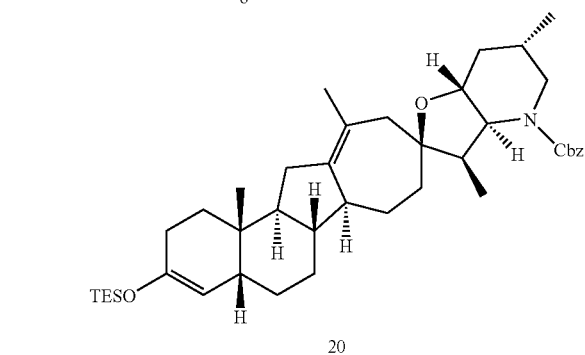

20

A round-bottom flask was charged with potassium bis(trimethylsilyl)amide (580 mg, 1.04 mmol, 1 eq) and was dissolved in anhydrous THF (12 mL). The reaction mixture was cooled to −74° C. The reaction was charged with compound 8 (310 mg, 1.55 mmol, 1.5 eq). The mixture was stirred for 0.5 h and chlorotriethylsilane (234 mg, 1.55 mmol, 1.5 eq) in anhydrous THF (2 mL). The reaction mixture was stirred for 0.5 h and charged with water (10 mL). The reaction mixture was warmed to rt and extracted with EtOAc. The organic was separated, dried and concentrated to dryness. The residue was purified using silica gel flash chromatography (EtOAc/hexanes 2%→6%) to afford the desired material.

Step B

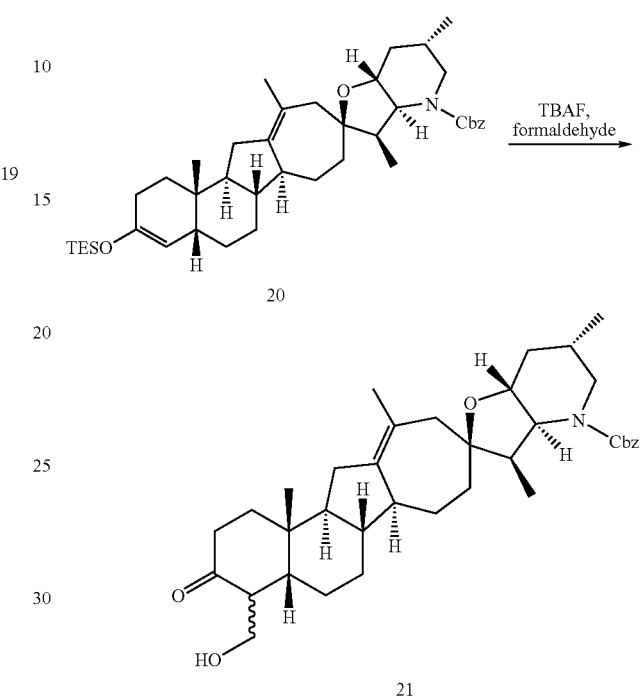

A round-bottom flask was charged with a 37% aqueous formaldehyde solution (329 mg, 4.05 mmol, 5 eq) and diluted in THF (10 mL). The reaction was cooled to −20° C. charged with a solution of starting material (546 mg, 0.810 mmol, 1 eq) in THF (2 mL) and 1 M tetrabutylammonium fluoride in THF (1.06 g, 4.05 mmol, 5 eq). The mixture was stirred for 0.5 h at −20° C. and partitioned between brine and EtOAc. The organic layer was separated, dried and concentrated in vacuo. The residue was purified using silica gel flash chromatography (EtOAc/hexanes 10%→20%) to afford the desired material.

Step C

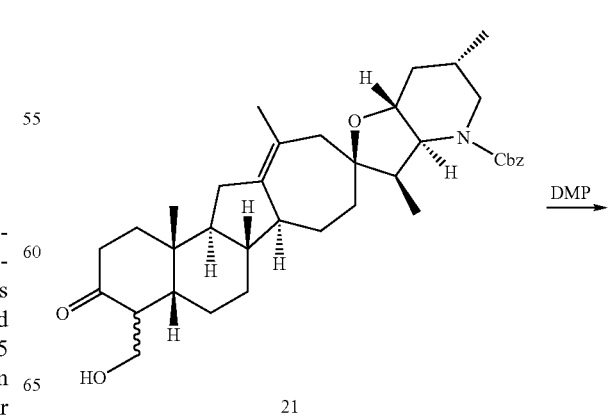

21

-continued

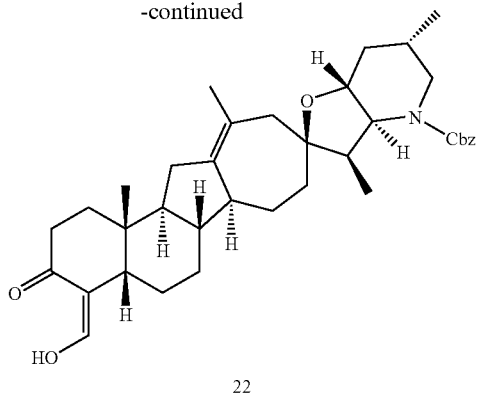

22

A round-bottom flask was charged with compound 21 (100 mg, 0.169 mmol, 1 eq) and was dissolved in of DCM (5 mL). The reaction was cooled to 0° C. and charged with Dess-Martin periodinane (144 mg, 0.339 mmol, 2 eq). The mixture was stirred for 0.5 h at 0° C. The reaction mixture was partitioned between a saturated aqueous solution of sodium bicarbonate and EtOAc. The organic was separated, dried and concentrated in vacuo. The residue was purified using silica gel flash chromatography (EtOAc/hexanes 5%→10%) to afford the desired material.

Step D

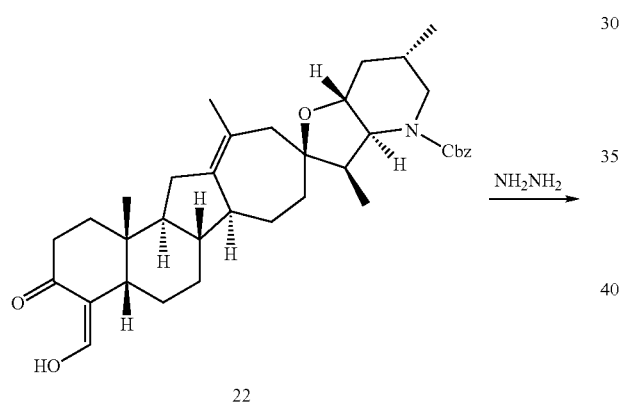

22

23

A round-bottom flask was charged with compound 22 (50 mg, 0.085 mmol, 1 eq) and was dissolved in of EtOH (3 mL). The reaction was charged with hydrazine (27 mg, 0.851 mmol, 10 eq). The mixture was heated to 80° C. and stirred. After 0.5 h, the reaction mixture was concentrated in vacuo. The residue was purified using silica gel flash chromatography (EtOAc/hexanes 50%) to afford the desired material.

Step E

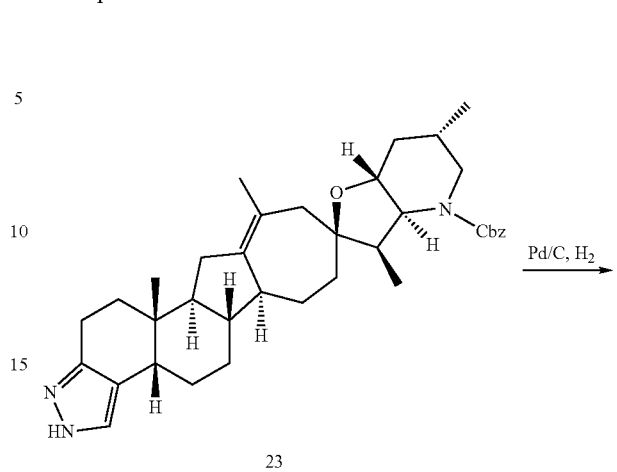

23

19

A round-bottom flask was charged with compound 23 (43 mg, 0.074 mmol, 1 eq) and 10% palladium on carbon (8 mg). The solids were suspended in EtOAc (3 mL). The suspension was placed under hydrogen atmosphere and the mixture was stirred for 20 h at rt. The reaction mixture was filtered and the filtrate concentrated in vacuo. The residue was purified using silica gel flash chromatography (MeOH/DCM 0%→5%) to afford the desired material. ([M+H]=450.5 m/z).

Example 10

Step A

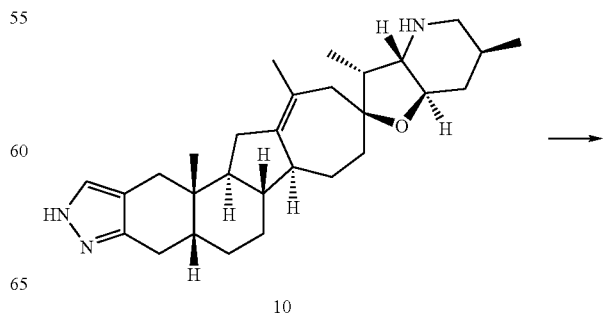

10

-continued

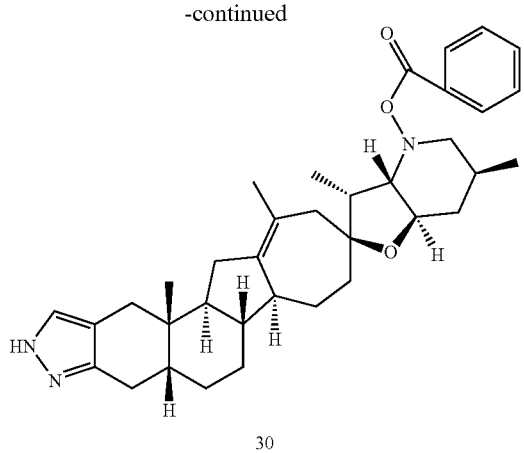

30

To a solution of Compound 10 (72 mg, 0.16 mmol, 1 eq) in chloroform (1.4 ml) at room temp, was added pyridine (215 mg, 2.72 mmol, 17 eq). The resultant mixture was cooled to 0° C. and treated with benzoyl peroxide (388 mg, 1.60 mmol, 10 eq). The mixture was stirred for 1.5 hours and allowed to warm to room temp. The reaction mixture was diluted with water (10 ml) and pH adjusted to 7~8 with saturated sodium bicarbonate followed by extraction with chloroform (2×15 ml), the combined organic layers were dried over $Na_2SO_4$, filtered and dried in vacuo. The residue was purified by flash chromatography (Dichloromethane/Methanol 97:3). The target Compound 30 was obtained (26 mg, 0.046 mmol, ~30% yield).

Step B

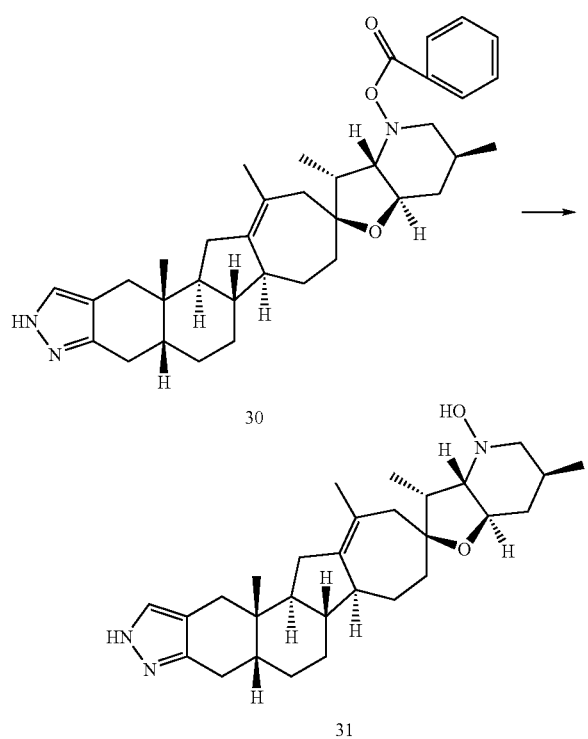

A solution of Compound 30 (26 mg, 0.046 mmol, 1 eq) in methanol (0.8 ml) at room temp was treated with 2N Potassium Hydroxide (19 mg, 0.342 mmol, 7.5 eq). The resulting solution was stirred for 2 hours. The reaction mixture was diluted with water (10 ml) and pH adjusted to 6~7 with 1N HCl followed by extraction with chloroform (3×10 ml), the combined organic layers dried over $Na_2SO_4$ and in vacuo. The residue was purified by preparative TLC (chloroform/methanol 90:10). The desired fractions wee frozen and lyophilized to yield Compound 31 as a white powder (11 mg, 0.024 mmol, ~52% yield).

Example 11

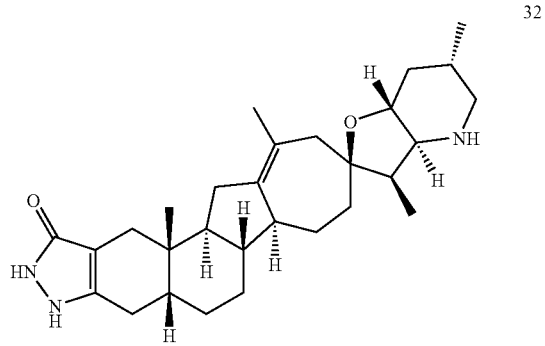

Step A

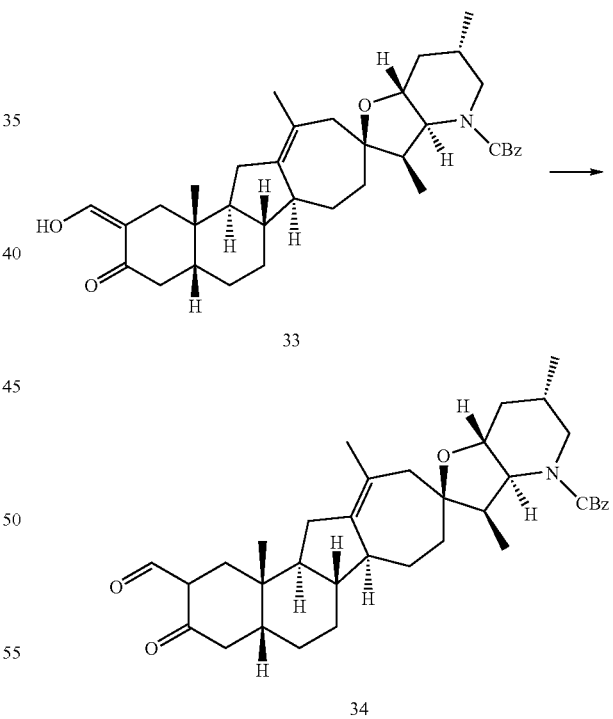

A round-bottom flask was charged with compound 33 (2.0 g, 3.40 mmol, 1 equiv.) and was dissolved in toluene (25 mL). The reaction was charged with DDQ (0.849 g, 3.74 mmol, 1.1 eq). The mixture was stirred for 0.5 hr at rt. The reaction mixture was then concentrated in vacuo to 10% the original volume. The residue was purified using silica gel flash chromatography (hexanes/EtOAc 10%→20%) to afford the desired material 34.

Step B

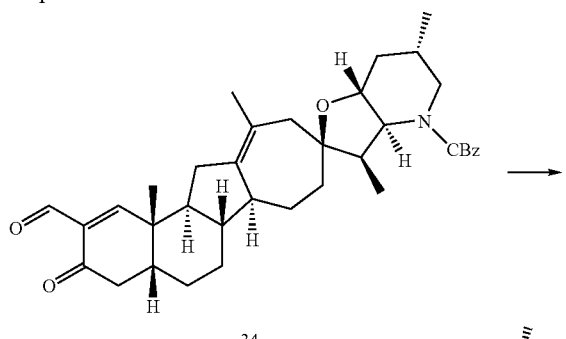

34

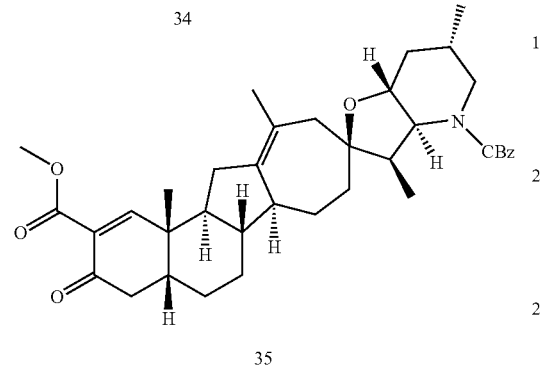

35

A round-bottom flask was charged with 34 (123 mg, 0.21 mmol, 1 equiv.), DMF (3 mL) and MeOH (8.5 µL, 2.1 mmol, 10 equiv.). To this solution was added pyridinium dichromate (424 mg, 1.2 mmol, 6 equiv.). The slurry was stirred for 4 days at 25° C. The mixture was diluted with EtOAc and water. The mixture was filtered through a pad of celite, rinsed with EtOAc, then the layers were cut. The aqueous layer was extracted with one portion of EtOAc. Combined organic layers were washed with 1 N HCl, dried over $Na_2SO_4$, filtered, and concentrated to dryness. The crude material (232 mg) was dissolved with $CH_2Cl_2$, loaded onto a $SiO_2$ column (6 g) and eluted with hexanes/EtOAc (20%) to give the desired ester 35 (36 mg).

Step C

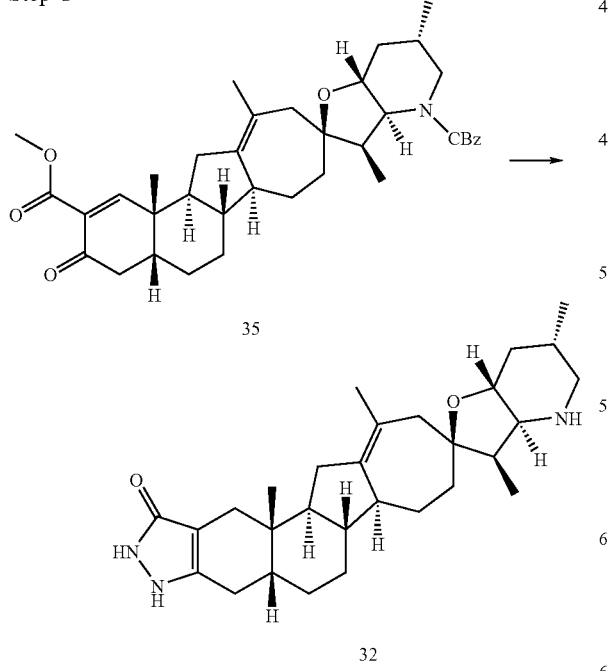

A round-bottom flask was charged with 35 (35 mg, 0.057 mmol, 1 equiv.) and 3 mg of 10% Pd/C (wet, Aldrich Degussa type E101). The material was suspended in EtOH (3 mL). The flask was sealed and purged three times with hydrogen and left overnight under 1 atm of hydrogen. The slurry was filtered through 0.2 micron Acrodisc and washed with EtOH. The solvent was concentrated to ~3 mL under vacuum. To the ethanolic solution of deprotecting intermediate was added hydrazine hydrate (10 uL, 0.22 mmol, 4 equiv.) and the mixture was heated to 70° C. for 4 h. The product was precipitated out of the reaction by chases with 2-propanol, then heptane. The residue was purified by $SiO_2$ column (1 g) eluting with $CH_2Cl_2$/MeOH (10%). The major product was lyophilized from t-BuOH/7% $H_2O$ to give 15 mg of pyrazolone 32 ([M+H]=466.5 m/z).

Compounds 40-45 were made using techniques similar to those described above.

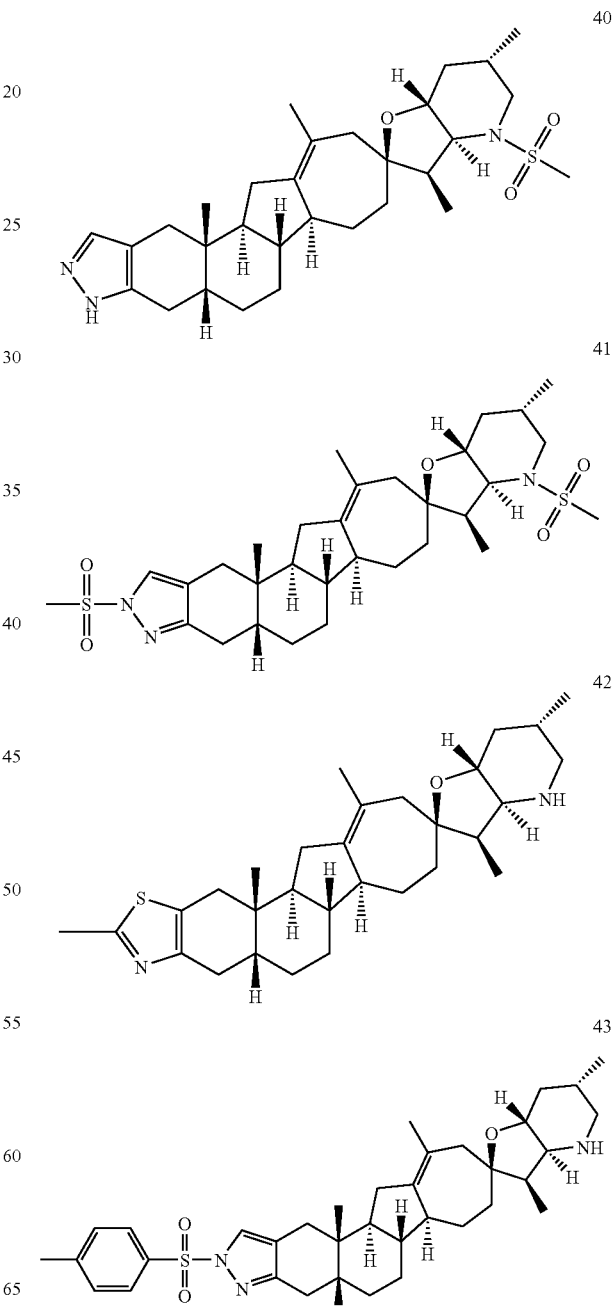

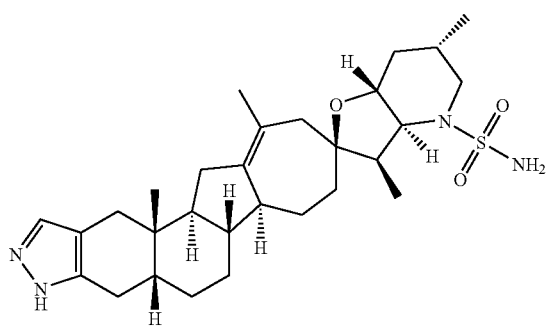

44

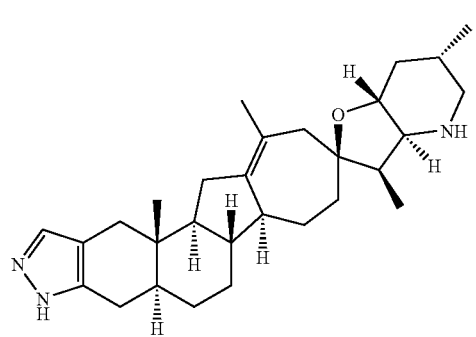

Example 12

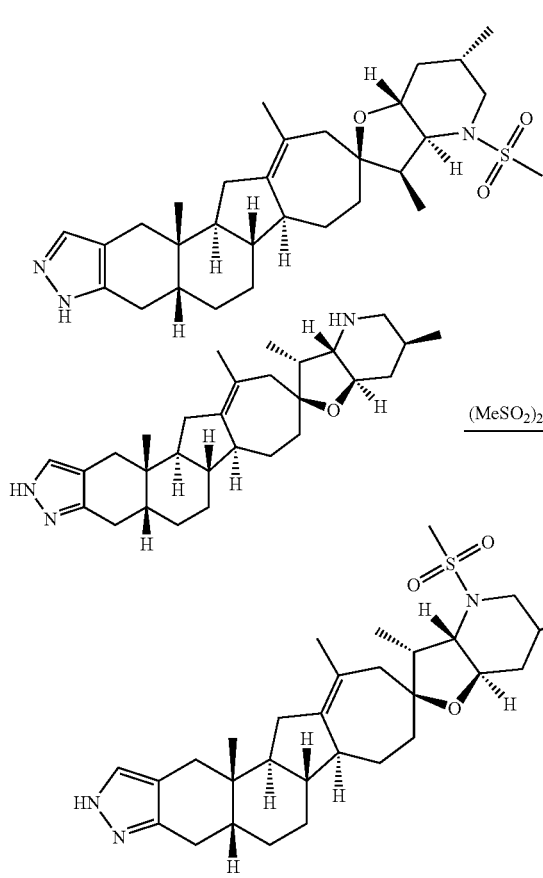

The starting material (50.0 mg) was suspended in DCM (1.5 ml) and stirred vigorously with sodium bicarbonate (28 mg, 0.33 mmol, 3 equiv) in water (0.50 ml). The mixture was treated with methanesulfonic anhydride (28 mg, 0.11 mmol, 1 equiv) and stirred for 15 minutes at room temperature. The mixture was split between ethyl acetate and water, and the organic layer was then washed with brine and dried over sodium sulfate. The residue obtained upon concentration was purified by flash silica gel chromatography (50→100% ethyl acetate/hexanes) to provide a white solid, Compound 40 (10 mg: [M+H]=528.1 m/z).

Example 13

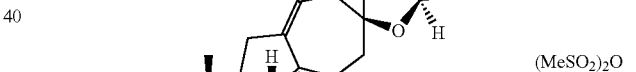

41

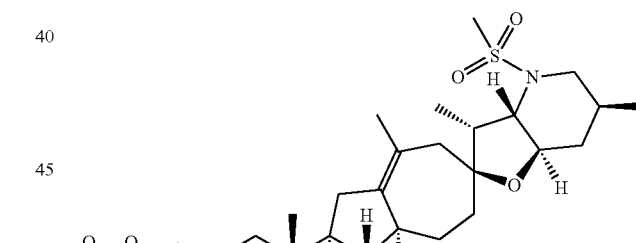

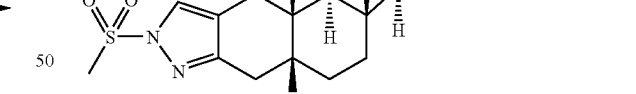

The starting material (100.0 mg, 0.22 mmol, 1 equiv) was suspended in DCM (3.0 ml) and stirred with pyridine (88 mg, 1.1 mmol, 5 equiv). The mixture was treated with methanesulfonic anhydride (97 mg, 0.55 mmol, 2.5 equiv) and stirred for 15 minutes at room temperature. The mixture was split between ethyl acetate and water, and the organic layer was then washed with brine and dried over sodium sulfate. The residue obtained upon concentration was purified by flash silica gel chromatography (20→50% ethyl acetate/hexanes) to provide a white solid, Compound 41 (50 mg: [M+H]=606.1 m/z).

Example 14

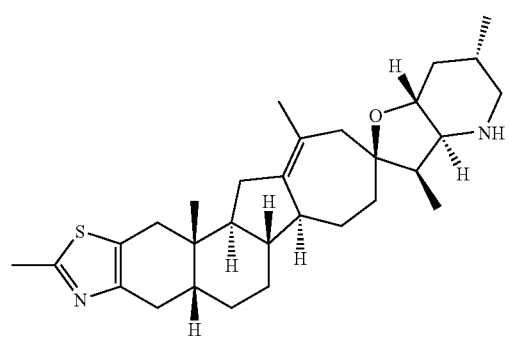

42

Step A

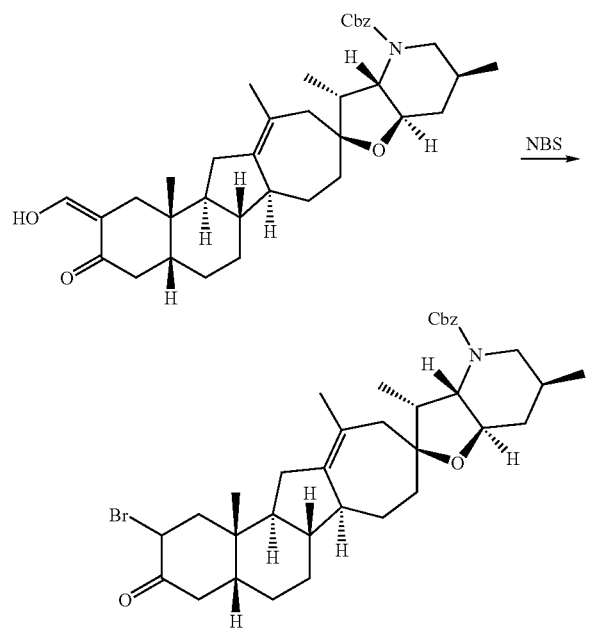

A mixture of the starting material (300 mg, 0.51 mmol, 1 equiv), sodium acetate (42 mg, 0.51 mmol, 1 equiv), and acetic acid (30 mg, 0.51 mmol, 1 equiv) suspended in 10:1 dioxane/water (25 ml) was treated with N-bromosuccinimide (95 mg, 5.4 mmol, 1.05 equiv) and stirred at room temperature for 14 hours. The mixture was split between ethyl acetate and water, and the organic layer was then washed with brine and dried over sodium sulfate. The residue obtained upon concentration was purified by flash silica gel chromatography (5→30% ethyl acetate/hexanes) to provide a clear oil as a mixture of bromoketone isomers (62 mg).

Step B

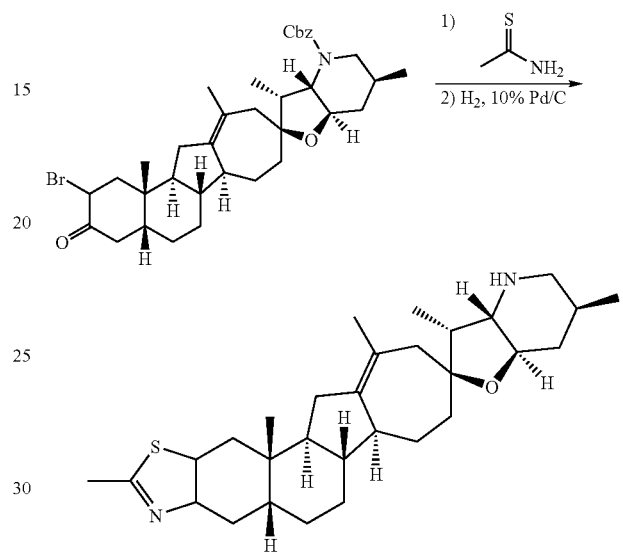

This bromoketone mixture was dissolved in ethanol (1 ml) and heated at reflux with thioacetamide (33 mg, 0.44 mmol, 4.6 equiv) for 3 hours. The mixture was split between ethyl acetate and water, and the organic layer was then washed with brine and dried over sodium sulfate. The residue obtained upon concentration was purified by flash silica gel chromatography (5→35% ethyl acetate/hexanes) to provide a white solid (35 mg). This material was dissolved in ethanol (4 ml) and stirred under a hydrogen atmosphere with 20 mg of 10% Pd/C (wet Degussa type) for 1.5 hours at room temperature. The mixture was filtered and its concentrated residue purified by silica gel chromatography (0.5% NH$_4$OH/1→10% methanol/dichloromethane) to give a clear oil, Compound 42 (16 mg: [M+H]=481.1 m/z).

Example 15

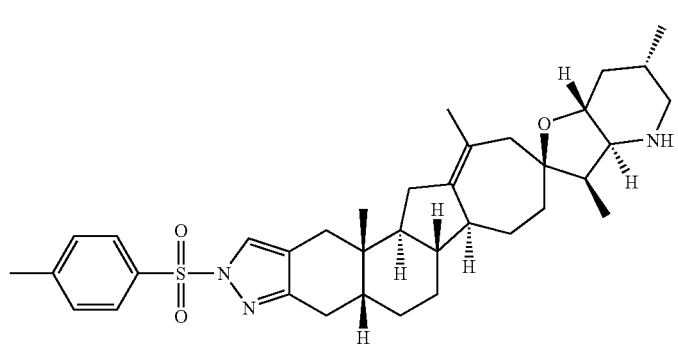

43

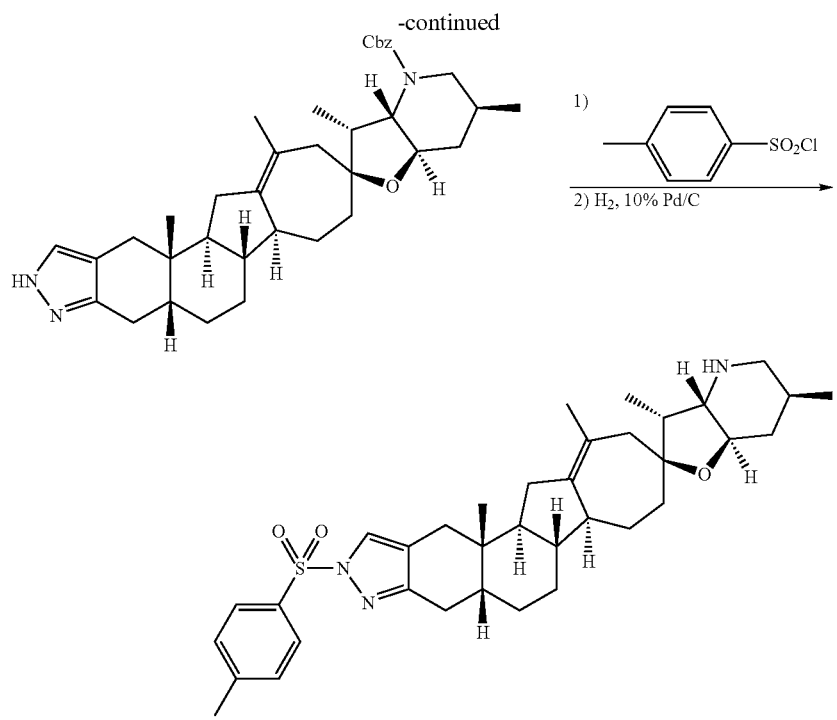

The starting material (140.0 mg, 0.24 mmol, 1 equiv) was suspended in DCM (3.0 ml) and stirred with pyridine (95 mg, 1.2 mmol, 5 equiv). The mixture was treated with toluenesulfonyl chloride (54 mg, 0.288 mmol, 1.2 equiv) and stirred for 2 hours at room temperature. The mixture was split between ethyl acetate and water, and the organic layer was then washed with brine and dried over sodium sulfate. The residue obtained upon concentration was purified by flash silica gel chromatography (5→30% ethyl acetate/hexanes) to provide a white solid. This material was dissolved in 1:1 ethanol/ethyl acetate (4 ml) and stirred under a hydrogen atmosphere with 30 mg of 10% Pd/C (wet Degussa type) for 1.5 hours at room temperature. The mixture was filtered and its concentrated residue purified by silica gel chromatography (0.5% NH₄OH/1→14% methanol/dichloromethane) to give a clear oil, Compound 43 (64 mg: [M+H]=604.1 m/z).

Example 16

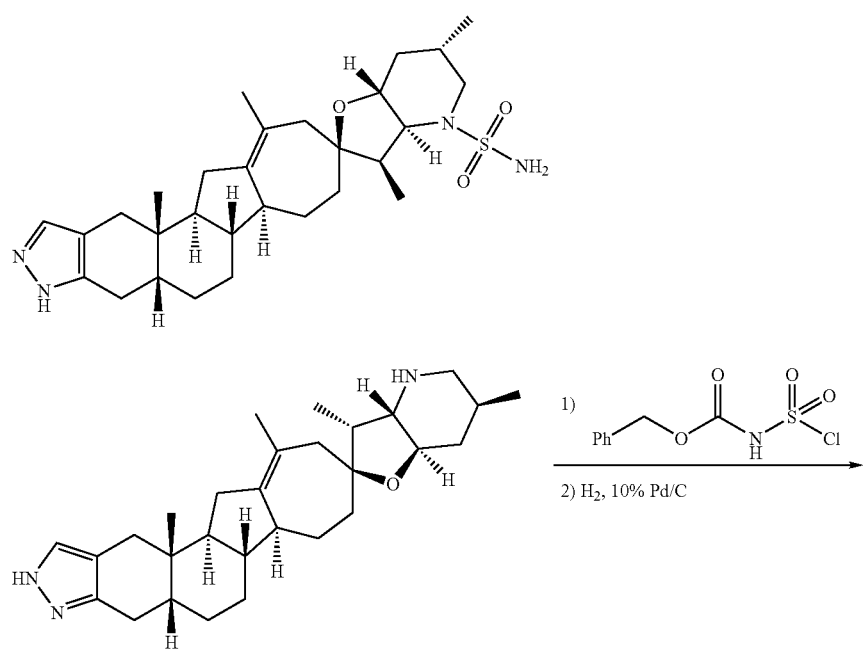

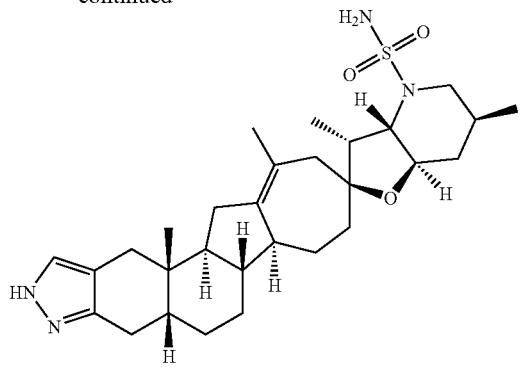

In dry dichloromethane (7 ml) at 0 C, chlorosulfonyl isocyanate (1.0 g, 7.06 mmol, 1 equiv) and benzyl alcohol (764 mg, 7.06 mmol, 1 equiv) were stirred for 30 min to form a 1M solution of Cbz-sulfamoyl chloride. In a separate flask, the starting material (100.0 mg, 0.22 mmol, 1 equiv) was dissolved in DCM (3.0 ml) with pyridine (88 mg, 1.1 mmol, 5 equiv) was treated with the Cbz-sulfamoyl chloride (0.55 ml, mmol, 2.5 equiv) and stirred for 5 min at room temperature. The mixture was split between ethyl acetate and water, and the organic layer was then washed with brine and dried over sodium sulfate. The residue obtained upon concentration was purified by flash silica gel chromatography (0.25% acetic acid/80→100% ethyl acetate/hexanes) to provide a white solid. This material was dissolved in 1:1 ethanol/ethyl acetate (4 ml) with 0.25% acetic acid, and was stirred under a hydrogen atmosphere with 25 mg of 10% Pd/C (wet Degussa type) for 1 hour at room temperature. The mixture was filtered and its concentrated residue purified by silica gel chromatography (0.25% acetic acid/80→100% ethyl acetate/hexanes) to give a clear white solid, Compound 44 (32 mg: 529.1 [M+H]=m/z).

Example 17

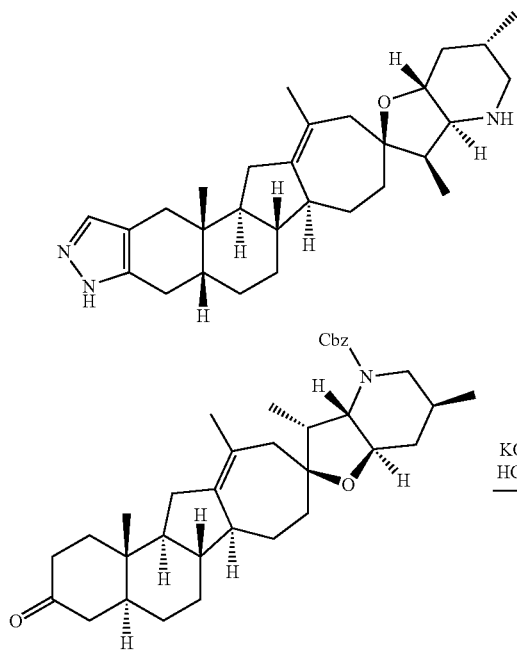

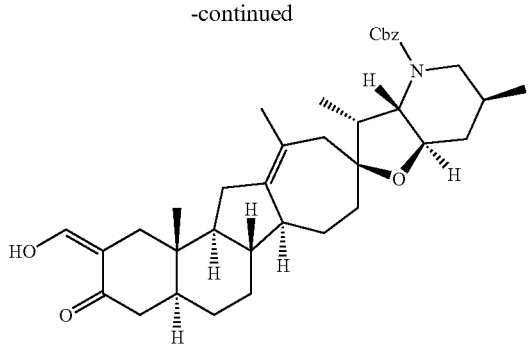

A dry round-bottom flask was charged with KOtBu (0.49 g, 4.4 mmol, 7 eq) and tBuOH (5 mL) and the solution was stirred at rt for 10 min. The starting material (0.349 g, 0.623 mmol, 1 eq) was added and stirred for 5 min. The white suspension became a yellow clear solution. Ethyl formate (0.30 mL, 3.75 mmol, 6 eq) was added dropwise, and the solution became slightly opaque and produced bubbles. The slurry was stirred at rt for 48 h. The mixture was then portioned between MTBE/1% aqueous sodium hydroxide (2×20 mL). The aqueous layer was acidified with 2 N HCl until the pH reached 5, and then extracted twice with chloroform. The combined organic layers were washed with water, dried over Na$_2$SO$_4$, and concentrated to dryness to give 200 mg pale yellow foam. This material was used without further purification in the next step.

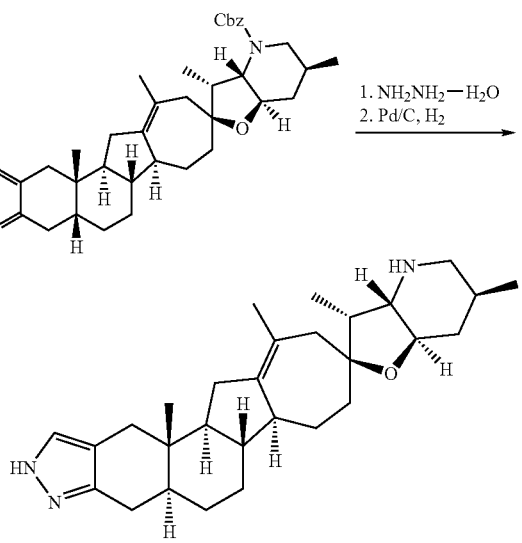

An ethanol solution (4 mL) of the 2-formylketone (262 mg, 0.45 mmol, 1.0 eq) was treated with hydrazine hydrate (50 mg, 0.90 mmol, 2.0 eq) and heated at 80° C. for 0.5 h. The mixture was concentrated in vacua and was purified by flash silica gel chromatography (20→60% ethyl acetate/hexanes) to give the protected pyrazole as a white solid (151 mg). The intermediate carbamate was dissolved in 1:1 ethanol/ethyl acetate (4 mL) in a flask with stir bar and rubber septum. The solution was sparged with nitrogen, and 10% Pd/C (wet, Degussa type E101, Aldrich, 30 mg) was added. This mixture was sparged with nitrogen and then hydrogen gas and stirred at room temperature for 2 h. The mixture was filtered and concentrated to a clear oil which was purified by flash silica gel chromatography (0.5% ammonium hydroxide/1→10% methanol/dichloromethane) to give an oil that was lyophilized from 7% water/tBuOH, to afford the desired product, Compound 45, as a white powder (108.8 mg: 450.1 [M+H]= m/z).

Example 18

Inhibition of the Hedgehog Pathway in Cell Culture Using Analogs of Steroidal Alkaloids Hedgehog pathway specific cancer cell killing effects may be ascertained using the following assay. C3H10T1/2 cells differentiate into osteoblasts when contacted with the sonic hedgehog peptide (Shh-N). Upon differentiation, these osteoblasts produce high levels of alkaline phosphatase (AP) which can be measured in an enzymatic assay (Nakamura, et al., *BBRC* (1997) 237:465). Compounds that block the differentiation of C3H10T1/2 into osteoblasts (a Shh dependent event) can therefore be identified by a reduction in AP production (van der Horst, et al., *Bone* (2003) 33:899). The assay details are described below. The results approximate ($EC_{50}$ for inhibition) of the differentiation assay is shown below in Table 1.

Cell Culture

Mouse embryonic mesoderm fibroblasts C3H10T1/2 cells (obtained from ATCC) were cultured in Basal MEM Media (Gibco/Invitrogen) supplemented with 10% heat inactivated FBS (Hyclone), 50 units/ml penicillin and 50 ug/ml streptomycin (Gibco/Invitrogen) at 37° C. with 5% $CO_2$ in air atmosphere.

Alkaline Phosphatase Assay

C3H10T1/2 cells were plated in 96 wells with a density of $8 \times 10^3$ cells/well. Cells were grown to confluence (72 hrs). After sonic Hedgehog (250 ng/ml), and/or compound treatment, the cells were lysed in 110 µL of lysis buffer (50 mM Tris pH 7.4, 0.1% Triton×100), plates were sonicated and lysates spun through 0.2 µm PVDF plates (Corning). 40 µL of lysates was assayed for AP activity in alkaline buffer solution (Sigma) containing 1 mg/ml p-Nitrophenyl Phosphate. After incubating for 30 min at 37° C., the plates were read on an Envision plate reader at 405 nm. Total protein was quantified with a BCA protein assay kit from Pierce according to manufacturer's instructions. AP activity was normalized against total protein. "A" indicates that the $IC_{50}$ is less than 20 nM, "B" indicates that the $IC_{50}$ is 20-100 nM, "C" indicates that the $IC_{50}$ is >100 nM.

TABLE 1

| Compound | Approximate $EC_{50}$ for Inhibition Differentiation Assay $EC_{50}$ |
|---|---|
| 1 | B |
| 10 | A |
| 11 | B |

TABLE 1-continued

| Compound | Approximate $EC_{50}$ for Inhibition Differentiation Assay $EC_{50}$ |
|---|---|
| 12 | C |
| 13 | B |
| 14 | B |
| 15 | C |
| 17 | B |
| 19 | C |
| 31 | B |
| 32 | C |
| 40 | B |
| 41 | C |
| 42 | C |
| 43 | C |
| 44 | B |
| 45 | C |

Example 19

Pancreatic Cancer Model

The activity of Compound 10 was further tested in a human pancreatic model: BxPC-3 cells were implanted subcutaneously into the flanks of the right legs of mice. On day 42 post-tumor implant, the mice were randomized into two groups to receive either Vehicle (30% HPBCD) or Compound 10. Compound 10 was administered orally at 40 mg/kg/day. After receiving 25 daily doses, Compound 10 statistically reduced tumor volume growth by 37% when compared to the vehicle control (p=0.0437). At the end of the study, the tumors were harvested 4 hours post the last dose to evaluate an on target response by q-RT-PCR analysis of the HH pathway genes. Analysis of human Gli-1 resulted in no modulation. Analysis of murine Gli-1 mRNA levels resulted in a robust down-regulation in the Compound treated group, when compared to the Vehicle treated group.

The activity of Compound 10 was also tested in another model of pancreatic cancer in which the PANC-1 pancreatic cancer cells were implanted into the orthotopic site, that is, directly into the pancreas. At the end of 5 weeks of dosing, 40 mg/kg/day (a total of 35 doses), tumor growth was monitored by weighing the tumors as they were removed from the animals. There was a statistically significant (p=0.00014) difference between the Compound 10 and vehicle treated animals which was seen as a 47% decrease in tumor weight in the Compound 10 treated animals. In addition, tumor tissue was harvested and RNA was isolated 24 hours after the final dose of Compound 10. A similar result was seen for the PANC-1 cells as was seen for BxPC-3. Analysis of human Gli-1 mRNA revealed no modulation, while analysis of murine Gli-1 did reveal modulation. These data reveal that inhibition of the hedgehog pathway in mouse cells, but not human tumor cells, suggesting that one effect of the hedgehog pathway inhibitor is to affect a tumor-stroma interaction.

Example 20

Medulloblastoma Model

The activity of Compound 10 was evaluated in a transgenic mouse model of medulloblastoma. Mice that are heterozygous for loss of function mutations in the tumor suppressors Patched1 (Ptch1) and Hypermethylated in Cancer (Hic1) develop spontaneous medulloblastoma. Similar to human medulloblastoma, these tumors demonstrate complete promoter hypermethylation of the remaining Hic1 allele, as well as loss of expression of the wild type Ptch1 allele. When passaged as subcutaneous allografts, these tumors grow aggressively and are Hedgehog pathway-dependent. This model was employed to evaluate the efficacy of orally administered Compound, and to correlate activity with drug exposure in plasma and tumors. Oral administration (PO) of a single dose of Compound 10 led to dose-dependent down-regulation of the HH pathway in subcutaneously implanted tumors, as measured by decreased Gli-1 mRNA expression 8 hours post dose administration.

Daily (QD) administration of the Compound PO led to a dose dependent inhibition of tumor growth, with frank tumor regression seen at higher doses. The approximate effective daily oral dose for 50% inhibition of tumor growth (ED50) is between 8 mg/kg. When animals were treated QD for 21 days, long term survival was observed following cessation of treatment (>19 days), with little to no tumor re-growth. This demonstrates that the hedgehog inhibitor Compound 10 inhibits both the hedgehog pathway and tumor growth in a tumor dependent on the hedgehog pathway due to a genetic mutation.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:
1. A method of treating cancer comprising administering to a subject in need thereof a therapeutically effective amount of a compound of Formula 1a or 1b:

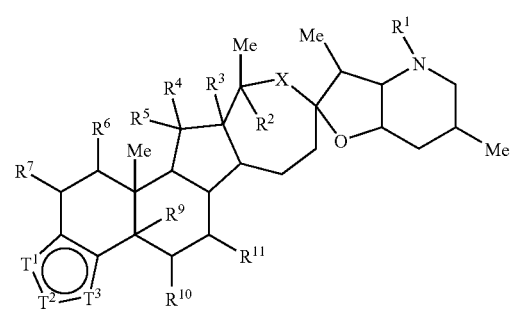

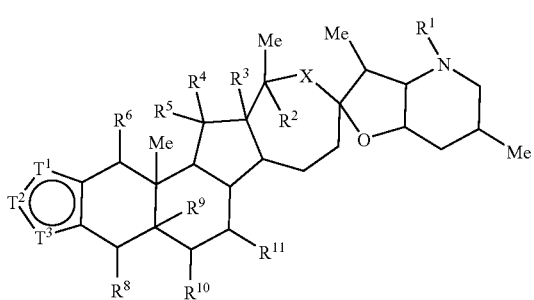

or a tautomer or pharmaceutically acceptable salt thereof, wherein:
$R^1$ is H, alkyl, alkenyl, alkynyl, aryl, cycloalkyl, hydroxyl, aralkyl, heteroaryl, heteroaralkyl, haloalkyl, $-SR^{20}$, $-OR^{20}$, $-C(O)R^{20}$, $-CO_2R^{20}$, $-OC(O)R^{20}$, $-C(O)N(R^{20})(R^{20})$, $-S(O)R^{20}$, $-S(O)_2R^{20}$, $-S(O)_2N(R^{20})(R^{20})$, $-[(W)-C(O)]_pR^{20}$, $-[(W)-C(O)O]_pR^{20}$, $-[(W)-OC(O)]_pR^{20}$, $-[(W)-SO_2]_pR^{20}$, $-[(W)-N(R^{20})SO_2]_pR^{20}$, $-[(W)-C(O)N(R^{20})]_pR^{20}$, $-[(W)-O]_pR^{20}$, $-[(W)-N(R^{20})]_pR^{20}$, or $-[(W)-S]_pR^{20}$;

each of $R^2$, $R^6$ and $R^9$ is independently H, alkyl, alkenyl, alkynyl, cycloalkyl, heterocycloalkyl, aryl, aralkyl, heteroaryl, heteroaralkyl, nitrile, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, or arylthio;

$R^3$ is H; or $R^2$ and $R^3$ taken together form a bond;

each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or $R^4$ and $R^5$ taken together form $=O$, $=S$, $=N(R^{20})$, $=N-OR^{20}$, or $=N(N(R^{20})_2)$;

each of $R^7$ and $R^8$ independently is H, alkyl, alkenyl, alkynyl, aryl, cycloalkyl, heterocycloalkyl, or aralkyl; or $R^6$ and $R^7$ taken together form a bond; or $R^8$ and $R^9$ taken together form a bond;

each of $R^{10}$ and $R^{11}$ independently is H, alkyl, alkenyl, alkynyl, aryl, cycloalkyl, heterocycloalkyl, or aralkyl; or $R^9$ and $R^{10}$ taken together form a bond; or $R^{10}$ and $R^{11}$ taken together form a bond;

$R^{20}$ independently for each occurrence is H, alkyl, alkenyl, alkynyl, aryl, cycloalkyl, heterocycloalkyl, aralkyl, heteroaryl, heteroaralkyl, or $-[C(R)_2]_q-R^{21}$; or any two occurrences of $R^{20}$ can be taken together to form a 4-8 membered optionally substituted ring which contains 0-3 heteroatoms selected from N, O, S, and P;

$R^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or carbonyl-containing group;

$R^{22}$ independently for each occurrence is H, halide, ester, amide, or nitrile;

$R^{23}$ independently for each occurrence is H, alkyl, alkenyl, alkynyl, cycloalkyl, aryl, aralkyl, heteroaryl, heteroaralkyl, perhaloalkyl, halide, nitro, nitrile, $=O$, $-SR^{20}$, $-OR^{20}$, $-N(R^{20})(R^{20})$, $-C(O)R^{20}$, $-CO_2R^{20}$, $-OC(O)R^{20}$, $-C(O)N(R^{20})(R^{20})$, $-N(R^{20})C(O)R^{20}$, $-N(R^{20})C(O)N(R^{20})(R^{20})$, $-S(O)R^{20}$, $-S(O)_2R^{20}$, $-S(O)_2N(R^{20})(R^{20})$, $-N(R^{20})S(O)_2R^{20}$, or $-[C(R)_2]_q-R^{21}$;

$R^{24}$ independently for each occurrence is H, alkyl, alkenyl, alkynyl, cycloalkyl, aryl, aralkyl, heteroaryl, heteroaralkyl, perhaloalkyl, halide, nitro, nitrile, $-SR^{20}$, $-OR^{20}$, $-N(R^{20})(R^{20})$, $-C(O)R^{20}$, $-CO_2R^{20}$, $-OC(O)R^{20}$, $-C(O)N(R^{20})(R^{20})$, $-N(R^{20})C(O)R^{20}$, $-N(R^{20})C(O)N(R^{20})(R^{20})$, $-S(O)R^{20}$, $-S(O)_2R^{20}$, $-S(O)_2N(R^{20})(R^{20})$, $-N(R^{20})S(O)_2R^{20}$, or $-[C(R^{20})_2]_q-R^{21}$;

p is 0, 1, 2, 3, 4, 5, or 6;
q is 0, 1, 2, 3, 4, 5, or 6;
R independently for each occurrence is H, alkyl, alkenyl, alkynyl, cycloalkyl, aryl, aralkyl, heteroaryl, or heteroarylalkyl;
-$T^1$-$T^2$-$T^3$- is Y—B-A, B—Y-A, or A-B—Y;
each of A and B independently is N, S or $C(R^{23})$;
W is a diradical;
X is a bond or $-C(R^{22})_2-$;
Y is $-O-$, $-S-$, or $-N(R^{24})-$;

and each alkyl, alkenyl, alkynyl, aryl, cycloalkyl, heterocycloalkyl, aralkyl, heteroaryl, heteroaralkyl, whether alone or part of another group, is optionally substituted; wherein said cancer is selected from the group consisting of acute lymphocytic leukemia, basal cell carcinoma, bile duct cancer, glioma, breast cancer, chondrosarcoma, chronic lymphocytic leukemia, chronic myeloid leukemia, colon cancer, esophageal cancer, gastric cancer, gastrointestinal stromal tumor, hepatocellular cancer, lung cancer, medulloblastoma, melanoma, multiple myeloma, neuroectodermal tumors, non-Hodgkin's type lymphoma, osteogenic sarcoma, ovarian cancer, pancreatic cancer, prostate cancer, testicular cancer, and sarcoma.

2. The method according to claim 1, wherein $R^1$ is H, alkyl, hydroxyl, aralkyl, heteroaryl, heteroaralkyl, —$OR^{20}$, —$C(O)R^{20}$, —$CO_2R^{20}$, —$C(O)N(R^{20})(R^{20})$, —$S(O)_2R^{20}$, —$S(O)_2N(R^{20})(R^{20})$, —$[(W)—C(O)]_pR^{20}$, —$[(W)—C(O)O]_pR^{20}$, —$[(W)—OC(O)]_pR^{20}$, —$[(W)—SO_2]_pR^{20}$, —$[(W)—N(R^{20})SO_2]_pR^{20}$, —$[(W)—C(O)N(R^{20})]_pR^{20}$, —$[(W)—O]_pR^{20}$, —$[(W)—N(R^{20})]_pR^{20}$, or —$[(W)—S]_pR^{20}$.

3. The method according to claim 2, wherein $R^1$ is H, alkyl, hydroxyl, —$C(O)R^{20}$, —$CO_2R^{20}$ or —$S(O)_2R^{20}$.

4. The method according to claim 1, wherein $R^2$ and $R^3$ taken together form a bond.

5. The method according to claim 1, wherein $R^4$ and $R^5$ are each H; or $R^4$ and $R^5$ taken together form =O or =S.

6. The method according to claim 5, wherein $R^4$ and $R^5$ are each H.

7. The method according to claim 1, wherein $R^6$, $R^7$, $R^8$, $R^9$, $R^{10}$, and $R^{11}$ are each independently H or alkyl.

8. The method according to claim 1, wherein $R^6$, $R^8$, $R^9$, $R^{10}$, and $R^{11}$ are each H.

9. The method according to claim 1, wherein X is a bond or —$CH_2$—.

10. The method according to claim 9, wherein X is —$CH_2$—.

11. The method according to claim 1, wherein Y is —O— or —$N(R^{24})$—.

12. The method according to claim 11, wherein Y is —$N(R^{24})$—.

13. The method according to claim 1, wherein -$T^1$-$T^2$-$T^3$- is A—B—Y, A is $CR^{23}$, B is N and Y is $NR^{24}$; or -$T^1$-$T^2$-$T^3$- is B—Y-A, A is N, B is $CR^{23}$ and Y is $NR^{24}$.

14. The method according to claim 1, wherein -$T^1$-$T^2$-$T^3$- is B—Y-A, A is $CR^{23}$, B is N and Y is $NR^{24}$; or -$T^1$-$T^2$-$T^3$- is B—Y-A, A is N, B is $CR^{23}$ and Y is O; or -$T^1$-$T^2$-$T^3$- is Y—B-A, A is N, B is $CR^{23}$ and Y is S.

15. The method according to claim 1, wherein $R^{24}$ is H, alkyl, or —$S(O)_2R^{20}$.

16. The method according to claim 1, wherein the compound of Formula 1a is a compound of the Formula 6a:

6a or a tautomer or pharmaceutically acceptable salt thereof, wherein:

$R^1$ is H, alkyl, alkenyl, alkynyl, aryl, cycloalkyl, hydroxyl, aralkyl, heteroaryl, heteroaralkyl, haloalkyl, —$SR^{20}$, —$OR^{20}$, —$C(O)R^{20}$, —$CO_2R^{20}$, —$OC(O)R^{20}$, —$C(O)N(R^{20})(R^{20})$, —$S(O)R^{20}$, —$S(O)_2R^{20}$, —$S(O)_2N(R^{20})(R^{20})$, —$[(W)—C(O)]_pR^{20}$, —$[(W)C(O)O]_pR^{20}$, —$[(W)—OC(O)]_pR^{20}$, —$[(W)—SO_2]_pR^{20}$, —$[(W)—N(R^{20})SO_2]_pR^{20}$, —$[(W)C(O)N(R^{20})]_pR^{20}$, —$[(W)—O]_pR^{20}$, —$[(W)—N(R^{20})]_pR^{20}$, or —$[(W)—S]_pR^{20}$;

each of $R^4$ and $R^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or $R^4$ and $R^5$ taken together form =O, =S, =$N(R^{20})$, =N—$OR^{20}$, or =$N(N(R^{20})_2)$;

$R^{20}$ independently for each occurrence is H, alkyl, alkenyl, alkynyl, aryl, cycloalkyl, heterocycloalkyl, aralkyl, heteroaryl, heteroaralkyl, or —$[C(R)_2]_q$—$R^{21}$; or any two occurrences of $R^{20}$ can be taken together to form a 4-8 membered optionally substituted ring which contains 0-3 heteroatoms selected from N, O, S, and P;

$R^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or carbonyl-containing group;

$R^{22}$ independently for each occurrence is H, halide, ester, amide, or nitrile;

$R^{23}$ independently for each occurrence is H, alkyl, alkenyl, alkynyl, cycloalkyl, aryl, aralkyl, heteroaryl, heteroaralkyl, perhaloalkyl, halide, nitro, nitrile, =O, —$SR^{20}$, —$OR^{20}$, —$N(R^{20})(R^{20})$, —$C(O)R^{20}$, —$CO_2R^{20}$, —$OC(O)R^{20}$, —$C(O)N(R^{20})(R^{20})$, —$N(R^{20})C(O)R^{20}$, —$N(R^{20})C(O)N(R^{20})(R^{20})$, —$S(O)R^{20}$, —$S(O)_2R^{20}$, —$S(O)_2N(R^{20})(R^{20})$, —$N(R^{20})S(O)_2R^{20}$, or $[C(R)_2]_q$—$R^{21}$;

$R^{24}$ independently for each occurrence is H, alkyl, alkenyl, alkynyl, cycloalkyl, aryl, aralkyl, heteroaryl, heteroaralkyl, perhaloalkyl, halide, nitro, nitrile, —$SR^{20}$, —$OR^{20}$, —$N(R^{20})(R^{20})$, —$C(O)R^{20}$, —$CO_2R^{20}$, —$OC(O)R^{20}$, —$C(O)N(R^{20})(R^{20})$, —$N(R^{20})C(O)R^{20}$, —$N(R^{20})C(O)N(R^{20})(R^{20})$, —$S(O)R^{20}$, —$S(O)_2R^{20}$, —$S(O)_2N(R^{20})(R^{20})$, —$N(R^{20})S(O)_2R^{20}$, or —$[C(R^{20})_2]_q$—$R^{21}$;

p is 0, 1, 2, 3, 4, 5, or 6;

q is 0, 1, 2, 3, 4, 5, or 6;

R independently for each occurrence is H, alkyl, alkenyl, alkynyl, cycloalkyl, aryl, aralkyl, heteroaryl, or heteroarylalkyl;

-$T^1$-$T^2$-$T^3$- is Y—B-A, B—Y-A, or A-B—Y;

each of A and B independently is N, S or $C(R^{23})$;

W is a diradical;

X is a bond or —$C(R^{22})_2$—;

Y is —O—, —S—, or —$N(R^{24})$—;

and each alkyl, alkenyl, alkynyl, aryl, cycloalkyl, heterocycloalkyl, aralkyl, heteroaryl, heteroaralkyl, whether alone or part of another group, is optionally substituted.

17. The method according to claim 16, wherein $R^1$ is H, alkyl, hydroxyl, aralkyl, heteroaryl, heteroaralkyl, —$OR^{20}$, —$C(O)R^{20}$, —$CO_2R^{20}$, —$C(O)N(R^{20})(R^{20})$, —$S(O)_2R^{20}$, —$S(O)_2N(R^{20})(R^{20})$, —$[(W)—C(O)]_pR^{20}$, —$[(W)—C(O)O]_pR^{20}$, —$[(W)—OC(O)]_pR^{20}$, —$[(W)—SO_2]_pR^{20}$, —$[(W)—N(R^{20})SO_2]_pR^{20}$, —$[(W)—C(O)N(R^{20})]_pR^{20}$, —$[(W)—O]_pR^{20}$, —$[(W)—N(R^{20})]_pR^{20}$, or —$[(W)—S]_pR^{20}$.

18. The method according to claim 17, wherein $R^1$ is H, alkyl, hydroxyl, —$C(O)R^{20}$, —$CO_2R^{20}$ or —$S(O)_2R^{20}$.

19. The method according to claim 16, wherein $R^4$ and $R^3$ are each H.

20. The method according to claim 16, wherein X is a bond or —$CH_2$—.

21. The method according to claim 20, wherein X is —CH$_2$—.

22. The method according to claim 16, wherein Y is —O— or —N(R$^{24}$)—.

23. The method according to claim 22, wherein Y is —N(R$^{21}$)—.

24. The method according to claim 16, wherein -T$^1$-T$^2$-T$^3$- is A-B—Y, A is CR$^{23}$, B is N and Y is NR$^{24}$; or -T$^1$-T$^2$-T$^3$- is B—Y-A, A is N, B is CR$^{23}$ and Y is NR$^{24}$.

25. The method according to claim 16, wherein -T$^1$-T$^2$-T$^3$- is B—Y-A, A is CR$^{23}$, B is N and Y is NR$^{24}$; or -T$^1$-T$^2$-T$^3$- is B—Y-A, A is N, B is CR$^{23}$ and Y is O; or -T$^1$-T$^2$-T$^3$- is Y—B-A, A is N, B is CR$^{23}$ and Y is S.

26. The method according to claim 16, wherein R$^{24}$ is H, alkyl, or —S(O)$_2$R$^{20}$.

27. The method according to claim 1, wherein the compound of Formula 1b is a compound of the Formula 11b:

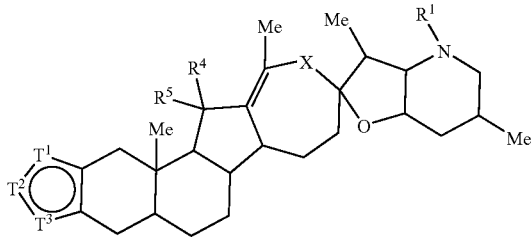

11b or a tautomer or pharmaceutically acceptable salt thereof, wherein:

R$^1$ is H, alkyl, alkenyl, alkynyl, aryl, cycloalkyl, hydroxyl, aralkyl, heteroaryl, heteroaralkyl, haloalkyl, —SR$^{20}$, —OR$^{20}$, —C(O)R$^{20}$, —CO$_2$R$^{20}$, —OC(O)R$^{20}$, —C(O)N(R$^{20}$)(R$^{20}$), —S(O)R$^{20}$, —S(O)$_2$R$^{20}$, —S(O)$_2$N(R$^{20}$)(R$^{20}$), —[(W)—C(O)]$_p$R$^{20}$, —[(W)—C(O)O]$_p$R$^{20}$, —[(W)—OC(O)]$_p$R$^{20}$, —[(W)—SO$_2$]$_p$R$^{20}$, —[(W)—N(R$^{20}$)SO$_2$]$_p$R$^{20}$, —[(W)—C(O)N(R$^{20}$)]$_p$R$^{20}$, —[(W)—O]$_p$R$^{20}$, —[(W)—N(R$^{20}$)]$_p$R$^{20}$, or —[(W)—S]$_p$R$^{20}$;

each of R$^4$ and R$^5$ independently is H, alkyl, alkenyl, alkynyl, aryl, cycloalkyl, nitrile, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl; or R$^4$ and R$^5$ taken together form =O, =S, =N(R$^{20}$), =N—OR$^{20}$, or =N(N(R$^{20}$)$_2$);

R$^{20}$ independently for each occurrence is H, alkyl, alkenyl, alkynyl, aryl, cycloalkyl, heterocycloalkyl, aralkyl, heteroaryl, heteroaralkyl, or —[C(R)$_2$]$_q$—R$^{21}$; or any two occurrences of R$^{20}$ can be taken together to form a 4-8 membered optionally substituted ring which contains 0-3 heteroatoms selected from N, O, S, and P;

R$^{21}$ independently for each occurrence is H, cycloalkyl, aryl, heteroaryl, heterocyclyl; alkoxyl, aryloxy, acyloxy, halide, sulfhydryl, alkylthio, arylthio, aralkylthio, hydroxyl, amino, acylamino, amido, or carbonyl-containing group;

R$^{22}$ independently for each occurrence is H, halide, ester, amide, or nitrile;

R$^{23}$ independently for each occurrence is H, alkyl, alkenyl, alkynyl, cycloalkyl, aryl, aralkyl, heteroaryl, heteroaralkyl, perhaloalkyl, halide, nitro, nitrile, =O, —SR$^{20}$, —OR$^{20}$ N(R$^{20}$)(R$^{20}$), —C(O)R$^{20}$, —CO$_2$R$^{20}$, —OC(O)R$^{20}$, —C(O)N(R$^{20}$)(R$^{20}$), —N(R$^{20}$)C(O)R$^{20}$, —N(R$^{20}$)C(O)N(R$^{20}$)(R$^{20}$), —S(O)R$^{20}$, —S(O)$_2$R$^{20}$, —S(O)$_2$N(R$^{20}$)(R$^{20}$), —N(R$^{20}$)S(O)$_2$R$^{20}$, or —[C(R)$_2$]$_p$—R$^{21}$;

R$^{24}$ independently for each occurrence is H, alkyl, alkenyl, alkynyl, cycloalkyl, aryl, aralkyl, heteroaryl, heteroaralkyl, perhaloalkyl, halide, nitro, nitrile, —SR$^{20}$, —OR$^{20}$, —N(R$^{20}$)(R$^{20}$), —C(O)R$^{20}$, —CO$_2$R$^{20}$, —OC(O)R$^{20}$, —C(O)N(R$^{20}$)(R$^{20}$), —N(R$^{20}$)C(O)R$^{20}$, —N(R$^{20}$)C(O)N(R$^{20}$)(R$^{20}$), —S(O)R$^{20}$, —S(O)$_2$R$^{20}$, —S(O)$_2$N(R$^{20}$)(R$^{20}$), —N(R$^{20}$)S(O)$_2$R$^{20}$, or —[C(R$^{20}$)$_2$]$_p$—R$^{21}$;

p is 0, 1, 2, 3, 4, 5, or 6;

q is 0, 1, 2, 3, 4, 5, or 6;

R independently for each occurrence is H, alkyl, alkenyl, alkynyl, cycloalkyl, aryl, aralkyl, heteroaryl, or heteroarylalkyl;

-T$^1$-T$^2$-T$^3$- is Y—B-A, B—Y-A, or A-B—Y;

each of A and B independently is N, S or C(R$^{23}$);

W is a diradical;

X is a bond or —C(R$^{22}$)$_2$—;

Y is —O—, —S—, or —N(R$^{24}$)—;

and each alkyl, alkenyl, alkynyl, aryl, cycloalkyl, heterocycloalkyl, aralkyl, heteroaryl, heteroaralkyl, whether alone or part of another group, is optionally substituted.

28. The method according to claim 27, wherein R$^1$ is H, alkyl, hydroxyl, aralkyl, heteroaryl, heteroaralkyl, —OR$^{20}$, —C(O)R$^{20}$, —CO$_2$R$^{20}$, —C(O)N(R$^{20}$)(R$^{20}$), —S(O)$_2$R$^{20}$, —S(O)$_2$N(R$^{20}$)(R$^{20}$), —[(W)—C(O)]$_p$R$^{20}$, —[(W)—C(O)O]$_p$R$^{20}$, —[(W)—OC(O)]$_p$R$^{20}$, —[(W)—SO$_2$]$_p$R$^{20}$, —[(W)—N(R$^{20}$)SO$_2$]$_p$R$^{20}$, —[(W)—C(O)N(R$^{20}$)]$_p$R$^{20}$, —[(W)—O]$_p$R$^{20}$, —[(W)—N(R$^{20}$)]$_p$R$^{20}$, or —[(W)—S]$_p$R$^{20}$.

29. The method according to claim 28, wherein R$^1$ is H, alkyl, hydroxyl, —C(O)R$^{20}$, —CO$_2$R$^{20}$ or —S(O)$_2$R$^{20}$.

30. The method according to claim 27, wherein R$^4$ and R$^5$ are each H.

31. The method according to claim 27, wherein X is a bond or —CH$_2$—.

32. The method according to claim 31, wherein X is —CH$_2$—.

33. The method according to claim 27, wherein Y is —O— or —N(R$^{24}$)—.

34. The method according to claim 33, wherein Y is —N(R$^{24}$)—.

35. The method according to claim 27, wherein -T$^1$-T$^2$-T$^3$- is A-B—Y, A is CR$^{23}$, B is N and Y is NR$^{24}$; or -T$^1$-T$^2$-T$^3$- is B—Y-A, A is N, B is CR$^{23}$ and Y is NR$^{24}$.

36. The method according to claim 27, wherein -T$^1$-T$^2$-T$^3$- is B—Y-A, A is CR$^{23}$, B is N and Y is NR$^{24}$; or -T$^1$-T$^2$-T$^3$- is B—Y-A, A is N, B is CR$^{23}$ and Y is O; or -T$^1$-T$^2$-T$^3$- is Y—B-A, A is N, B is CR$^{23}$ and Y is S.

37. The method according to claim 27, wherein R$^{24}$ is H, alkyl, or —S(O)$_2$R$^{20}$.

38. A method of treating cancer comprising administering to a subject in need thereof a therapeutically effective amount of a compound selected from the group consisting of:

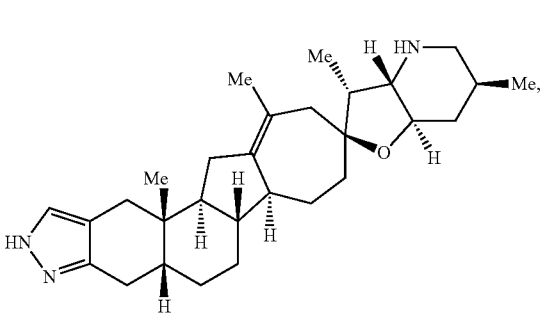

63
-continued
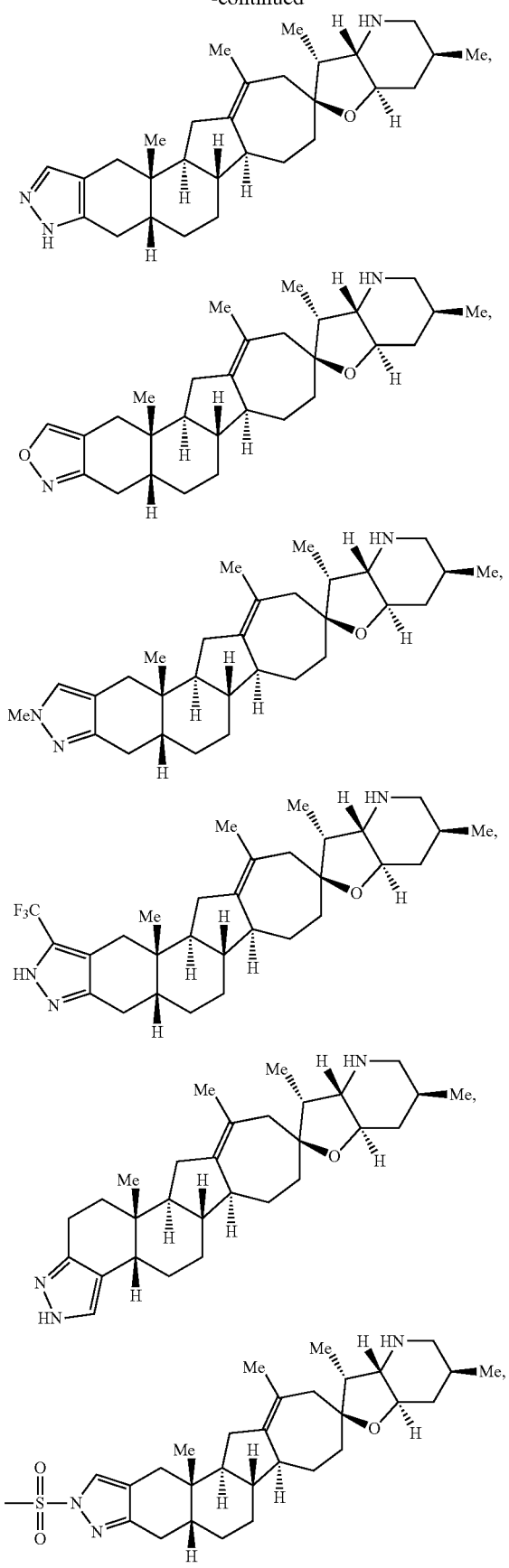
64
-continued
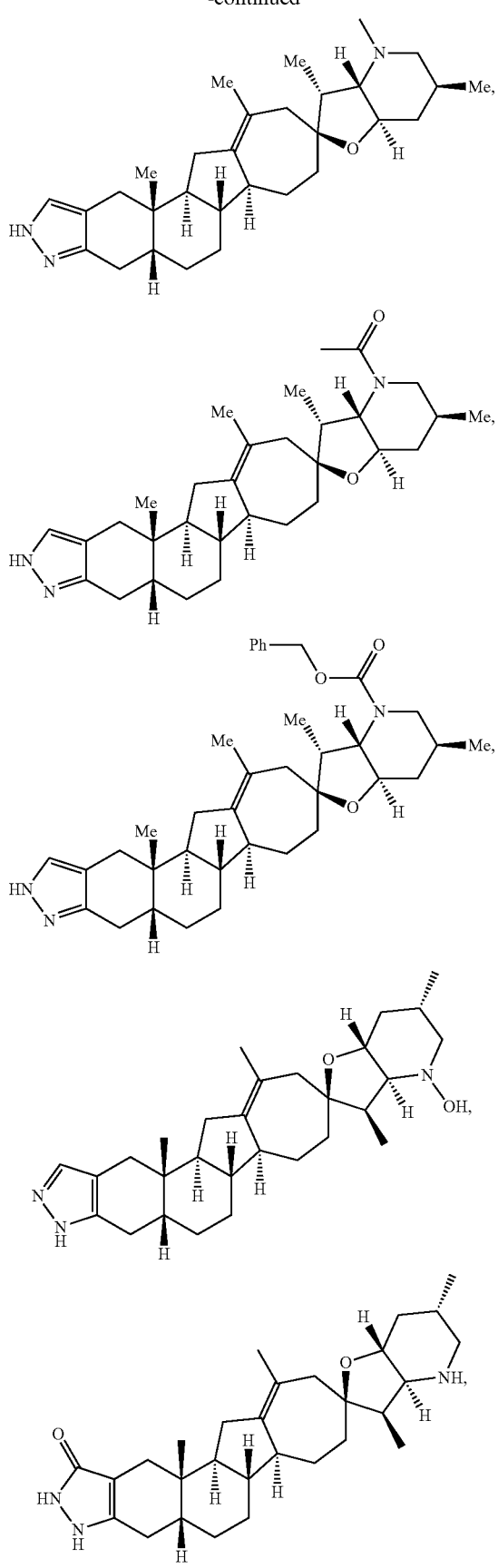

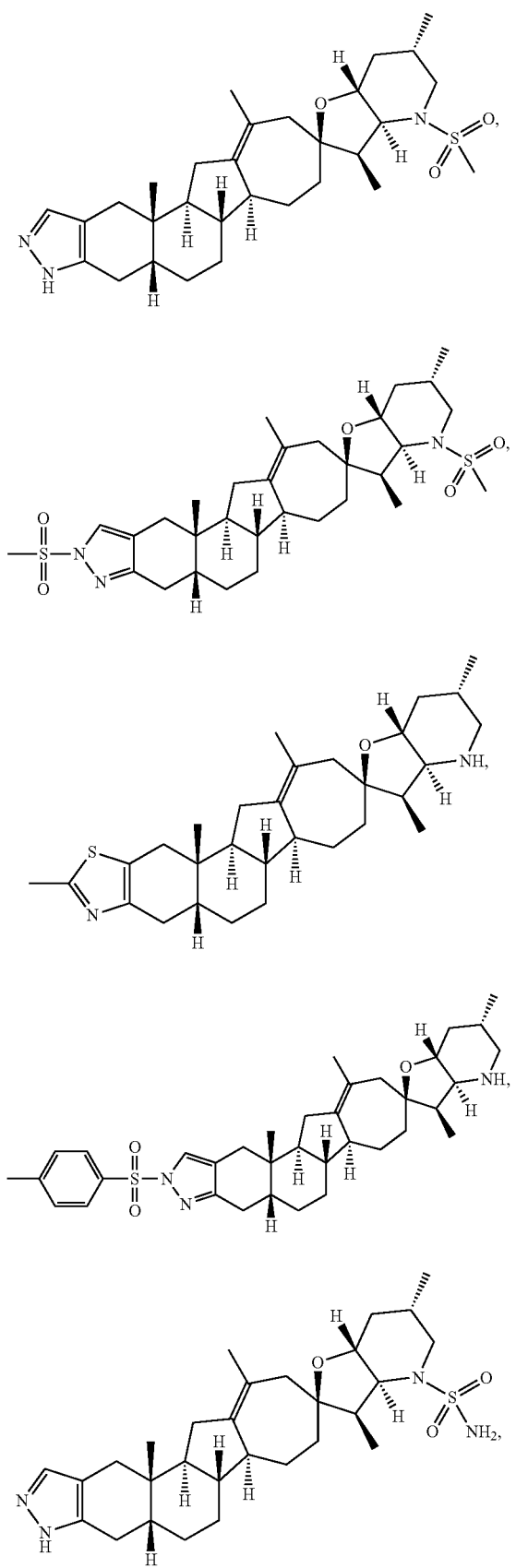

or a tautomer or a pharmaceutically acceptable salt thereof; wherein said cancer is selected from the group consisting of acute lymphocytic leukemia, basal cell carcinoma, bile duct cancer, glioma, breast cancer, chondrosarcoma, chronic lymphocytic leukemia, chronic myeloid leukemia, colon cancer, esophageal cancer, gastric cancer, gastrointestinal stromal tumor, hepatocellular cancer, lung cancer, medulloblastoma, melanoma, multiple myeloma, neuroectodermal tumors, non-Hodgkin's type lymphoma, osteogenic sarcoma, ovarian cancer, pancreatic cancer, prostate cancer, testicular cancer, and sarcoma.

39. The method according to claim 1, wherein the cancer is basal cell carcinoma, pancreatic cancer, prostate cancer, osteogenic sarcoma, chondrosarcoma, non-Hodgkin's type lymphoma, acute lymphocytic leukemia, chronic lymphocytic leukemia, chronic myeloid leukemia, gastric cancer, esophageal cancer, multiple myeloma, lung cancer, glioma, breast cancer, hepatocellular cancer, ovarian cancer, colon cancer or medulloblastoma.

40. The method according to claim 1, wherein the cancer is pancreatic cancer.

41. The method according to claim 1, wherein the cancer is chondrosarcoma.

42. The method according to claim 1, wherein the cancer is lung cancer.

43. The method according to claim 42, wherein the lung cancer is small cell lung cancer.

44. The method according to claim 1, wherein the cancer is basal cell carcinoma.

45. The method according to claim 1, wherein the cancer is medulloblastoma.

46. The method according to claim 1, wherein the cancer is acute lymphocytic leukemia.

47. The method according to claim 1, wherein the cancer is chronic lymphocytic leukemia.

48. The method according to claim 1, wherein the cancer is ovarian cancer.

49. The method according to claim 1, wherein the cancer is osteogenic sarcoma.

50. The method according to claim 1, wherein the cancer is chronic myeloid leukemia.

51. The method according to claim 1, wherein the compound is used in combination with one or more chemotherapeutic or other anti-cancer agent.

52. The method according to claim 51, wherein the other anti-cancer agent is radiation.

53. The method according to claim 1, wherein the compound is administered locally to a tumor.

54. The method according to claim 1, wherein the compound is administered systemically.

55. The method according to claim 1, wherein the mode of administration of said compound is inhalation, oral, intravenous, sublingual, ocular, transdermal, rectal, vaginal, topical, intramuscular, intraperitoneal, epidural, subcutaneous, buccal, or nasal.

56. The method according to claim 55, wherein the mode of administration is oral, intravenous, or topical.

* * * * *

UNITED STATES PATENT AND TRADEMARK OFFICE
CERTIFICATE OF CORRECTION

| | | |
|---|---|---|
| PATENT NO. | : 7,994,191 B2 | Page 1 of 1 |
| APPLICATION NO. | : 12/629382 | |
| DATED | : August 9, 2011 | |
| INVENTOR(S) | : Alfredo C. Castro, Michael J. Grogan and Martin R. Tremblay | |

It is certified that error appears in the above-identified patent and that said Letters Patent is hereby corrected as shown below:

On the Title Pg, Item (56), right hand column, line 2 of text under the heading "OTHER PUBLICATIONS", "Drosophilia", should read -- Drosophila --.

On the Title Pg, Item (56), right hand column, line 15 of text under the heading "OTHER PUBLICATIONS", "Medullablastoma", should read -- Medulloblastoma --.

Column 58, line 37; and column 60, line 21; and column 61, 55, "heterocyclyl;" should read -- heterocyclyl, --.

Column 60, line 64, "$R^3$" should read -- $R^5$ --.

Column 61, line 6, "–N($R^{21}$)–" should read -- –N($R^{24}$)–. --.

Column 61, line 63, "–O$R^{20}$)N($R^{20}$)($R^{20}$)," should read -- –O$R^{20}$, –N($R^{20}$)($R^{20}$), --.

Signed and Sealed this
Twenty-ninth Day of November, 2011

David J. Kappos
*Director of the United States Patent and Trademark Office*